US009382522B2

(12) United States Patent
Bolchakova et al.

(10) Patent No.: US 9,382,522 B2
(45) Date of Patent: Jul. 5, 2016

(54) ***THERMUS SCOTODUCTUS* NUCLEIC ACID POLYMERASES**

(75) Inventors: Elena V. Bolchakova, Union City, CA (US); James E. Rozzelle, San Francisco, CA (US)

(73) Assignee: APPLIED BIOSYSTEMS, LLC, Carlsbad, CA (US)

(*) Notice: Subject to any disclaimer, the term of this patent is extended or adjusted under 35 U.S.C. 154(b) by 704 days.

(21) Appl. No.: 12/544,199

(22) Filed: Aug. 19, 2009

(65) Prior Publication Data

US 2010/0086970 A1 Apr. 8, 2010

Related U.S. Application Data

(62) Division of application No. 10/799,369, filed on Mar. 12, 2004, now abandoned.

(51) Int. Cl.
*C12N 9/12* (2006.01)
*C12P 19/34* (2006.01)

(52) U.S. Cl.
CPC ............... *C12N 9/1252* (2013.01); *C12P 19/34* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,801,537 | A | 1/1989 | Nagarajan et al. |
| 4,806,472 | A | 2/1989 | de Louvencourt et al. |
| 4,873,192 | A | 10/1989 | Kunkel |
| 4,935,361 | A | 6/1990 | Lin et al. |
| 4,965,188 | A | 10/1990 | Mullis et al. |
| 4,966,841 | A | 10/1990 | Riley |
| 5,063,158 | A | 11/1991 | Schoner et al. |
| 5,079,352 | A | 1/1992 | Gelfand et al. |
| 5,266,490 | A | 11/1993 | Davis et al. |
| 5,322,770 | A | 6/1994 | Gelfand |
| 5,322,785 | A | 6/1994 | Comb et al. |
| 5,352,778 | A | 10/1994 | Comb et al. |
| 5,432,082 | A | 7/1995 | Galeotti et al. |
| 5,455,170 | A | 10/1995 | Abramson et al. |
| 5,489,523 | A | 2/1996 | Mathur |
| 5,500,363 | A | 3/1996 | Comb et al. |
| 5,541,311 | A | 7/1996 | Dahlberg et al. |
| 5,545,552 | A | 8/1996 | Mathur |
| 5,583,023 | A | 12/1996 | Cerutti et al. |
| 5,602,756 | A | 2/1997 | Atwood et al. |
| 5,604,118 | A | 2/1997 | Giri et al. |
| 5,614,365 | A | 3/1997 | Tabor et al. |
| 5,691,142 | A | 11/1997 | Dahlberg et al. |
| 5,723,591 | A | 3/1998 | Livak et al. |
| 5,994,069 | A | 11/1999 | Hall et al. |
| 6,228,628 | B1 * | 5/2001 | Gelfand et al. ............... 435/194 |
| 6,635,463 | B2 | 10/2003 | Ma et al. |

FOREIGN PATENT DOCUMENTS

| | | |
|---|---|---|
| EP | 0482714 | 4/1992 |
| WO | WO-9101384 | 2/1991 |
| WO | WO-9206188 | 4/1992 |
| WO | WO-01/90337 A2 | 11/2001 |

OTHER PUBLICATIONS

U.S. Pat. No. 5,405,744, Apr. 1995, Abramson et al.*
"International Search Report for Application No. PCT/US02/29102, date mailed Jun. 30, 2004", 8 pgs.
Altschul, S. F., et al., "Basic local alignment search tool", *J. Mol. Biol.*, 215(3), (Oct. 5, 1990),403-10.
Altschul, S. F., "Gapped BLAST and PSI-BLAST: A New Generation of Protein Database Search Programs", *Nucleic Acids Research*, 25(17), (1997),3389-3402 .
Asakura, K., et al., "Cloning, nucleotide sequence, and expression in *Escherichia coli* of DNA polymerase gene (polA) from Thermus therophilus HB8", *J. Ferment. Bioeng.* (Japan), 76(4), 1993,265-269.
Barnes, W. M., "The fidelity of Taq polymerase catalyzing PCR is improved by an N-terminal deletion", *Gene*, 112(1), (Mar. 1, 1992),29-35.
Batzer, M. A., et al., "Enhanced evolutionary PCR using oligonucleotides with inosine at the 3'-terminus", *Nucleic Acid Res.*, 19(18), (Sep. 25, 1991),5081.
Corpet, F., "Multiple sequence alignment with hierarchical clustering", *Nucleic Acids Res.*, 16(22), (Nov. 25, 1988),10881-90.
Erlich, H. A., et al., "Recent advances in the polymerase chain reaction.", *Science*, 252(5013), (Jun. 21, 1991),1643-1651.
Henikoff, S., et al., "Amino acid substitution matrices from protein blocks", *Proc. Natl. Acad. Sci. USA*, 89(22), (Nov. 15, 1989),10915-9.
Higgins, D. G., et al., "CLUSTAL: a package for performing multiple sequence alignment on a microcomputer.", *Gene*, 73(1), (Dec. 15, 1988),237-44.
Higgins, D. G., et al., "Fast and sensitive multiple sequence alignments on a microcomputer.", *Comput Appl Biosci.*, 5(2), (Apr. 1989),151-153.
Huang, X., et al., "Parallelization of a local similarity algorithm.", *Comput Appl Biosci.*, 8(2), (Apr. 1992),155-65.
Kunkel, T. A., "Rapid and Efficient Site-Specific Mutagenesis Without Phenotypic Selection", *Proc. Natl. Acad. Sci. USA*, 82, (1985),488-492.
Kunkel, T. A., et al., "Rapid and efficient site-specific mutagenesis without phenotypic selection.", *Methods in Enzymol.*, 154, 1987,367-82.
Lawyer, F. C., et al., "High-level expression, purification, and enzymatic characterization of full-length Thermus aquaticus DNA polymerase and a truncated form deficient in 5' to 3' exonuclease activity", *PCR Methods and Applications*, 2(4), (May 1993),275-287.

(Continued)

*Primary Examiner* — Richard Hutson

(57) ABSTRACT

The invention provides nucleic acids and polypeptides for a nucleic acid polymerase from a thermophilic organism, *Thermus scotoductus*. The invention also provides methods for using these nucleic acids and polypeptides.

18 Claims, 6 Drawing Sheets

(56) References Cited

OTHER PUBLICATIONS

Lawyer, F. C., et al., "Isolation, characterization, and expression in *Escherichia coli* of the DNA polymerase gene from *Thermus aquaticus*", *J. Biol. Chem.*, 264(11), (Apr. 15, 1989),6427-6437.

Ohtsuka, E., et al., "An alternative approach to deoxyoligonucleotides as hybridization probes by insertion of deoxyinosine at ambiguous codon positions", *J. Biol. Chem.*, 260(5), (Mar. 10, 1985),2605-8.

Pearson, W. R., et al., "Using the FASTA program to search protein and DNA sequence databases.", *Methods Mol Biol.*, 24, (1994),307-331.

Rossolini, G. M., et al., "Use of deoxyinosine-containing primers vs degenerate primers for polymerase chain reaction based on ambiguous sequence information", *Mol. Cell. Probes*, 8(2), (Apr. 1994),91-8.

Sawano, A., et al., "Directed evolution of green fluorescent protein by a new versatile PCR strategy for site-directed and semi-random mutagenesis", *Nucleic Acids Res*. 28 (16), (Aug. 15, 2000),E78.

Tabor, S., et al., "A single residue in DNA polymerases of the *Escherichia coli* DNA polymerase I family is critical for distinguishing between deoxy- and dideoxyribonucleotides", *Proc Natl Acad Sci U S A.*, 92 (14), (Jul. 3, 1995),6339-6343.

Vainshtein, I., et al., "Peptide rescue of an N-terminal truncation of the Stoffel fragment of taq DNA polymerase", *Protein Science*, 5(9), (Sep. 1996), 1785-1792.

Walker, G. T., et al., "Strand displacement amplification—an isothermal, in vitro DNA amplification technique", *Nucl. Acids Res.*, 20(7), (Apr. 11, 1992),1691-1696.

Xu, Yang, et al., "Biochemical and mutational studies of the 5'-3' exonuclease of DNA polymerase I of *Escherichia coli.", J Molecular Biology*, 268, (May 2, 1997),284-302.

"Supplemental European Search Report for EPO Application No. 02805994.7",(Aug. 3, 2006), 3 pgs.

"*Thermus* sp. X-1 DNA Polymerase (TX1 DNA Polymerase)", Database Geneseq (online), (retrived from EBI accession No. GSP: ABP97500), (Nov. 6, 2003), 1 pg.

* cited by examiner

```
     1                                                  50
Taq  MRGMLPLFEP KGRVLLVDGH HLAYRTFHAL KGLTTSRGEP VQAVYGFAKS
Tth  MEAMLPLFEP KGRVLLVDGH HLAYRTFFAL KGLTTSRGEP VQAVYGFAKS
Tfi  MTPLFDLEEP PKRVLLVDGH HLAYRTFYAL S.LTTSRGEP VQMVYGFARS
Tsc  MRAMLPLFEP KGRVLLVDGH HLAYRTFFAL KGLTTSRGEP VQAVYGFAKS

     51                                                100
Taq  LLKALKEDG. DAVIVVFDAK APSFRHEAYG GYKAGRAPTP EDFPRQLALI
Tth  LLKALKEDGY KAVFVVFDAK APSFRHEAYE AYKAGRAPTP EDFPRQLALI
Tfi  LLKALKEDG. QAVVVVFDAK APSFRHEAYE AYKAGRAPTP EDFPRQLALV
Tsc  LLKALKEDG. DVVIVVFDAK APSFRHQIYE AYKAGRAPTP EDFPRQLALI

     101                                               150
Taq  KELVDLLGLA RLEVPGYEAD DVLASLAKKA EKEGYEVRIL TADKDLYQLL
Tth  KELVDLLGFT RLEVPGYEAD DVLATLAKKA EKEGYEVRIL TADRDLYQLV
Tfi  KRLVDLLGLV RLEAPGYEAD DVLGTLAKKA EREGMEVRIL TGDRDFFQLL
Tsc  KEMVDLLGLE RLEVPGFEAD DVLATLAKKA EKEGYEVRIL TADRDLYQLL

     151                                               200
Taq  SDRIHVLHPE GYLITPAWLW EKYGLRPDQW ADYRALTGDE SDNLPGVKGI
Tth  SDRVAVLHPE GHLITPEWLW EKYGLRPEQW VDFRALVGDP SDNLPGVKGI
Tfi  SEKVSVLLPD GTLVTPKDVQ EKYGVPPERW VDFRALTGDR SDNIPGVAGI
Tsc  SERISILHPE GYLITPEWLW EKYGLKPSQW VDYRALAGDP SDNIPGVKGI

     201                                               250
Taq  GEKTARKLLE EWGSLEALLK NLDRLKPA.I REKILAHMDD LKLSWDLAKV
Tth  GEKTALKLLK EWGSLENLLK NLDRVKPENV REKIKAHLED LRLSLELSRV
Tfi  GEKTALRLLA EWGSVENLLK NLDRVKPDSL RRKIEAHLED LHLSLDLARI
Tsc  GEKTAAKLIR EWGSLENLLK HLEQVKPASV REKILSHMED LKLSLELSRV
```

FIG. 1A

```
     251                                                    300
Taq  RTDLPLEVDF A..KRREPDR ERLRAFLERL EFGSLLHEFG LLESPKALEE
Tth  RTDLPLEVDL A..QGREPDR EGLRAFLERL EFGSLLHEFG LLEAPAPLEE
Tfi  RTDLPLEVDF KALRRRTPDL EGLRAFLEEL EFGSLLHEFG LLGGEKPREE
Tsc  RTDLPLQVDF A..RRREPDR EGLKAFLERL EFGSLLHEFG LLESPVAAEE

     301                                                    350
Taq  APWPPPEGAF VGFVLSRKEP MWADLLALAA ARGGRVHRAP EPYKALRDLK
Tth  APWPPPEGAF VGFVLSRPEP MWAELKALAA CRDGRVHRAA DPLAGLKDLK
Tfi  APWPPPEGAF VGFLLSRKEP MWAELLALAA ASEGRVHRAT SPVEALADLK
Tsc  APWPPPEGAF VGYVLSRPEP MWAELNALAA AWEGRVYRAE DPLEALRGLG

     351                                                    400
Taq  EARGLLAKDL SVLALREGLG LPPGDDPMLL AYLLDPSNTT PEGVARRYGG
Tth  EVRGLLAKDL AVLASREGLD LVPGDDPMLL AYLLDPSNTT PEGVARRYGG
Tfi  EARGFLAKDL AVLALREGVA LDPTDDPLLV AYLLDPANTH PEGVARRYGG
Tsc  EVRGLLAKDL AVLALREGIA LAPGDDPMLL AYLLDPSNTA PEGVARRYGG

     401                                                    450
Taq  EWTEEAGERA ALSERLFANL WGRLEGEERL LWLYREVERP LSAVLAHMEA
Tth  EWTEDAAHRA LLSERLHRNL LKRLEGEEKL LWLYHEVEKP LSRVLAHMEA
Tfi  EFTEDAAERA LLSERLFQNL FPRLS..EKL LWLYQEVERP LSRVLAHMEA
Tsc  EWTEEAGERA LLSERLYAAL LERLKGEERL LWLYEEVEKP LSRVLAHMEA

     451                                                    500
Taq  TGVRLDVAYL RALSLEVAEE IARLEAEVFR LAGHPFNLNS RDQLERVLFD
Tth  TGVRLDVAYL QALSLELAEE IRRLEEEVFR LAGHPFNLNS RDQLERVLFD
Tfi  RGVRLDVPLL EALSFELEKE MERLEGEVFR LAGHPFNLNS RDQLERVLFD
Tsc  TGVRLDVAYL KALSLEVEAE LRRLEEEVHR LAGHPFNLNS RDQLERVLFD
```

FIG. 1B

```
      501                                                    550
Taq   ELGLPAIGKT EKTGKRSTSA AVLEALREAH PIVEKILQYR ELTKLKSTYI
Tth   ELRLPALGKT QKTGKRSTSA AVLEALREAH PIVEKILQHR ELTKLKNTYV
Tfi   ELGLTPVGRT EKTGKRSTAQ GALEALRGAH PIVELILQYR ELSKLKSTYL
Tsc   ELGLPAIGKT EKTGKRSTSA AVLEALREAH PIVDRILQYR ELSKLKGTYI

      551                                                    600
Taq   DPLPDLIHPR TGRLHTRFNQ TATATGRLSS SDPNLQNIPV RTPLGQRIRR
Tth   DPLPSLVHPR TGRLHTRFNQ TATATGRLSS SDPNLQNIPV RTPLGQRIRR
Tfi   DPLPRLVHPR TGRLHTRFNQ TATATGRLSS SDPNLQNIPV RTPLGQRIRK
Tsc   DPLPALVHPK TNRLHTRFNQ TATATGRLSS SDPNLQNIPV RTPLGQRIRR

      601                                                    650
Taq   AFIAEEGWLL VALDYSQIEL RVLAHLSGDE NLIRVFQEGR DIHTETASWM
Tth   AFVAEAGWAL VALDYSQIEL RVLAHLSGDE NLIRVFQEGK DIHTQTASWM
Tfi   AFVAEEGWLL LAADYSQIEL RVLAHLSGDE NLKRVFREGK DIHTETAAWM
Tsc   AFVAEEGWRL VVLDYSQIEL RVLAHLSGDE NLIRVFQEGQ DIHTQTASWM

      651                                                    700
Taq   FGVPREAVDP LMRRAAKTIN FGVLYGMSAH RLSQELAIPY EEAQAFIERY
Tth   FGVPPEAVDP LMRRAAKTVN FGVLYGMSAH RLSQELAIPY EEAVAFIERY
Tfi   FGLDPALVDP KMRRAAKTVN FGVLYGMSAH RLSQELGIDY KEAEAFIERY
Tsc   FGVPPEAVDS LMRRAAKTIN FGVLYGMSAH RLSGELAIPY EEAVAFIERY

      701                                                    750
Taq   FQSFPKVRAW IEKTLEEGRR RGYVETLFGR RRYVPDLEAR VKSVREAAER
Tth   FQSFPKVRAW IEKTLEEGRK RGYVETLFGR RRYVPDLNAR VKSVREAAER
Tfi   FQSFPKVRAW IERTLEEGRT RGYVETLFGR RRYVPDLASR VRSVREAAER
Tsc   FQSYPKVRAW IEKTLAEGRE RGYVETLFGR RRYVPDLASR VKSIREAAER
```

FIG. 1C

| | 751 | | | | 800 |
|---|---|---|---|---|---|
| Taq | MAFNMPVQGT | AADLMKLAMV | KLFPRLEEMG | ARMLLQVHDE | LVLEAPKERA |
| Tth | MAFNMPVQGT | AADLMKLAMV | KLFPRLREMG | ARMLLQVHDE | LLLEAPQARA |
| Tfi | MAFNMPVQGT | AADLMKIAMV | KLFPRLKPLG | AHLLLQVHDE | LVLEVPEDRA |
| Tsc | MAFNMPVQGT | AADLMKLAMV | KLFPRLQELG | ARMLLQVHDE | LVLEAPKEQA |

| | 801 | | | 837 |
|---|---|---|---|---|
| Taq | EAVARLAKEV | MEGVYPLAVP | LEVEVGIGED | WLSAKE. |
| Tth | EEVAALAKEA | MEKAYPLAVP | LEVEVGMGED | WLSAKG. |
| Tfi | EEAKALVKEV | MENAYPLDVP | LEVEVGVGRD | WLEAKQD |
| Tsc | EEVAQEAKRT | MEEVWPLKVP | LEVEVGIGED | WLSAKA. |

FIG. 1D

```
      1                                                  50
X-1   MRAMLPLFEP KGRVLLVDGH HLAYRTFFAL KGLTTSRGEP VQAVYGFAKS
SM3   MRAMLPLFEP KGRVLLVDGH HLAYRTFFAL KGLTTSRGEP VQAVYGFAKS
Vi7a  MRAMLPLFEP KGRVLLVDGH HLAYRTFFAL KGLTTSRGEP VQAVYGFAKS

      51                                                100
X-1   LLKALREDGD VVIVVFDAKA PSFRHQTYEA YKAGRAPTPE DFPRQLALIK
SM3   LLKALREDGD VVIVVFDAKA PSFRHQTYEA YKAGRAPTPE DFPRQLALIK
Vi7a  LLKALREDGD VVIVVFDAKA PSFRHQTYEA YKAGRAPTPE DFPRQLALIK

      101                                               150
X-1   EMVDLLGLER LEVPGFEADD VLATLAKKAE KEGYEVRILT ADRDLYQLLS
SM3   EMVDLLGLER LEVPGFEADD VLATLAKKAE KEGYEVRILT ADRDLYQLLS
Vi7a  EMVDLLGLER LEVPGFEADD VLATLAKKAE KEGYEVRILT ADRDLYQLLS

      151                                               200
X-1   ERISILHPEG YLITPEWLWE KYGLKPSQWV DYRALAGDPS DNIPGVKGIG
SM3   DRISILHPEG YLITPEWLWE KYGLKPSQWV DYRALAGDPS DNIPGVKGIG
Vi7a  DRISILHPEG YLITPEWLWE KYGLKPSQWV DYRALAGDPS DNIPGVKGIG

      201                                               250
X-1   EKTAAKLIRE WGSLENLLKH LEQVKPASVR EKILSHMEDL KLSLELSRVR
SM3   EKTAAKLIRE WGSLENLLKH LEQVKPASVR EKILSHMEDL KLSLELSRVH
Vi7a  EKTAAKLIRE WGSLENLLKH LEQVKPASVR EKILSHMEDL KLSLELSRVH

      251                                               300
X-1   TDLPLQVDFA RRREPDREGL KAFLERLEFG SLLHEFGLLE SPVAAEEAPW
SM3   TELPLQVDFA RRREPDREGL KAFLERLEFG SLLHEFGLLE SPVAAEEAPW
Vi7a  TELPLQVDFA RRREPDREGL KAFLERLEFG SLLHEFGLLE SPVAAEEAPW

      301                                               350
X-1   PPPEGAFVGY VLSRPEPMWA ELNALAAAWE GRVYRAEDPL EALRGLGEVR
SM3   PPPEGAFVGY VLSRPEPMWA ELNALAAAWE GRVYRAEDPL EALRGLGEVR
Vi7a  PPPEGAFVGY VLSRPEPMWA ELNALAAAWE GRVYRAEDPL EALRGLGEVR

      351                                               400
X-1   GLLAKDLAVL ALREGIALAP GDDPMLLAYL LDPSNTAPEG VARRYGGEWT
SM3   GLLAKDLAVL ALREGIALAQ GDDPMLLAYL LDPSNTAPEG VARRYGGEWT
Vi7a  GLLAKDLAVL ALREGIALAP GDDPMLLAYL LDPSNTAPEG VARRYGGEWT

      401                                               450
X-1   EEAGERALLS ERLYAALLER LKGEERLLWL YEEVEKPLSR VLAHMEATGV
SM3   EEAGERALLS ERLYAALLER LKGEERLLWL YEEVEKPLSR VLAHMEATGV
Vi7a  EEAGERALLS ERLYAALLER LKGEERLLWL YEEVEKPLSR VLAHMEATGV

      451                                               500
X-1   RLDVAYLKAL SLEVEAELRR LEEEVHRLAG HPFNLNSRDQ LERVLFDELG
SM3   WLDVAYLKAL SLEVEAELRR LEEEVHRLAG HPFNLNSRDQ LERVLFDELG
Vi7a  WLDVAYLKAL SLEVEAELRR LEEEVHRLAG HPFNLNSRDQ LERVLFDELG

      501                                               550
X-1   LPAIGKTEKT GKRSTSAAVL EALREAHPIV DRILQYRELS KLKGTYIDPL
SM3   LPAIGKTEKT GKRSTSAAVL EALREAHPIV DRILQYRELS KLKGTYIDPL
Vi7a  LPAIGKTEKT GKRSTSAAVL EALREAHPIV DRILQYRELS KLKGTYIDPL

      551                                               600
X-1   PALVHPKTNR LHTRFNQTAT ATGRLSSSDP NLQNIPVRTP LGQRIRRAFV
SM3   PALVHPKTNR LHTRFNQTAT ATGRLSSSDP NLQNIPVRTP LGQRIRRAFV
Vi7a  PALVHPKTNR LHTRFNQTAT ATGRLSSSDP NLQNIPVRTP LGQRIRRAFV

      601                                               650
X-1   AEEGWRLVVL DYSQIELRVL AHLSGDENLI RVFQEGQDIH TQTASWMFGV
SM3   AEEGWRLVVL DYSQIELRVL AHLSGDENLI RVFQEGQDIH TQTASWMFGV
Vi7a  AEEGWRLVVL DYSQIELRVL AHLSGDENLI RVFQEGQDIH TQTASWMFGV

      651                                               700
```

FIG. 2A

```
X-1   PPEAVDSLMR RAAKTINFGV LYGMSAHRLS GELAIPYEEA VAFIERYFQS
SM3   PPEAVDSLMR RAAKTINFGV LYGMSAHRLS GELAIPYEEA VAFIERYFQS
Vi7a  PPEAVDSLMR RAAKTINFGV LYGMSAHRLS GELAIPYEEA VAFIERYFQS

      701                                              750
X-1   YPKVRAWIEK TLAEGRERGY VETLFGRRRY VPDLASRVKS IREAAERMAF
SM3   YPKVRAWIEK TLAEGRERGY VETLFGRRRY VPDLASRVKS IREAAERMAF
Vi7a  YPKVRAWIEK TLAEGRERGY VETLFGRRRY VPDLASRVKS IREAAERMAF

      751                                              800
X-1   NMPVQGTAAD LMKLAMVKLF PRLQELGARM LLQVHDELVL EAPKEQAEEV
SM3   NMPVQGTAAD LMKLAMVKLF PRLQELGARM LLQVHDELVL EAPKEQAEEV
Vi7a  NMPVQGTAAD LMKLAMVKLF PRLQELGARM LLQVHDELVL EAPKEQAEEV

      801                                 833
X-1   AQEAKRTMEE VWPLKVPLEV EVGIGEDWLS AKA
SM3   AQEAKRTMEE VWPLKVPLEV EVGIGEDWLS AKA
Vi7a  AQEAKRTMEE VWPLKVPLEV EVGIGEDWLS AKA
```

FIG. 2B

*THERMUS SCOTODUCTUS* NUCLEIC ACID POLYMERASES

This application is a Divisional of U.S. application Ser. No. 10/799,369, filed on Mar. 12, 2004, now abandoned, which is a U.S. National Application filed under 35 U.S.C. §371 of International Application PCT/US2002/029102 filed Sep. 13, 2002, which claims the benefit of priority from U.S. Provisional Application No. 60/322,218, filed Sep. 14, 2001 and U.S. Provisional Application No. 60/334,489, filed Nov. 30, 2001, the disclosures of which are hereby incorporated by reference in their entirety as if set forth fully herein.

FIELD OF THE INVENTION

The invention relates to nucleic acids and polypeptides for nucleic acid polymerases from thermophilic strains of *Thermus scotoductus*.

BACKGROUND OF THE INVENTION

DNA polymerases are naturally-occurring intracellular enzymes used by a cell for replicating DNA by reading one nucleic acid strand and manufacturing its complement. Enzymes having DNA polymerase activity catalyze the formation of a bond between the 3' hydroxyl group at the growing end of a nucleic acid primer and the 5' phosphate group of a newly added nucleotide triphosphate. Nucleotide triphosphates used for DNA synthesis are usually deoxyadenosine triphosphate (A), deoxythymidine triphosphate (T), deoxycytosine triphosphate (C) and deoxyguanosine triphosphate (G), but modified or altered versions of these nucleotides can also be used. The order in which the nucleotides are added is dictated by hydrogen-bond formation between A and T nucleotide bases and between G and C nucleotide bases.

Bacterial cells contain three types of DNA polymerases, termed polymerase I, II and III. DNA polymerase I is the most abundant polymerase and is generally responsible for certain types of DNA repair, including a repair-like reaction that permits the joining of Okazaki fragments during DNA replication. Polymerase I is essential for the repair of DNA damage induced by UV irradiation and radiomimetic drugs. DNA Polymerase II is thought to play a role in repairing DNA damage that induces the SOS response. In mutants that lack both polymerase I and III, polymerase II repairs UV-induced lesions. Polymerase I and II are monomeric polymerases while polymerase III is a multisubunit complex.

Enzymes having DNA polymerase activity are often used in vitro for a variety of biochemical applications including cDNA synthesis and DNA sequencing reactions. See Sambrook e al., Molecular Cloning: A Laboratory Manual (3rd ed. Cold Spring Harbor Laboratory Press, 2001, hereby incorporated by reference. DNA polymerases are also used for amplification of nucleic acids by methods such as the polymerase chain reaction (PCR) (Mullis et al., U.S. Pat. Nos. 4,683,195, 4,683,202, and 4,800,159, incorporated by reference) and RNA transcription-mediated amplification methods (e.g., Kacian et al., PCT Publication No. WO91/01384, incorporated by reference).

DNA amplification utilizes cycles of primer extension through the use of a DNA polymerase activity, followed by thermal denaturation of the resulting double-stranded nucleic acid in order to provide a new template for another round of primer annealing and extension. Because the high temperatures necessary for strand denaturation result in the irreversible inactivations of many DNA polymerases, the discovery and use of DNA polymerases able to remain active at temperatures above about 37 EC provides an advantage in cost and labor efficiency.

Thermostable DNA polymerases have been discovered in a number of thermophilic organisms including *Thermus aquaticus, Thermus thermophilus*, and species within the genera the *Bacillus, Thermococcus, Sulfobus*, and *Pyrococcus*. A full length thermostable DNA polymerase derived from *Thermus aquaticus* (Taq) has been described by Lawyer, et al., J. Biol. Chem. 264:6427-6437 (1989) and Gelfand et al, U.S. Pat. No. 5,079,352. The cloning and expression of truncated versions of that DNA polymerase are further described in Lawyer et al., in PCR Methods and Applications, 2:275-287 (1993), and Barnes, PCT Publication No. WO92/06188 (1992). Sullivan reports the cloning of a mutated version of the Taq DNA polymerase in EPO Publication No. 0482714A1 (1992). A DNA polymerase from *Thermus thermophilus* has also been cloned and expressed. Asakura et al., J. Ferment. Bioeng. (Japan), 74:265-269 (1993). However, the properties of the various polymerases vary. Accordingly, new polymerases are needed that have improved sequence discrimination, better salt tolerance, combined reverse transcription and DNA polymerase activities, varying degrees of thermostability, improved tolerance for labeled or dideoxy nucleotides and other valuable properties.

SUMMARY OF THE INVENTION

The invention provides nucleic acid polymerase enzymes isolated from a thermophilic organism, *Thermus scotoductus*. The invention provides nucleic acid polymerases from several *Thermus scotoductus* strains including strain X-1 (ATCC Deposit No. 27978), strain SM3 and strain Vi7a.

In one embodiment, the invention provides an isolated nucleic acid encoding a *Thermus scotoductus* nucleic acid polymerase. Such a nucleic acid can have a polynucleotide sequence comprising any one of SEQ ID NO:1-12. Nucleic acids complementary to any one of SEQ ID NO:1-12 are also included within the invention. In another embodiment, the invention provides an isolated nucleic acid encoding a polypeptide having at least 93% identity to an amino acid sequence comprising any one of SEQ ID NO:13-28. The invention also provides vectors comprising these isolated nucleic acids, including expression vectors comprising a promoter operably linked to any of the isolated nucleic acids of the invention. Host cells comprising such isolated nucleic acids and vectors are also provided by the invention, particularly host cells capable of expressing a thermostable polypeptide, where the polypeptide has nucleic acid polymerase or DNA polymerase activity.

In another embodiment, the invention provides an isolated nucleic acid encoding a derivative nucleic acid polymerase comprising any one of amino acid sequences SEQ ID NO:13-16 having a mutation that decreases 5-3' exonuclease activity. Such a derivative nucleic acid polymerase has decreased 5-3' exonuclease activity relative to a nucleic acid polymerase comprising any one of amino acid sequences SEQ ID NO:13-16.

In another embodiment, the invention provides an isolated nucleic acid encoding a derivative nucleic acid polymerase comprising any one of amino acid sequences SEQ ID NO:13-16 having a mutation that reduces discrimination against dideoxynucleotide triphosphates. Such a derivative nucleic acid polymerase has reduced discrimination against dideoxynucleotide triphosphates relative to a nucleic acid polymerase comprising any one of amino acid sequences SEQ ID NO:13-16.

The invention also provides isolated polypeptides that can include an amino acid sequence with at least 93% identity to any one of SEQ ID NO:13-28. The isolated polypeptides provided by the invention preferably have an amino acid sequence with at least 95% sequence identity to any one of SEQ ID NO:13-28. Such polypeptides can also have nucleic acid polymerase or DNA polymerase activity. Such DNA polymerase activity can, for example, be about 50,000 U/mg protein to about 500,000 U/mg protein.

The invention further provides a method of synthesizing DNA that includes contacting a polypeptide comprising any one of SEQ ID NO:13-28 with a DNA under conditions sufficient to permit polymerization of DNA.

The invention also provides a method of synthesizing DNA from an RNA template that includes contacting a polypeptide comprising any one of SEQ ID NO:13-28 with an RNA template under conditions sufficient to permit synthesis of DNA (e.g. reverse transcription). The invention further provides a method for thermocyclic amplification of nucleic acid that comprises contacting a nucleic acid with a thermostable polypeptide having any one of SEQ ID NO:13-28 under conditions suitable for amplification of the nucleic acid, and amplifying the nucleic acid. Such amplification can be, for example, by Strand Displacement Amplification or Polymerase Chain Reaction.

The invention also provides a method of primer extending DNA comprising contacting a polypeptide comprising of SEQ ID NO:13-28 with a DNA under conditions sufficient to permit polymerization of DNA. Such primer extension can be performed, for example, to sequence DNA or to amplify DNA.

The invention further provides a method of making a nucleic acid polymerase comprising any one of SEQ ID NO:13-28, the method comprising incubating a host cell comprising a nucleic acid that encodes a polypeptide comprising any one of SEQ ID NO:13-28, operably linked to a promoter under conditions sufficient for RNA transcription and translation. In one embodiment, the method uses a nucleic acid that comprises any one of SEQ ID NO:1-12. The invention is also directed to a nucleic acid polymerase or DNA polymerase made by this method.

The invention also provides a kit that includes a container containing a nucleic acid polymerase comprising an amino acid sequence with at least 93% identity to any one of SEQ ID NO:13-28. The kit can also contain an unlabeled nucleotide, a labeled nucleotide, a balanced mixture of nucleotides, a chain terminating nucleotide, a nucleotide analog, a buffer solution, a solution containing magnesium, a cloning vector, a restriction endonuclease, a sequencing primer, a solution containing reverse transcriptase, or a DNA or RNA amplification primer. Such kits can, for example, be adapted for performing DNA sequencing, DNA amplification, RNA amplification, reverse transcription or primer extension reactions.

DESCRIPTION OF THE FIGURES

FIG. 1 provides a comparison of amino acid sequences for polymerases from *Thermus aquaticus* (Taq; SEQ ID NO:48), *Thermus thermophilus* (Tth; SEQ ID NO:49), *Thermus filiformis* (Tfi; SEQ ID NO:50) and strain X-1 *Thermus scotoductus* strain X-1 (Tsc; SEQ ID NO:13).

FIG. 2 provides a comparison of amino acid sequences for three strains of *Thermus scotoductus* polymerases: strain X-1 (SEQ ID NO:13), strain SM3 (SEQ ID NO:15), and strain Vi7a (SEQ ID NO:16).

DETAILED DESCRIPTION OF THE INVENTION

The present invention relates to nucleic acid and amino acid sequences encoding nucleic acid polymerases from thermophilic organisms. In particular, the present invention provides a nucleic acid polymerase from *Thermus scotoductus*. The nucleic acid polymerases of the invention can be used in a variety of procedures, including DNA synthesis, reverse transcription, DNA primer extension, DNA sequencing and DNA amplification procedures.

DEFINITIONS

The term "amino acid sequence" refers to the positional arrangement and identity of amino acids in a peptide, polypeptide or protein molecule. Use of the term "amino acid sequence" is not meant to limit the amino acid sequence to the complete, native amino acid sequence of a peptide, polypeptide or protein.

"Chimeric" is used to indicate that a nucleic acid, such as a vector or a gene, is comprised of more than one nucleic acid segment and that at least two nucleic acid segments are of distinct origin. Such nucleic acid segments are fused together by recombinant techniques resulting in a nucleic acid sequence, which does not occur naturally.

The term "coding region" refers to the nucleotide sequence that codes for a protein of interest. The coding region of a protein is bounded on the 5' side by the nucleotide triplet "ATG" that encodes the initiator methionine and on the 3' side by one of the three triplets that specify stop codons (i.e., TAA, TAG, TGA).

"Constitutive expression" refers to expression using a constitutive promoter.

"Constitutive promoter" refers to a promoter that is able to express the gene that it controls in all, or nearly all, phases of the life cycle of the cell.

"Complementary" or "complementarity" are used to define the degree of base-pairing or hybridization between nucleic acids. For example, as is known to one of skill in the art, adenine (A) can form hydrogen bonds or base pair with thymine (T) and guanine (G) can form hydrogen bonds or base pair with cytosine (C). Hence, A is complementary to T and G is complementary to C. Complementarity may be complete when all bases in a double-stranded nucleic acid are base paired. Alternatively, complementarity may be "partial," in which only some of the bases in a nucleic acid are matched according to the base pairing rules. The degree of complementarity between nucleic acid strands has an effect on the efficiency and strength of hybridization between nucleic acid strands.

The "derivative" of a reference nucleic acid, protein, polypeptide or peptide, is a nucleic acid, protein, polypeptide or peptide, respectively, with a related but different sequence or chemical structure than the respective reference nucleic acid, protein, polypeptide or peptide. A derivative nucleic acid, protein, polypeptide or peptide is generally made purposefully to enhance or incorporate some chemical, physical or functional property that is absent or only weakly present in the reference nucleic acid, protein, polypeptide or peptide. A derivative nucleic acid generally can differ in nucleotide sequence from a reference nucleic acid whereas a derivative protein, polypeptide or peptide can differ in amino acid sequence from the reference protein, polypeptide or peptide, respectively. Such sequence differences can be one or more substitutions, insertions, additions, deletions, fusions and truncations, which can be present in any combination. Differences can be minor (e.g., a difference of one nucleotide or amino acid) or more substantial. However, the sequence of the derivative is not so different from the reference that one of skill in the art would not recognize that the derivative and reference are related in structure and/or function. Generally, differences are limited so that the reference and the derivative are closely similar overall and, in many regions, identical. A “variant” differs from a “derivative” nucleic acid, protein, polypeptide or peptide in that the variant can have silent structural differences that do not significantly change the chemical, physical or functional properties of the reference nucleic acid, protein, polypeptide or peptide. In contrast, the differences between the reference and derivative nucleic acid, protein, polypeptide or peptide are intentional changes made to improve one or more chemical, physical or functional properties of the reference nucleic acid, protein, polypeptide or peptide.

The terms “DNA polymerase activity,” “synthetic activity” and “polymerase activity” are used interchangeably and refer to the ability of an enzyme to synthesize new DNA strands by the incorporation of deoxynucleoside triphosphates. A protein that can direct the synthesis of new DNA strands by the incorporation of deoxynucleoside triphosphates in a template-dependent manner is said to be “capable of DNA synthetic activity.”

The term “5' exonuclease activity” refers to the presence of an activity in a protein that is capable of removing nucleotides from the 5' end of a nucleic acid.

The term “3' exonuclease activity” refers to the presence of an activity in a protein that is capable of removing nucleotides from the 3' end of a nucleic acid.

“Expression” refers to the transcription and/or translation of an endogenous or exogeneous gene in an organism. Expression generally refers to the transcription and stable accumulation of mRNA. Expression may also refer to the production of protein.

“Expression cassette” means a nucleic acid sequence capable of directing expression of a particular nucleotide sequence. Expression cassettes generally comprise a promoter operably linked to the nucleotide sequence to be expressed (e.g., a coding region) that is operably linked to termination signals. Expression cassettes also typically comprise sequences required for proper translation of the nucleotide sequence. The expression cassette comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term “gene” is used broadly to refer to any segment of nucleic acid associated with a biological function. The term “gene” encompasses the coding region of a protein, polypeptide, peptide or structural RNA. The term “gene” also includes sequences up to a distance of about 2 kb on either end of a coding region. These sequences are referred to as “flanking” sequences or regions (these flanking sequences are located 5' or 3' to the non-translated sequences present on the mRNA transcript). The 5' flanking region may contain regulatory sequences such as promoters and enhancers or other recognition or binding sequences for proteins that control or influence the transcription of the gene. The 3' flanking region may contain sequences that direct the termination of transcription, post-transcriptional cleavage and polyadenylation as well as recognition sequences for other proteins. A protein or polypeptide encoded in a gene can be full length or any portion thereof, so that all activities or functional properties are retained, or so that only selected activities (e.g., enzymatic activity, ligand binding, or signal transduction) of the full-length protein or polypeptide are retained. The protein or polypeptide can include any sequences necessary for the production of a proprotein or precursor polypeptide. The term “native gene” refers to gene that is naturally present in the genome of an untransformed cell.

“Genome” refers to the complete genetic material that is naturally present in an organism and is transmitted from one generation to the next.

The terms “heterologous nucleic acid,” or “exogenous nucleic acid” refer to a nucleic acid that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring nucleic acid. Thus, the terms refer to a nucleic acid segment that is foreign or heterologous to the cell, or normally found within the cell but in a position within the cell or genome where it is not ordinarily found.

The term “homology” refers to a degree of similarity between a nucleic acid and a reference nucleic acid or between a polypeptide and a reference polypeptide. Homology may be partial or complete. Complete homology indicates that the nucleic acid or amino acid sequences are identical. A partially homologous nucleic acid or amino acid sequence is one that is not identical to the reference nucleic acid or amino acid sequence. Hence, a partially homologous nucleic acid has one or more nucleotide differences in its sequence relative to the nucleic acid to which it is being compared. The degree of homology can be determined by sequence comparison. Alternatively, as is understood by those skilled in the art, DNA-DNA or DNA-RNA hybridization, under various hybridization conditions, can provide an estimate of the degree of homology between nucleic acids, (see, e.g., Haines and Higgins (eds.), Nucleic Acid Hybridization, IRL Press, Oxford, U.K.).

“Hybridization” refers to the process of annealing complementary nucleic acid strands by forming hydrogen bonds between nucleotide bases on the complementary nucleic acid strands. Hybridization, and the strength of the association between the nucleic acids, is impacted by such factors as the degree of complementary between the hybridizing nucleic acids, the stringency of the conditions involved, the $T_m$ of the formed hybrid, and the G:C ratio within the nucleic acids.

“Inducible promoter” refers to a regulated promoter that can be turned on in one or more cell types by an external stimulus, such as a chemical, light, hormone, stress, temperature or a pathogen.

An “initiation site” is region surrounding the position of the first nucleotide that is part of the transcribed sequence, which is defined as position +1. All nucleotide positions of the gene are numbered by reference to the first nucleotide of the transcribed sequence, which resides within the initiation site. Downstream sequences (i.e., sequences in the 3' direction) are denominated positive, while upstream sequences (i.e., sequences in the 5' direction) are denominated negative.

An “isolated” or “purified” nucleic acid or an “isolated” or “purified” polypeptide is a nucleic acid or polypeptide that, by the hand of man, exists apart from its native environment and is therefore not a product of nature. An isolated nucleic acid or polypeptide may exist in a purified form or may exist in a non-native environment such as, for example, a transgenic host cell.

The term “invader oligonucleotide” refers to an oligonucleotide that contains sequences at its 3' end that are substantially the same as sequences located at the 5' end of a probe oligonucleotide. These regions will compete for hybridization to the same segment along a complementary target nucleic acid.

The term “label” refers to any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like.

The term “nucleic acid” refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term “oligonucleotide” as used herein is defined as a molecule comprised of two or more deoxyribonucleotides or ribonucleotides, preferably more than three, and usually more than ten. There is no precise upper limit on the size of an oligonucleotide. However, in general, an oligonucleotide is shorter than about 250 nucleotides, preferably shorter than about 200 nucleotides and more preferably shorter than about 100 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

The terms “open reading frame” and “ORF” refer to the amino acid sequence encoded between translation initiation and termination codons of a coding sequence. The terms “initiation codon” and “termination codon” refer to a unit of three adjacent nucleotides (‘codon’) in a coding sequence that specifies initiation and chain termination, respectively, of protein synthesis (mRNA translation).

“Operably linked” means joined as part of the same nucleic acid molecule, so that the function of one is affected by the other. In general, “operably linked” also means that two or more nucleic acids are suitably positioned and oriented so that they can function together. Nucleic acids are often operably linked to permit transcription of a coding region to be initiated from the promoter. For example, a regulatory sequence is said to be “operably linked to” or “associated with” a nucleic acid sequence that codes for an RNA or a polypeptide if the two sequences are situated such that the regulatory sequence affects expression of the coding region (i.e., that the coding sequence or functional RNA is under the transcriptional control of the promoter). Coding regions can be operably-linked to regulatory sequences in sense or antisense orientation.

The term “probe oligonucleotide” refers to an oligonucleotide that interacts with a target nucleic acid to form a cleavage structure in the presence or absence of an invader oligonucleotide. When annealed to the target nucleic acid, the probe oligonucleotide and target form a cleavage structure and cleavage occurs within the probe oligonucleotide. The presence of an invader oligonucleotide upstream of the probe oligonucleotide can shift the site of cleavage within the probe oligonucleotide (relative to the site of cleavage in the absence of the invader).

“Promoter” refers to a nucleotide sequence, usually upstream (5') to a coding region, which controls the expression of the coding region by providing the recognition site for RNA polymerase and other factors required for proper transcription. “Promoter” includes but is not limited a minimal promoter that is a short DNA sequence comprised of a TATA-box. Hence, a promoter includes other sequences that serve to specify the site of transcription initiation and control or regulate expression, for example, enhancers. Accordingly, an “enhancer” is a segment of DNA that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Promoters may be derived in their entirety from a native gene, or be composed of different elements derived from different promoters found in nature, or even be comprised of synthetic DNA segments. A promoter may also contain DNA segments that are involved in the binding of protein factors that control the effectiveness of transcription initiation in response to physiological or developmental conditions.

The terms “protein,” “peptide” and “polypeptide” are used interchangeably herein.

“Regulatory sequences” and “regulatory elements” refer to nucleotide sequences that control some aspect of the expression of nucleic acid sequences. Such sequences or elements can be located upstream (5' non-coding sequences), within, or downstream (3' non-coding sequences) of a coding sequence. “Regulatory sequences” and “regulatory elements” influence the transcription, RNA processing or stability, or translation of the associated coding sequence. Regulatory sequences include enhancers, introns, promoters, polyadenylation signal sequences, splicing signals, termination signals, and translation leader sequences. They include natural and synthetic sequences.

As used herein, the term “selectable marker” refers to a gene that encodes an observable or selectable trait that is expressed and can be detected in an organism having that gene. Selectable markers are often linked to a nucleic acid of interest that may not encode an observable trait, in order to trace or select the presence of the nucleic acid of interest. Any selectable marker known to one of skill in the art can be used with the nucleic acids of the invention. Some selectable markers allow the host to survive under circumstances where, without the marker, the host would otherwise die. Examples of selectable markers include antibiotic resistance, for example, tetracycline or ampicillin resistance.

As used herein the term “stringency” is used to define the conditions of temperature, ionic strength, and the presence of other compounds such as organic solvents, under which nucleic acid hybridizations are conducted. With “high stringency” conditions, nucleic acid base pairing will occur only between nucleic acids that have a high frequency of complementary base sequences. With “weak” or “low” stringency conditions nucleic acids the frequency of complementary sequences is usually less, so that nucleic acids with differing sequences can be detected and/or isolated.

The terms “substantially similar” and “substantially homologous” refer to nucleotide and amino acid sequences that represent functional equivalents of the instant inventive sequences. For example, altered nucleotide sequences that simply reflect the degeneracy of the genetic code but nonetheless encode amino acid sequences that are identical to the inventive amino acid sequences are substantially similar to the inventive sequences. In addition, amino acid sequences that are substantially similar to the instant sequences are those wherein overall amino acid identity is sufficient to provide an active, thermally stable nucleic acid polymerase. For example, amino acid sequences that are substantially similar to the sequences of the invention are those wherein the overall amino acid identity is 80% or greater, preferably 90% or greater, such as 91%, 92%, 93%, or 94%, and more preferably 95% or greater, such as 96%, 97%, 98%, or 99% relative to the amino acid sequences of the invention.

A "terminating agent," "terminating nucleotide" or "terminator" in relation to DNA synthesis or sequencing refers to compounds capable of specifically terminating a DNA sequencing reaction at a specific base, such compounds include but are not limited to, dideoxynucleosides having a 2',3' dideoxy structure (e.g., ddATP, ddCTP, ddGTP and ddTTP).

"Thermostable" means that a nucleic acid polymerase remains active at a temperature greater than about 37 EC. Preferably, the nucleic acid polymerases of the invention remain active at a temperature greater than about 42 EC. More preferably, the nucleic acid polymerases of the invention remain active at a temperature greater than about 50 EC. Even more preferably, the nucleic acid polymerases of the invention remain active after exposure to a temperature greater than about 60 EC. Most preferably, the nucleic acid polymerases of the invention remain active despite exposure to a temperature greater than about 70 EC.

A "transgene" refers to a gene that has been introduced into the genome by transformation and is stably maintained. Transgenes may include, for example, genes that are either heterologous or homologous to the genes of a particular organism to be transformed. Additionally, transgenes may comprise native genes inserted into a non-native organism, or chimeric genes. The term "endogenous gene" refers to a native gene in its natural location in the genome of an organism. A "foreign" or "exogenous" gene refers to a gene not normally found in the host organism but one that is introduced by gene transfer.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms." Transformation may be accomplished by a variety of means known to the art including calcium DNA co-precipitation, electroporation, viral infection, and the like.

The "variant" of a reference nucleic acid, protein, polypeptide or peptide, is a nucleic acid, protein, polypeptide or peptide, respectively, with a related but different sequence than the respective reference nucleic acid, protein, polypeptide or peptide. The differences between variant and reference nucleic acids, proteins, polypeptides or peptides are silent or conservative differences. A variant nucleic acid differs in nucleotide sequence from a reference nucleic acid whereas a variant nucleic acid, protein, polypeptide or peptide differs in amino acid sequence from the reference protein, polypeptide or peptide, respectively. A variant and reference nucleic acid, protein, polypeptide or peptide may differ in sequence by one or more substitutions, insertions, additions, deletions, fusions and truncations, which may be present in any combination. Differences can be minor (e.g., a difference of one nucleotide or amino acid) or more substantial. However, the structure and function of the variant is not so different from the reference that one of skill in the art would not recognize that the variant and reference are related in structure and/or function. Generally, differences are limited so that the reference and the variant are closely similar overall and, in many regions, identical.

The term "vector" is used to refer to a nucleic acid that can transfer another nucleic acid segment(s) into a cell. A "vector" includes, inter alia, any plasmid, cosmid, phage or nucleic acid in double- or single-stranded, linear or circular form that may or may not be self transmissible or mobilizable. It can transform prokaryotic or eukaryotic host cells either by integration into the cellular genome or by existing extrachromosomally (e.g., autonomous replicating plasmid with an origin of replication). Vectors used in bacterial systems often contain an origin of replication that allows the vector to replicate independently of the bacterial chromosome. The term "expression vector" refers to a vector containing an expression cassette.

The term "wild-type" refers to a gene or gene product that has the characteristics of that gene or gene product when isolated from a naturally occurring source. A wild-type gene is the gene form most frequently observed in a population and thus arbitrarily is designed the "normal" or "wild-type" form of the gene. In contrast, the term "variant" or "derivative" refers to a gene or gene product that displays modifications in sequence and or functional properties (i.e., altered characteristics) when compared to the wild-type gene or gene product. Naturally-occurring derivatives can be isolated. They are identified by the fact that they have altered characteristics when compared to the wild-type gene or gene product.

Polymerase Nucleic Acids

The invention provides isolated nucleic acids encoding *Thermus scotoductus* nucleic acid polymerases as well as derivatives fragments and variant nucleic acids thereof that encode an active, thermally stable nucleic acid polymerase. Thus, one aspect of the invention includes the nucleic acid polymerases encoded by the polynucleotide sequences contained in *Thermus scotoductus* strain X-1 (ATCC Deposit No. 27978). Another aspect of the invention provides the nucleic acid polymerases of *Thermus scotoductus* strains SM3 and Vi7a. Any nucleic acid encoding any one of amino acid sequences SEQ ID NO:13-28, which are amino acid sequences for wild type and several derivative *Thermus scotoductus* nucleic acid polymerases, are also contemplated by the present invention.

In one embodiment, the invention provides a nucleic acid of SEQ ID NO:1, a wild type *Thermus scotoductus*, strain X-1, nucleic acid encoding a nucleic acid polymerase.

```
ATGAGGGCGA TGCTGCCCCT CTTTGAGCCC AAGGGCCGGG    40
TGCTTCTGGT GGACGGCCAC CACCTGGCCT ACCGTACCTT    80
TTTTGCCCTG AAGGGCCTCA CCACCAGCCG CGGGGAGCCG   120
GTCCAGGCGG TGTACGGGTT TGCCAAGAGC CTTTTGAAGG   160
CGCTAAGGGA AGACGGGGAT GTGGTGATCG TGGTGTTTGA   200
CGCCAAGGCC CCCTCCTTCC GCCACCAGAC CTACGAGGCC   240
TACAAGGCGG GGCGGGCTCC CACCCCCGAG GACTTTCCCC   280
GGCAGCTTGC CCTTATCAAG GAGATGGTGG ACCTTTTGGG   320
CCTGGAGCGC CTCGAGGTGC CGGGCTTTGA GGCGGATGAC   360
```

-continued

GTCCTGGCTA CCCTGGCCAA GAAGGCGGAA AAGGAAGGCT 400

ACGAGGTGCG CATCCTCACC GCGGACCGGG ACCTTTACCA 440

GCTTCTTTCG GAGCGAATCT CCATCCTTCA CCCGGAGGGT 480

TACCTGATCA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTATC CCGGGTGCGC ACGGACTTGC 760

CCCTTCAGGT GGACTTCGCC CGGCGCCGGG AGCCGGACCG 800

GGAGGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

ACCGGGCGGA GGATCCCTTG GAGGCCTTGC GGGGGCTTGG 1040

GGAGGTGAGG GGGCTTTTGG CCAAGGACCT GGCGGTGCTG 1080

GCCCTGAGGG AAGGGATTGC CCTGGCACCG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GTTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA CGGTTGGATG 1360

TGGCCTACTT AAAGGCCCTT TCCCTGGAGG TGGAGGCGGA 1400

GCTCAGGCGC CTCGAGGAGG AGGTCCACCG CCTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGCAAGCGCT CCACCAGCGC CGCCGTTTTG 1560

GAGGCCTTGC GGGAGGCTCA TCCCATCGTG GACCGCATCC 1600

TTCAGTACCG GGAGCTTTCC AAGCTCAAGG GAACCTACAT 1640

CGATCCCTTG CCTGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTGGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTAATC CGGGTCTTCC AGGAGGGCCA GGACATCCAC 1920

ACCCAGACGG CCAGCTGGAT GTTCGGCGTG CCCCCAGAGG 1960

-continued

CCGTGGATTC CCTGATGCGT CGGGCGGCCA AGACCATCAA 2000

CTTCGGCGTC CTCTACGGCA TGTCCGCCCA CCGGCTTTCG 2040

GGAGAGCTGG CCATCCCCTA CGAGGAGGCG GTGGCCTTCA 2080

TCGAGCGGTA TTTCCAGAGC TACCCCAAGG TGCGGGCCTG 2120

GATTGAGAAA ACCCTGGCGG AAGGACGGGA ACGGGGCTAT 2160

GTGGAAACCC TCTTTGGCCG CCGGCGCTAC GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAAGTGGGCA TCGGGGAGGA 2480

CTGGCTTTCC GCCAAGGCCT AG 2502

In another embodiment, the invention provides nucleic acids encoding a wild type nucleic acid polymerase from *Thermus scotoductus*, strain SM3, having, for example, SEQ ID NO:2.

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGGGTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAAGTGC CGGGTTTTGA GGCGGATGAC 360

GTCCTGGCCA CCCTGGCCAA GAAGGCGGAA AAGGAAGGCT 400

ACGAGGTGCG CATCCTCACC GCGGACCGGG ACCTTTACCA 440

GCTTCTTTCG GACCGAATCT CCATCCTTCA CCCGGAGGGT 480

TACCTGATCA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTTTC CCGGGTGCAC ACGGAGTTGC 760

CCCTTCAGGT GGACTTCGCC CGGCGCCGGG AGCCGGACCG 800

GGAAGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

-continued

```
CGTGGGGTAC GTTCTTTCCC GCCCCGAGCC CATGTGGGCG     960
GAGCTTAACG CCTTGGCCGC CGCCTGGGAG GGAAGGGTTT    1000
ACCGGGCGGA GGATCCCTTG GAGGCCTTGC GGGGGCTTGG    1040
GGAGGTGAGG GGGCTTTTGG CCAAGGACCT GGCGGTGCTG    1080
GCCCTGAGGG AAGGGATTGC CCTGGCACAG GGCGACGACC    1120
CCATGCTCCT CGCCTACCTC CTGGATCCTT CCAACACCGC    1160
CCCCGAAGGG GTAGCCCGGC GCTACGGGGG GGAGTGGACC    1200
GAGGAGGCGG GGGAAAGGGC GCTGCTTTCC GAAAGGCTTT    1240
ACGCCGCCCT CCTGGAGCGG CTTAAGGGGG AGGAGAGGCT    1280
TCTTTGGCTT TACGAGGAGG TGGAAAAGCC CCTTTCGCGG    1320
GTCCTGGCCC ACATGGAGGC CACGGGGGTA TGGTTGGATG    1360
TGGCCTACTT GAAGGCCCTT TCCCTGGAGG TGGAGGCGGA    1400
GCTCAGGCGC CTCGAGGAGG AGGTCCACCG ACTGGCCGGG    1440
CATCCTTTCA ACCTGAACTC CCGGGACCAG CTGGAAAGGG    1480
TCCTCTTTGA CGAGCTTGGG CTTCCCGCCA TCGGCAAGAC    1520
GGAGAAGACG GGTAAGCGTT CCACCAGCGC CGCCGTTTTG    1560
GAGGCTTTGA GGGAGGCTCA TCCCATAGTG GACCGCATCC    1600
TCCAGTACCG GGAGCTTTCC AAGCTCAAGG GAACGTACAT    1640
CGATCCCTTG CCCGCCCTGG TCCACCCCAA GACGAACCGC    1680
CTCCACACCC GTTTCAACCA GACGGCCACC GCCACGGGGA    1720
GGCTTAGCAG CTCGGATCCC AACCTGCAAA ATATCCCCGT    1760
GCGCACCCCT TTAGGCCAGC GGATCCGCCG GGCCTTCGTG    1800
GCCGAGGAGG GGTGGAGGCT GGTGGTTTTG GACTACAGCC    1840
AGATTGAGCT CAGGGTCCTG GCGCACCTTT CCGGGGACGA    1880
GAACCTGATC CGGGTCTTCC AAGAGGGCCA GGACATCCAC    1920
ACCCAGACGG CCAGCTGGAT GTTCGGCGTG CCCCCAGAGG    1960
CCGTGGATTC CCTGATGCGC CGGGCGGCCA AGACCATCAA    2000
CTTCGGCGTC CTCTACGGCA TGTCCGCCCA CCGGCTTTCG    2040
GGAGAGCTGG CCATCCCCTA CGAGGAAGCG GTGGCCTTCA    2080
TCGAGCGGTA TTTCCAGAGC TACCCCAAGG TACGGGCCTG    2120
GATTGAGAAA ACCCTGGCGG AAGGACGGGA GCGGGGCTAT    2160
GTGGAAACCC TCTTTGGCCG CCGGCGCTAT GTGCCCGACT    2200
TGGCTTCCCG GGTGAAGAGC ATCCGGGAGG CAGCGGAGCG    2240
CATGGCCTTC AACATGCCGG TCCAGGGGAC CGCCGCGGAT    2280
TTGATGAAAC TGGCCATGGT GAAGCTCTTT CCCAGGCTTC    2320
AGGAGCTGGG GGCCAGGATG CTTTTGCAGG TGCACGACGA    2360
ACTGGTCCTC GAGGCTCCCA AGGAGCAAGC GGAGGAAGTC    2400
GCCCAGGAGG CCAAGCGGAC CATGGAGGAG GTGTGGCCCC    2440
TGAAGGTGCC CTTGGAGGTG GAGGTGGGTA TCGGGGAGGA    2480
CTGGCTTTCC GCCAAGGCCT AGTCGAC                  2507
```

In another embodiment, the invention provides nucleic acids encoding a wild type nucleic acid polymerase from *Thermus scotoductus*, strain Vi7a, having, for example, SEQ ID NO:3.

```
ATGAGGGCGA TGCTGCCCCT CTTTGAGCCC AAGGGCCGGG      40
TGCTTCTGGT GGACGGCCAC CACCTGGCCT ACCGTACCTT      80
TTTTGCCCTG AAGGGCCTCA CCACCAGCCG CGGGGAGCCG     120
GTCCAGGCGG TGTACGGGTT TGCCAAGAGC CTTTTGAAGG     160
CGCTAAGGGA AGACGGGGAT GTGGTGATCG TGGTGTTTGA     200
CGCCAAGGCC CCCTCCTTCC GCCACCAGAC CTACGAGGCC     240
TACAAGGCGG GGCGGGCTCC CACCCCCGAG GACTTTCCCC     280
GGCAGCTTGC CCTTATCAAG GAGATGGTGG ACCTTTTGGG     320
CCTGGAGCGC CTCGAAGTGC CGGGTTTTGA GGCGGATGAC     360
GTCCTGGCCA CCCTGGCCAA GAAGGCGGAA AAGGAAGGCT     400
ACGAGGTGCG CATCCTCACC GCGGACCGGG ACCTTTACCA     440
GCTTCTTTCG GACCGAATCT CCATCCTTCA CCCGGAGGGT     480
TACCTGATTA CCCCGGAGTG GCTTTGGGAG AAGTATGGGC     520
TTAAGCCTTC CCAGTGGGTG GACTACCGGG CCTTGGCCGG     560
GGACCCTTCC GACAACATCC CCGGCGTGAA GGGCATCGGG     600
GAGAAGACGG CGGCCAAGCT GATCCGGGAG TGGGGAAGCC     640
TGGAAAACCT TCTTAAGCAC CTGGAACAGG TGAAACCTGC     680
CTCCGTGCGG GAGAAGATCC TTAGCCACAT GGAGGACCTC     720
AAGCTATCCC TGGAGCTTTC CCGGGTGCAC ACGGAGTTGC     760
CCCTTCAGGT GGACTTCGCC CGGCGCCGGG AGCCGGACCG     800
GGAAGGGCTT AAGGCCTTTT TGGAGAGGCT GGAGTTCGGA     840
AGCCTCCTCC ACGAGTTCGG CCTGTTGGAA AGCCCGGTGG     880
CGGCGGAGGA AGCTCCCTGG CCGCCCCCCG AGGGAGCCTT     920
CGTGGGGTAC GTTCTTTCCC GCCCCGAGCC CATGTGGGCG     960
GAGCTTAACG CCTTGGCCGC CGCCTGGGAG GGAAGGGTTT    1000
ACCGGGCGGA GGATCCCTTG GAGGCCTTGC GGGGGCTTGG    1040
GGAGGTGAGG GGGCTTTTGG CCAAGGACCT GGCGGTGCTG    1080
GCCCTGAGGG AAGGGATTGC CCTGGCACCG GGCGACGACC    1120
CCATGCTCCT CGCCTACCTC CTGGATCCTT CCAACACCGC    1160
CCCCGAAGGG GTAGCCCGGC GCTACGGGGG GGAGTGGACC    1200
GAGGAGGCGG GGGAAAGGGC GCTGCTTTCC GAAAGGCTTT    1240
ACGCCGCCCT CCTGGAGCGG CTTAAGGGGG AGGAGAGGCT    1280
TCTTTGGCTT TACGAGGAGG TGGAAAAGCC CCTTTCGCGG    1320
GTCCTGGCCC ACATGGAGGC CACGGGGGTA TGGTTGGATG    1360
TGGCCTACTT GAAGGCCCTT TCCCTGGAGG TGGAGGCGGA    1400
GCTCAGGCGC CTCGAGGAGG AGGTCCACCG ACTGGCCGGG    1440
CATCCTTTCA ACCTGAACTC CCGGGACCAG CTGGAAAGGG    1480
TCCTCTTTGA CGAGCTTGGG CTTCCCGCCA TCGGCAAGAC    1520
```

-continued

GGAGAAGACG GGTAAGCGTT CCACCAGCGC CGCCGTTTTG 1560

GAGGCTTTGA GGGAGGCTCA TCCCATAGTG GACCGCATCC 1600

TCCAGTACCG GGAGCTTTCC AAGCTCAAGG GAACGTACAT 1640

CGATCCCTTG CCCGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTAGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTGATC CGGGTCTTCC AAGAGGGCCA GGACATCCAC 1920

ACCCAGACGG CCAGCTGGAT GTTCGGCGTG CCCCCAGAGG 1960

CCGTGGATTC CCTGATGCGC CGGGCGGCCA AGACCATCAA 2000

CTACGGCGTC CTCTACGGCA TGTCCGCCCA CCGGCTTTCG 2040

GGAGAGCTGG CCATCCCCTA CGAGGAAGCG GTGGCCTTCA 2080

TCGAGCGGTA TTTCCAGAGC TTCCCCAAGG TACGGGCCTG 2120

GATTGAGAAA ACCCTGGCGG AAGGACGGGA GCGGGGCTAT 2160

GTGGAAACCC TCTTTGGCCG CCGGCGCTAT GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAGGTGGGTA TCGGGGAGGA 2480

CTGGCTTTCC GCCAAGGCCT AGTCGAC 2507

In another embodiment, the invention provides a nucleic acid of SEQ ID NO:4, a derivative nucleic acid related to *Thermus scotoductus*, strain X-1, having GAC (encoding Asp) in place of GGG (encoding Gly) at positions 136-138. SEQ ID NO:4 is provided below.

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGACTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAGGTGC CGGGCTTTGA GGCGGATGAC 360

GTCCTGGCTA CCCTGGCCAA GAAGGCGGAA AAGGAAGGCT 400

ACGAGGTGCG CATCCTCACC GCGGACCGGG ACCTTTACCA 440

-continued

GCTTCTTTCG GAGCGAATCT CCATCCTTCA CCCGGAGGGT 480

TACCTGATCA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTATC CCGGGTGCGC ACGGACTTGC 760

CCCTTCAGGT GGACTTCGCC CGGCGCCGGG AGCCGGACCG 800

GGAGGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

ACCGGGCGGA GGATCCCTTG GAGGCCTTGC GGGGGCTTGG 1040

GGAGGTGAGG GGGCTTTTGG CCAAGGACCT GGCGGTGCTG 1080

GCCCTGAGGG AAGGGATTGC CCTGGCACCG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GTTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA CGGTTGGATG 1360

TGGCCTACTT AAAGGCCCTT TCCCTGGAGG TGGAGGCGGA 1400

GCTCAGGCGC CTCGAGGAGG AGGTCCACCG CCTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGCAAGCGCT CCACCAGCGC CGCCGTTTTG 1560

GAGGCCTTGC GGGAGGCTCA TCCCATCGTG GACCGCATCC 1600

TTCAGTACCG GGAGCTTTCC AAGCTCAAGG GAACCTACAT 1640

CGATCCCTTG CCTGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTGGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTAATC CGGGTCTTCC AGGAGGGCCA GGACATCCAC 1920

ACCCAGACGG CCAGCTGGAT GTTCGGCGTG CCCCCAGAGG 1960

CCGTGGATTC CCTGATGCGT CGGGCGGCCA AGACCATCAA 2000

CTTCGGCGTC CTCTACGGCA TGTCCGCCCA CCGGCTTTCG 2040

-continued

```
GGAGAGCTGG CCATCCCCTA CGAGGAGGCG GTGGCCTTCA    2080
TCGAGCGGTA TTTCCAGAGC TACCCCAAGG TGCGGGCCTG    2120
GATTGAGAAA ACCCTGGCGG AAGGACGGGA ACGGGGCTAT    2160
GTGGAAACCC TCTTTGGCCG CCGGCGCTAC GTGCCCGACT    2200
TGGCTTCCCG GGTGAAGAGC ATCCGGGAGG CAGCGGAGCG    2240
CATGGCCTTC AACATGCCGG TCCAGGGGAC CGCCGCGGAT    2280
TTGATGAAAC TGGCCATGGT GAAGCTCTTT CCCAGGCTTC    2320
AGGAGCTGGG GGCCAGGATG CTTTTGCAGG TGCACGACGA    2360
ACTGGTCCTC GAGGCTCCCA AGGAGCAAGC GGAGGAAGTC    2400
GCCCAGGAGG CCAAGCGGAC CATGGAGGAG GTGTGGCCCC    2440
TGAAGGTGCC CTTGGAGGTG GAAGTGGGCA TCGGGGAGGA    2480
CTGGCTTTCC GCCAAGGCCT AG                       2502
```

In another embodiment, the invention provides a nucleic acid of SEQ ID NO:5, a derivative nucleic acid related to *Thermus scotoductus*, strain SM3, having GAC (encoding Asp) in place of GGG (encoding Gly) at positions 136-138. SEQ ID NO:5 is provided below.

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGACTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAAGTGC CGGGTTTTGA GGCGGATGAC 360

GTCCTGGCCA CCCTGGCCAA GAAGGCGGAA AAGGAAGGCT 400

ACGAGGTGCG CATCCTCACC GCGGACCGGG ACCTTTACCA 440

GCTTCTTTCG GACCGAATCT CCATCCTTCA CCCGGAGGGT 480

TACCTGATCA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTTTC CCGGGTGCAC ACGGAGTTGC 760

CCCTTCAGGT GGACTTCGCC CGGCGCCGGG AGCCGGACCG 800

GGAAGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

-continued

```
GAGCTTAACG CCTTGGCCGC CGCCTGGGAG GGAAGGGTTT    1000
ACCGGGCGGA GGATCCCTTG GAGGCCTTGC GGGGGCTTGG    1040
GGAGGTGAGG GGGCTTTTGG CCAAGGACCT GGCGGTGCTG    1080
GCCCTGAGGG AAGGGATTGC CCTGGCACAG GGCGACGACC    1120
CCATGCTCCT CGCCTACCTC CTGGATCCTT CCAACACCGC    1160
CCCCGAAGGG GTAGCCCGGC GCTACGGGGG GGAGTGGACC    1200
GAGGAGGCGG GGGAAAGGGC GCTGCTTTCC GAAAGGCTTT    1240
ACGCCGCCCT CCTGGAGCGG CTTAAGGGGG AGGAGAGGCT    1280
TCTTTGGCTT TACGAGGAGG TGGAAAAGCC CCTTTCGCGG    1320
GTCCTGGCCC ACATGGAGGC CACGGGGGTA TGGTTGGATG    1360
TGGCCTACTT GAAGGCCCTT TCCCTGGAGG TGGAGGCGGA    1400
GCTCAGGCGC CTCGAGGAGG AGGTCCACCG ACTGGCCGGG    1440
CATCCTTTCA ACCTGAACTC CCGGGACCAG CTGGAAAGGG    1480
TCCTCTTTGA CGAGCTTGGG CTTCCCGCCA TCGGCAAGAC    1520
GGAGAAGACG GGTAAGCGTT CCACCAGCGC CGCCGTTTTG    1560
GAGGCTTTGA GGGAGGCTCA TCCCATAGTG GACCGCATCC    1600
TCCAGTACCG GGAGCTTTCC AAGCTCAAGG GAACGTACAT    1640
CGATCCCTTG CCCGCCCTGG TCCACCCCAA GACGAACCGC    1680
CTCCACACCC GTTTCAACCA GACGGCCACC GCCACGGGGA    1720
GGCTTAGCAG CTCGGATCCC AACCTGCAAA ATATCCCCGT    1760
GCGCACCCCT TTAGGCCAGC GGATCCGCCG GGCCTTCGTG    1800
GCCGAGGAGG GGTGGAGGCT GGTGGTTTTG GACTACAGCC    1840
AGATTGAGCT CAGGGTCCTG GCGCACCTTT CCGGGGACGA    1880
GAACCTGATC CGGGTCTTCC AAGAGGGCCA GGACATCCAC    1920
ACCCAGACGG CCAGCTGGAT GTTCGGCGTG CCCCCAGAGG    1960
CCGTGGATTC CCTGATGCGC CGGGCGGCCA AGACCATCAA    2000
CTTCGGCGTC CTCTACGGCA TGTCCGCCCA CCGGCTTTCG    2040
GGAGAGCTGG CCATCCCCTA CGAGGAAGCG GTGGCCTTCA    2080
TCGAGCGGTA TTTCCAGAGC TACCCCAAGG TACGGGCCTG    2120
GATTGAGAAA ACCCTGGCGG AAGGACGGGA GCGGGGCTAT    2160
GTGGAAACCC TCTTTGGCCG CCGGCGCTAT GTGCCCGACT    2200
TGGCTTCCCG GGTGAAGAGC ATCCGGGAGG CAGCGGAGCG    2240
CATGGCCTTC AACATGCCGG TCCAGGGGAC CGCCGCGGAT    2280
TTGATGAAAC TGGCCATGGT GAAGCTCTTT CCCAGGCTTC    2320
AGGAGCTGGG GGCCAGGATG CTTTTGCAGG TGCACGACGA    2360
ACTGGTCCTC GAGGCTCCCA AGGAGCAAGC GGAGGAAGTC    2400
GCCCAGGAGG CCAAGCGGAC CATGGAGGAG GTGTGGCCCC    2440
TGAAGGTGCC CTTGGAGGTG GAGGTGGGTA TCGGGGAGGA    2480
CTGGCTTTCC GCCAAGGCCT AGTCGAC                  2507
```

In another embodiment, the invention provides a nucleic acid of SEQ ID NO:6, a derivative nucleic acid related to *Thermus scotoductus*, strain Vi7a, having GAC (encoding Asp) in place of GGG (encoding Gly) at positions 136-138. SEQ ID NO:6 is provided below.

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGACTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAAGTGC CGGGTTTTGA GGCGGATGAC 360

GTCCTGGCCA CCCTGGCCAA GAAGGCGGAA AAGGAAGGCT 400

ACGAGGTGCG CATCCTCACC GCGGACCGGG ACCTTTACCA 440

GCTTCTTTCG GACCGAATCT CCATCCTTCA CCCGGAGGGT 480

TACCTGATTA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTTTC CCGGGTGCAC ACGGAGTTGC 760

CCCTTCAGGT GGACTTCGCC CGGCGCCGGG AGCCGGACCG 800

GGAAGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

ACCGGGCGGA GGATCCCTTG GAGGCCTTGC GGGGGCTTGG 1040

GGAGGTGAGG GGGCTTTTGG CCAAGGACCT GGCGGTGCTG 1080

GCCCTGAGGG AAGGGATTGC CCTGGCACCG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GCTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA TGGTTGGATG 1360

TGGCCTACTT GAAGGCCCTT TCCCTGGAGG TGGAGGCGGA 1400

GCTCAGGCGC CTCGAGGAGG AGGTCCACCG ACTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGTAAGCGTT CCACCAGCGC CGCCGTTTTG 1560

-continued

GAGGCTTTGA GGGAGGCTCA TCCCATAGTG GACCGCATCC 1600

TCCAGTACCG GGAGCTTTCC AAGCTCAAGG GAACGTACAT 1640

CGATCCCTTG CCCGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTAGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTGATC CGGGTCTTCC AAGAGGGCCA GGACATCCAC 1920

ACCCAGACGG CCAGCTGGAT GTTCGGCGTG CCCCCAGAGG 1960

CCGTGGATTC CCTGATGCGC CGGGCGGCCA AGACCATCAA 2000

CTACGGCGTC CTCTACGGCA TGTCCGCCCA CCGGCTTTCG 2040

GGAGAGCTGG CCATCCCCTA CGAGGAAGCG GTGGCCTTCA 2080

TCGAGCGGTA TTTCCAGAGC TTCCCCAAGG TACGGGCCTG 2120

GATTGAGAAA ACCCTGGCGG AAGGACGGGA GCGGGGCTAT 2160

GTGGAAACCC TCTTTGGCCG CCGGCGCTAT GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAGGTGGGTA TCGGGGAGGA 2480

CTGGCTTTCC GCCAAGGCCT AGTCGAC 2507

In another embodiment, the invention provides a nucleic acid of SEQ ID NO:7, a derivative nucleic acid related to *Thermus scotoductus*, strain X-1, having TAC (encoding Tyr) in place of TTC (encoding Phe) at positions 2002-04. SEQ ID NO:7 is provided below:

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGGGTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAGGTGC CGGGCTTTGA GGCGGATGAC 360

GTCCTGGCTA CCCTGGCCAA GAAGGCGGAA AAGGAAGGCT 400

ACGAGGTGCG CATCCTCACC GCGGACCGGG ACCTTTACCA 440

GCTTCTTTCG GAGCGAATCT CCATCCTTCA CCCGGAGGGT 480

-continued

TACCTGATCA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTATC CCGGGTGCGC ACGGACTTGC 760

CCCTTCAGGT GGACTTCGCC CGGCGCCGGG AGCCGGACCG 800

GGAGGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

ACCGGGCGGA GGATCCCTTG GAGGCCTTGC GGGGGCTTGG 1040

GGAGGTGAGG GGGCTTTTGG CCAAGGACCT GGCGGTGCTG 1080

GCCCTGAGGG AAGGGATTGC CCTGGCACCG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GTTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA CGGTTGGATG 1360

TGGCCTACTT AAAGGCCCTT TCCCTGGAGG TGGAGGCGGA 1400

GCTCAGGCGC CTCGAGGAGG AGGTCCACCG CCTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGCAAGCGCT CCACCAGCGC CGCCGTTTTG 1560

GAGGCCTTGC GGGAGGCTCA TCCCATCGTG GACCGCATCC 1600

TTCAGTACCG GGAGCTTTCC AAGCTCAAGG GAACCTACAT 1640

CGATCCCTTG CCTGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTGGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTAATC CGGGTCTTCC AGGAGGGCCA GGACATCCAC 1920

ACCCAGACGG CCAGCTGGAT GTTCGGCGTG CCCCCAGAGG 1960

CCGTGGATTC CCTGATGCGT CGGGCGGCCA AGACCATCAA 2000

CTACGGCGTC CTCTACGGCA TGTCCGCCCA CCGGCTTTCG 2040

GGAGAGCTGG CCATCCCCTA CGAGGAGGCG GTGGCCTTCA 2080

-continued

TCGAGCGGTA TTTCCAGAGC TACCCCAAGG TGCGGGCCTG 2120

GATTGAGAAA ACCCTGGCGG AAGGACGGGA ACGGGGCTAT 2160

GTGGAAACCC TCTTTGGCCG CCGGCGCTAC GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAAGTGGGCA TCGGGGAGGA 2480

CTGGCTTTCC GCCAAGGCCT AG 2502

In another embodiment, the invention provides a nucleic acid of SEQ ID NO:8, a derivative nucleic acid related to *Thermus scotoductus*, strain SM3, having TAC (encoding Tyr) in place of TTC (encoding Phe) at positions 2002-04. SEQ ID NO:8 is provided below:

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGGGTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAAGTGC CGGGTTTTGA GGCGGATGAC 360

GTCCTGGCCA CCCTGGCCAA GAAGGCGGAA AAGGAAGGCT 400

ACGAGGTGCG CATCCTCACC GCGGACCGGG ACCTTTACCA 440

GCTTCTTTCG GACCGAATCT CCATCCTTCA CCCGGAGGGT 480

TACCTGATCA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTTTC CCGGGTGCAC ACGGAGTTGC 760

CCCTTCAGGT GGACTTCGCC CGGCGCCGGG AGCCGGACCG 800

GGAAGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

-continued

ACCGGGCGGA GGATCCCTTG GAGGCCTTGC GGGGGCTTGG 1040

GGAGGTGAGG GGGCTTTTGG CCAAGGACCT GGCGGTGCTG 1080

GCCCTGAGGG AAGGGATTGC CCTGGCACAG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GCTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA TGGTTGGATG 1360

TGGCCTACTT GAAGGCCCTT TCCCTGGAGG TGGAGGCGGA 1400

GCTCAGGCGC CTCGAGGAGG AGGTCCACCG ACTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGTAAGCGTT CCACCAGCGC CGCCGTTTTG 1560

GAGGCTTTGA GGGAGGCTCA TCCCATAGTG GACCGCATCC 1600

TCCAGTACCG GGAGCTTTCC AAGCTCAAGG GAACGTACAT 1640

CGATCCCTTG CCCGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTAGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTGATC CGGGTCTTCC AAGAGGGCCA GGACATCCAC 1920

ACCCAGACGG CCAGCTGGAT GTTCGGCGTG CCCCCAGAGG 1960

CCGTGGATTC CCTGATGCGC CGGGCGGCCA AGACCATCAA 2000

CTACGGCGTC CTCTACGGCA TGTCCGCCCA CCGGCTTTCG 2040

GGAGAGCTGG CCATCCCCTA CGAGGAAGCG GTGGCCTTCA 2080

TCGAGCGGTA TTTCCAGAGC TACCCCAAGG TACGGGCCTG 2120

GATTGAGAAA ACCCTGGCGG AAGGACGGGA GCGGGGCTAT 2160

GTGGAAACCC TCTTTGGCCG CCGGCGCTAT GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAGGTGGGTA TCGGGGAGGA 2480

CTGGCTTTCC GCCAAGGCCT AGTCGAC 2507

In another embodiment, the invention provides a nucleic acid of SEQ ID NO:9, a derivative nucleic acid related to *Thermus scotoductus*, strain Vi7a, having TAC (encoding Tyr) in place of TTC (encoding Phe) at positions 2101-03. SEQ ID NO:9 is provided below:

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGGGTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAAGTGC CGGGTTTTGA GGCGGATGAC 360

GTCCTGGCCA CCCTGGCCAA GAAGGCGGAA AAGGAAGGCT 400

ACGAGGTGCG CATCCTCACC GCGGACCGGG ACCTTTACCA 440

GCTTCTTTCG GACCGAATCT CCATCCTTCA CCCGGAGGGT 480

TACCTGATTA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTTTC CCGGGTGCAC ACGGAGTTGC 760

CCCTTCAGGT GGACTTCGCC CGGCGCCGGG AGCCGGACCG 800

GGAAGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

ACCGGGCGGA GGATCCCTTG GAGGCCTTGC GGGGGCTTGG 1040

GGAGGTGAGG GGGCTTTTGG CCAAGGACCT GGCGGTGCTG 1080

GCCCTGAGGG AAGGGATTGC CCTGGCACCG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GCTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA TGGTTGGATG 1360

TGGCCTACTT GAAGGCCCTT TCCCTGGAGG TGGAGGCGGA 1400

GCTCAGGCGC CTCGAGGAGG AGGTCCACCG ACTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGTAAGCGTT CCACCAGCGC CGCCGTTTTG 1560

GAGGCTTTGA GGGAGGCTCA TCCCATAGTG GACCGCATCC 1600

TCCAGTACCG GGAGCTTTCC AAGCTCAAGG GAACGTACAT 1640

-continued

CGATCCCTTG CCCGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTAGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTGATC CGGGTCTTCC AAGAGGGCCA GGACATCCAC 1920

ACCCAGACGG CCAGCTGGAT GTTCGGCGTG CCCCCAGAGG 1960

CCGTGGATTC CCTGATGCGC CGGGCGGCCA AGACCATCAA 2000

CTACGGCGTC CTCTACGGCA TGTCCGCCCA CCGGCTTTCG 2040

GGAGAGCTGG CCATCCCCTA CGAGGAAGCG GTGGCCTTCA 2080

TCGAGCGGTA TTTCCAGAGC TACCCCAAGG TACGGGCCTG 2120

GATTGAGAAA ACCCTGGCGG AAGGACGGGA GCGGGGCTAT 2160

GTGGAAACCC TCTTTGGCCG CCGGCGCTAT GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAGGTGGGTA TCGGGGAGGA 2480

CTGGCTTTCC GCCAAGGCCT AGTCGAC 2507

In another embodiment, the invention provides a nucleic acid of SEQ ID NO:10, a derivative nucleic acid related to *Thermus scotoductus*, strain X-1, having GAC (encoding Asp) in place of GGG (encoding Gly) at positions 136-138 and having TAC (encoding Tyr) in place of TTC (encoding Phe) at positions 2002-04. SEQ ID NO:10 is provided below:

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGACTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAGGTGC CGGGCTTTGA GGCGGATGAC 360

GTCCTGGCTA CCCTGGCCAA GAAGGCGGAA AAGGAAGGCT 400

ACGAGGTGCG CATCCTCACC GCGGACCGGG ACCTTTACCA 440

GCTTCTTTCG GAGCGAATCT CCATCCTTCA CCCGGAGGGT 480

TACCTGATCA CCCCGGAGTG GCTTTGGGAG AAGTATGGGC 520

-continued

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTATC CCGGGTGCGC ACGGACTTGC 760

CCCTTCAGGT GGACTTCGCC CGGCGCCGGG AGCCGGACCG 800

GGAGGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

ACCGGGCGGA GGATCCCTTG GAGGCCTTGC GGGGGCTTGG 1040

GGAGGTGAGG GGGCTTTTGG CCAAGGACCT GGCGGTGCTG 1080

GCCCTGAGGG AAGGGATTGC CCTGGCACCG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GTTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA CGGTTGGATG 1360

TGGCCTACTT AAAGGCCCTT TCCCTGGAGG TGGAGGCGGA 1400

GCTCAGGCGC CTCGAGGAGG AGGTCCACCG CCTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGCAAGCGCT CCACCAGCGC CGCCGTTTTG 1560

GAGGCCTTGC GGGAGGCTCA TCCCATCGTG GACCGCATCC 1600

TTCAGTACCG GGAGCTTTCC AAGCTCAAGG GAACCTACAT 1640

CGATCCCTTG CCTGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTGGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTAATC CGGGTCTTCC AGGAGGGCCA GGACATCCAC 1920

ACCCAGACGG CCAGCTGGAT GTTCGGCGTG CCCCCAGAGG 1960

CCGTGGATTC CCTGATGCGT CGGGCGGCCA AGACCATCAA 2000

CTACGGCGTC CTCTACGGCA TGTCCGCCCA CCGGCTTTCG 2040

GGAGAGCTGG CCATCCCCTA CGAGGAGGCG GTGGCCTTCA 2080

TCGAGCGGTA TTTCCAGAGC TACCCCAAGG TGCGGGCCTG 2120

GATTGAGAAA ACCCTGGCGG AAGGACGGGA ACGGGGCTAT 2160

-continued

GTGGAAACCC TCTTTGGCCG CCGGCGCTAC GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAAGTGGGCA TCGGGGAGGA 2480

CTGGCTTTCC GCCAAGGCCT AG 2502

In another embodiment, the invention provides a nucleic acid of SEQ ID NO:11, a derivative nucleic acid related to *Thermus scotoductus*, strain SM3, having GAC (encoding Asp) in place of GGG (encoding Gly) at positions 136-138 and having TAC (encoding Tyr) in place of TTC (encoding Phe) at positions 2002-04. SEQ ID NO:8 is provided below:

ATGAGGGCGA TGCTGCCCCT CTTTGAGCCC AAGGGCCGGG 40

TGCTTCTGGT GGACGGCCAC CACCTGGCCT ACCGTACCTT 80

TTTTGCCCTG AAGGGCCTCA CCACCAGCCG CGGGGAGCCG 120

GTCCAGGCGG TGTACGACTT TGCCAAGAGC CTTTTGAAGG 160

CGCTAAGGGA AGACGGGGAT GTGGTGATCG TGGTGTTTGA 200

CGCCAAGGCC CCCTCCTTCC GCCACCAGAC CTACGAGGCC 240

TACAAGGCGG GGCGGGCTCC CACCCCCGAG GACTTTCCCC 280

GGCAGCTTGC CCTTATCAAG GAGATGGTGG ACCTTTTGGG 320

CCTGGAGCGC CTCGAAGTGC CGGGTTTTGA GGCGGATGAC 360

GTCCTGGCCA CCCTGGCCAA GAAGGCGGAA AAGGAAGGCT 400

ACGAGGTGCG CATCCTCACC GCGGACCGGG ACCTTTACCA 440

GCTTCTTTCG GACCGAATCT CCATCCTTCA CCCGGAGGGT 480

TACCTGATCA CCCCGGAGTG GCTTTGGGAG AAGTATGGGC 520

TTAAGCCTTC CCAGTGGGTG GACTACCGGG CCTTGGCCGG 560

GGACCCTTCC GACAACATCC CCGGCGTGAA GGGCATCGGG 600

GAGAAGACGG CGGCCAAGCT GATCCGGGAG TGGGGAAGCC 640

TGGAAAACCT TCTTAAGCAC CTGGAACAGG TGAAACCTGC 680

CTCCGTGCGG GAGAAGATCC TTAGCCACAT GGAGGACCTC 720

AAGCTATCCC TGGAGCTTTC CCGGGTGCAC ACGGAGTTGC 760

CCCTTCAGGT GGACTTCGCC CGGCGCCGGG AGCCGGACCG 800

GGAAGGGCTT AAGGCCTTTT TGGAGAGGCT GGAGTTCGGA 840

AGCCTCCTCC ACGAGTTCGG CCTGTTGGAA AGCCCGGTGG 880

CGGCGGAGGA AGCTCCCTGG CCGCCCCCCG AGGGAGCCTT 920

CGTGGGGTAC GTTCTTTCCC GCCCCGAGCC CATGTGGGCG 960

GAGCTTAACG CCTTGGCCGC CGCCTGGGAG GGAAGGGTTT 1000

ACCGGGCGGA GGATCCCTTG GAGGCCTTGC GGGGGCTTGG 1040

-continued

GGAGGTGAGG GGGCTTTTGG CCAAGGACCT GGCGGTGCTG 1080

GCCCTGAGGG AAGGGATTGC CCTGGCACAG GGCGACGACC 1120

CCATGCTCCT CGCCTACCTC CTGGATCCTT CCAACACCGC 1160

CCCCGAAGGG GTAGCCCGGC GCTACGGGGG GGAGTGGACC 1200

GAGGAGGCGG GGGAAAGGGC GCTGCTTTCC GAAAGGCTTT 1240

ACGCCGCCCT CCTGGAGCGG CTTAAGGGGG AGGAGAGGCT 1280

TCTTTGGCTT TACGAGGAGG TGGAAAAGCC CCTTTCGCGG 1320

GTCCTGGCCC ACATGGAGGC CACGGGGGTA TGGTTGGATG 1360

TGGCCTACTT GAAGGCCCTT TCCCTGGAGG TGGAGGCGGA 1400

GCTCAGGCGC CTCGAGGAGG AGGTCCACCG ACTGGCCGGG 1440

CATCCTTTCA ACCTGAACTC CCGGGACCAG CTGGAAAGGG 1480

TCCTCTTTGA CGAGCTTGGG CTTCCCGCCA TCGGCAAGAC 1520

GGAGAAGACG GGTAAGCGTT CCACCAGCGC CGCCGTTTTG 1560

GAGGCTTTGA GGGAGGCTCA TCCCATAGTG GACCGCATCC 1600

TCCAGTACCG GGAGCTTTCC AAGCTCAAGG GAACGTACAT 1640

CGATCCCTTG CCCGCCCTGG TCCACCCCAA GACGAACCGC 1680

CTCCACACCC GTTTCAACCA GACGGCCACC GCCACGGGGA 1720

GGCTTAGCAG CTCGGATCCC AACCTGCAAA ATATCCCCGT 1760

GCGCACCCCT TTAGGCCAGC GGATCCGCCG GGCCTTCGTG 1800

GCCGAGGAGG GGTGGAGGCT GGTGGTTTTG GACTACAGCC 1840

AGATTGAGCT CAGGGTCCTG GCGCACCTTT CCGGGGACGA 1880

GAACCTGATC CGGGTCTTCC AAGAGGGCCA GGACATCCAC 1920

ACCCAGACGG CCAGCTGGAT GTTCGGCGTG CCCCCAGAGG 1960

CCGTGGATTC CCTGATGCGC CGGGCGGCCA AGACCATCAA 2000

CTACGGCGTC CTCTACGGCA TGTCCGCCCA CCGGCTTTCG 2040

GGAGAGCTGG CCATCCCCTA CGAGGAAGCG GTGGCCTTCA 2080

TCGAGCGGTA TTTCCAGAGC TACCCCAAGG TACGGGCCTG 2120

GATTGAGAAA ACCCTGGCGG AAGGACGGGA GCGGGGCTAT 2160

GTGGAAACCC TCTTTGGCCG CCGGCGCTAT GTGCCCGACT 2200

TGGCTTCCCG GGTGAAGAGC ATCCGGGAGG CAGCGGAGCG 2240

CATGGCCTTC AACATGCCGG TCCAGGGGAC CGCCGCGGAT 2280

TTGATGAAAC TGGCCATGGT GAAGCTCTTT CCCAGGCTTC 2320

AGGAGCTGGG GGCCAGGATG CTTTTGCAGG TGCACGACGA 2360

ACTGGTCCTC GAGGCTCCCA AGGAGCAAGC GGAGGAAGTC 2400

GCCCAGGAGG CCAAGCGGAC CATGGAGGAG GTGTGGCCCC 2440

TGAAGGTGCC CTTGGAGGTG GAGGTGGGTA TCGGGGAGGA 2480

CTGGCTTTCC GCCAAGGCCT AGTCGAC 2507

In another embodiment, the invention provides a nucleic acid of SEQ ID NO:12, a derivative nucleic acid related to *Thermus scotoductus*, strain Vi7a, having GAC (encoding Asp) in place of GGG (encoding Gly) at positions 136-138 and having TAC (encoding Tyr) in place of TTC (encoding Phe) at positions 2101-03. SEQ ID NO:12 is provided below:

```
ATGAGGGCGA TGCTGCCCCT CTTTGAGCCC AAGGGCCGGG     40
TGCTTCTGGT GGACGGCCAC CACCTGGCCT ACCGTACCTT     80
TTTTGCCCTG AAGGGCCTCA CCACCAGCCG CGGGGAGCCG    120
GTCCAGGCGG TGTACGACTT TGCCAAGAGC CTTTTGAAGG    160
CGCTAAGGGA AGACGGGGAT GTGGTGATCG TGGTGTTTGA    200
CGCCAAGGCC CCCTCCTTCC GCCACCAGAC CTACGAGGCC    240
TACAAGGCGG GGCGGGCTCC CACCCCCGAG GACTTTCCCC    280
GGCAGCTTGC CCTTATCAAG GAGATGGTGG ACCTTTTGGG    320
CCTGGAGCGC CTCGAAGTGC CGGGTTTTGA GGCGGATGAC    360
GTCCTGGCCA CCCTGGCCAA GAAGGCGGAA AAGGAAGGCT    400
ACGAGGTGCG CATCCTCACC GCGGACCGGG ACCTTTACCA    440
GCTTCTTTCG GACCGAATCT CCATCCTTCA CCCGGAGGGT    480
TACCTGATTA CCCCGGAGTG GCTTTGGGAG AAGTATGGGC    520
TTAAGCCTTC CCAGTGGGTG GACTACCGGG CCTTGGCCGG    560
GGACCCTTCC GACAACATCC CCGGCGTGAA GGGCATCGGG    600
GAGAAGACGG CGGCCAAGCT GATCCGGGAG TGGGGAAGCC    640
TGGAAAACCT TCTTAAGCAC CTGGAACAGG TGAAACCTGC    680
CTCCGTGCGG GAGAAGATCC TTAGCCACAT GGAGGACCTC    720
AAGCTATCCC TGGAGCTTTC CCGGGTGCAC ACGGAGTTGC    760
CCCTTCAGGT GGACTTCGCC CGGCGCCGGG AGCCGGACCG    800
GGAAGGGCTT AAGGCCTTTT TGGAGAGGCT GGAGTTCGGA    840
AGCCTCCTCC ACGAGTTCGG CCTGTTGGAA AGCCCGGTGG    880
CGGCGGAGGA AGCTCCCTGG CCGCCCCCCG AGGGAGCCTT    920
CGTGGGGTAC GTTCTTTCCC GCCCCGAGCC CATGTGGGCG    960
GAGCTTAACG CCTTGGCCGC CGCCTGGGAG GGAAGGGTTT   1000
ACCGGGCGGA GGATCCCTTG GAGGCCTTGC GGGGGCTTGG   1040
GGAGGTGAGG GGGCTTTTGG CCAAGGACCT GGCGGTGCTG   1080
GCCCTGAGGG AAGGGATTGC CCTGGCACCG GGCGACGACC   1120
CCATGCTCCT CGCCTACCTC CTGGATCCTT CCAACACCGC   1160
CCCCGAAGGG GTAGCCCGGC GCTACGGGGG GGAGTGGACC   1200
GAGGAGGCGG GGGAAAGGGC GCTGCTTTCC GAAAGGCTTT   1240
ACGCCGCCCT CCTGGAGCGG CTTAAGGGGG AGGAGAGGCT   1280
TCTTTGGCTT TACGAGGAGG TGGAAAAGCC CCTTTCGCGG   1320
GTCCTGGCCC ACATGGAGGC CACGGGGGTA TGGTTGGATG   1360
TGGCCTACTT GAAGGCCCTT TCCCTGGAGG TGGAGGCGGA   1400
GCTCAGGCGC CTCGAGGAGG AGGTCCACCG ACTGGCCGGG   1440
CATCCTTTCA ACCTGAACTC CCGGGACCAG CTGGAAAGGG   1480
TCCTCTTTGA CGAGCTTGGG CTTCCCGCCA TCGGCAAGAC   1520
GGAGAAGACG GGTAAGCGTT CCACCAGCGC CGCCGTTTTG   1560
GAGGCTTTGA GGGAGGCTCA TCCCATAGTG GACCGCATCC   1600
TCCAGTACCG GGAGCTTTCC AAGCTCAAGG GAACGTACAT   1640
```

-continued

```
CGATCCCTTG CCCGCCCTGG TCCACCCCAA GACGAACCGC   1680
CTCCACACCC GTTTCAACCA GACGGCCACC GCCACGGGGA   1720
GGCTTAGCAG CTCGGATCCC AACCTGCAAA ATATCCCCGT   1760
GCGCACCCCT TTAGGCCAGC GGATCCGCCG GGCCTTCGTG   1800
GCCGAGGAGG GGTGGAGGCT GGTGGTTTTG GACTACAGCC   1840
AGATTGAGCT CAGGGTCCTG GCGCACCTTT CCGGGGACGA   1880
GAACCTGATC CGGGTCTTCC AAGAGGGCCA GGACATCCAC   1920
ACCCAGACGG CCAGCTGGAT GTTCGGCGTG CCCCCAGAGG   1960
CCGTGGATTC CCTGATGCGC CGGGCGGCCA AGACCATCAA   2000
CTACGGCGTC CTCTACGGCA TGTCCGCCCA CCGGCTTTCG   2040
GGAGAGCTGG CCATCCCCTA CGAGGAAGCG GTGGCCTTCA   2080
TCGAGCGGTA TTTCCAGAGC TACCCCAAGG TACGGGCCTG   2120
GATTGAGAAA ACCCTGGCGG AAGGACGGGA GCGGGGCTAT   2160
GTGGAAACCC TCTTTGGCCG CCGGCGCTAT GTGCCCGACT   2200
TGGCTTCCCG GGTGAAGAGC ATCCGGGAGG CAGCGGAGCG   2240
CATGGCCTTC AACATGCCGG TCCAGGGGAC CGCCGCGGAT   2280
TTGATGAAAC TGGCCATGGT GAAGCTCTTT CCCAGGCTTC   2320
AGGAGCTGGG GGCCAGGATG CTTTTGCAGG TGCACGACGA   2360
ACTGGTCCTC GAGGCTCCCA AGGAGCAAGC GGAGGAAGTC   2400
GCCCAGGAGG CCAAGCGGAC CATGGAGGAG GTGTGGCCCC   2440
TGAAGGTGCC CTTGGAGGTG GAGGTGGGTA TCGGGGAGGA   2480
CTGGCTTTCC GCCAAGGCCT AGTCGAC                 2507
```

The substitution of TAC (encoding Tyr) for TTC (encoding Phe) at the indicated positions can reduce discrimination against ddNTP incorporation by DNA polymerase I. See, e.g., U.S. Pat. No. 5,614,365 that is incorporated herein by reference. The substitution of GAC (encoding Asp) for GGG (encoding Gly) at the indicated positions removes the 5'-3' exonuclease activity.

The nucleic acids of the invention have homology to portions of the nucleic acids encoding the thermostable DNA polymerases of *Thermus aquaticus* and *Thermus thermophilus* (see FIG. 1). However, significant portions of the nucleic acid sequences of the present invention are distinct.

The invention also encompasses fragment and variant nucleic acids of SEQ ID NO:1-12. Nucleic acid "fragments" encompassed by the invention are of two general types. First, fragment nucleic acids that do not encode a full-length nucleic acid polymerase but do encode a thermally stable polypeptide with nucleic acid polymerase activity are encompassed within the invention. Second, fragment nucleic acids useful as hybridization probes but that generally do not encode polymerases retaining biological activity are also encompassed within the invention. Thus, fragments of nucleotide sequences such as SEQ ID NO:1-12 may be as small as about 9 nucleotides, about 12 nucleotides, about 15 nucleotides, about 17 nucleotides, about 18 nucleotides, about 20 nucleotides, about 50 nucleotides, about 100 nucleotides or more. In general, a fragment nucleic acid of the invention can have any upper size limit so long as it is related in sequence to the nucleic acids of the invention but is not full length.

As indicated above, "variants" are substantially similar or substantially homologous sequences. For nucleotide sequences, variants include those sequences that, because of the degeneracy of the genetic code, encode the identical amino acid sequence of the native nucleic acid polymerase protein. Variant nucleic acids also include those that encode polypeptides that do not have amino acid sequences identical to that of a native nucleic acid polymerase protein, but that encode an active, thermally stable nucleic acid polymerase with conservative changes in the amino acid sequence.

As is known by one of skill in the art, the genetic code is "degenerate," meaning that several trinucleotide codons can encode the same amino acid. This degeneracy is apparent from Table 1.

TABLE 1

| | Second Position | | | | |
|---|---|---|---|---|---|
| $1^{st}$ Position | T | C | A | G | $3^{rd}$ Position |
| T | TTT = Phe | TCT = Ser | TAT = Tyr | TGT = Cys | T |
| T | TTC = Phe | TCC = Ser | TAC = Tyr | TGC = Cys | C |
| T | TTA = Leu | TCA = Ser | TAA = Stop | TGA = Stop | A |
| T | TTG = Leu | TCG = Ser | TAG = Stop | TGG = Trp | G |
| C | CTT = Leu | CCT = Pro | CAT = His | CGT = Arg | T |
| C | CTC = Leu | CCC = Pro | CAC = His | CGC = Arg | C |
| C | CTA = Leu | CCA = Pro | CAA = Gln | CGA = Arg | A |
| C | CTG = Leu | CCG = Pro | CAG = Gln | CGG = Arg | G |
| A | ATT = Ile | ACT = Thr | AAT = Asn | AGT = Ser | T |
| A | ATC = Ile | ACC = Thr | AAC = Asn | AGC = Ser | C |
| A | ATA = Ile | ACA = Thr | AAA = Lys | AGA = Arg | A |
| A | ATG = Met | ACG = Thr | AAG = Lys | AGG = Arg | G |
| G | GTT = Val | GCT = Ala | GAT = Asp | GGT = Gly | T |
| G | GTC = Val | GCC = Ala | GAC = Asp | GGC = Gly | C |
| G | GTA = Val | GCA = Ala | GAA = Gln | GGA = Gly | A |
| G | GTG = Val | GCG = Ala | GAG = Gln | GGG = Gly | G |

Hence, many changes in the nucleotide sequence of the variant may be silent and may not alter the amino acid sequence encoded by the nucleic acid. Where nucleic acid sequence alterations are silent, a variant nucleic acid will encode a polypeptide with the same amino acid sequence as the reference nucleic acid. Therefore, a particular nucleic acid sequence of the invention also encompasses variants with degenerate codon substitutions, and complementary sequences thereof, as well as the sequence explicitly specified by a SEQ ID NO. Specifically, degenerate codon substitutions may be achieved by generating sequences in which the reference codon is replaced by any of the codons for the amino acid specified by the reference codon. In general, the third position of one or more selected codons can be substituted with mixed-base and/or deoxyinosine residues as disclosed by Batzer et al., Nucleic Acid Res., 19, 5081 (1991) and/or Ohtsuka et al., J. Biol. Chem., 260, 2605 (1985); Rossolini et al., Mol. Cell. Probes, 8, 91 (1994).

However, the invention is not limited to silent changes in the present nucleotide sequences but also includes variant nucleic acid sequences that conservatively alter the amino acid sequence of a polypeptide of the invention. According to the present invention, variant and reference nucleic acids of the invention may differ in the encoded amino acid sequence by one or more substitutions, additions, insertions, deletions, fusions and truncations, which may be present in any combination, so long as an active, thermally stable nucleic acid polymerase is encoded by the variant nucleic acid. Such variant nucleic acids will not encode exactly the same amino acid sequence as the reference nucleic acid, but have conservative sequence changes.

Variant nucleic acids with silent and conservative changes can be defined and characterized by the degree of homology to the reference nucleic acid. Preferred variant nucleic acids are "substantially homologous" to the reference nucleic acids of the invention. As recognized by one of skill in the art, such substantially similar nucleic acids can hybridize under stringent conditions with the reference nucleic acids identified by SEQ ID NOs herein. These types of substantially homologous nucleic acids are encompassed by this invention.

Generally, nucleic acid derivatives and variants of the invention will have at least 90%, 91%, 92%, 93% or 94% sequence identity to the reference nucleotide sequence defined herein. Preferably, nucleic acids of the invention will have at least at least 95%, 96%, 97%, 98%, or 99% sequence identity to the reference nucleotide sequence defined herein.

Variant nucleic acids can be detected and isolated by standard hybridization procedures.

Hybridization to detect or isolate such sequences is generally carried out under stringent conditions. "Stringent hybridization conditions" and "stringent hybridization wash conditions" in the context of nucleic acid hybridization experiments such as Southern and Northern hybridization are sequence dependent, and are different under different environmental parameters. Longer sequences hybridize specifically at higher temperatures. An extensive guide to the hybridization of nucleic acids is found in Tijssen, Laboratory Techniques in Biochemistry and Molecular biology-Hybridization with Nucleic Acid Probes, page 1, chapter 2 "Overview of principles of hybridization and the strategy of nucleic acid probe assays" Elsevier, New York (1993). See also, J. Sambrook et al., Molecular Cloning: A Laboratory Manual, Cold Spring Harbor Press, N.Y., pp 9.31-9.58 (1989); J. Sambrook et al., Molecular Cloning: A Laboratory Manual, Cold Spring Harbor Press, N.Y. (3rd ed. 2001).

The invention also provides methods for detection and isolation of derivative or variant nucleic acids encoding nucleic acid polymerase activity. The methods involve hybridizing at least a portion of a nucleic acid comprising any one of SEQ ID NO:1-12 to a sample nucleic acid, thereby forming a hybridization complex; and detecting the hybridization complex. The presence of the complex correlates with the presence of a derivative or variant nucleic acid encoding at least a segment of nucleic acid polymerase. In general, the portion of a nucleic acid comprising any one of SEQ ID NO:1-12 used for hybridization is at least fifteen nucleotides, and hybridization is under hybridization conditions that are sufficiently stringent to permit detection and isolation of substantially homologous nucleic acids. In an alternative embodiment, a nucleic acid sample is amplified by the polymerase chain reaction using primer oligonucleotides selected from any one of SEQ ID NO:1-12.

Generally, highly stringent hybridization and wash conditions are selected to be about SEC lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions, nucleic acids that are 100% complementary can be identified.

Alternatively, stringency conditions can be adjusted to allow some mismatching in sequences so that lower degrees of similarity are detected (heterologous probing). Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl and 0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

The degree of complementarity or homology of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ can be approximated from the equation of Meinkoth and Wahl Anal. Biochem. 138:267-284 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

Very stringent conditions are selected to be equal to the $T_m$ for a particular probe.

An example of stringent hybridization conditions for hybridization of complementary nucleic acids that have more than 100 complementary residues on a filter in a Southern or Northern blot is 50% formamide with 1 mg of heparin at 42 EC, with the hybridization being carried out overnight. An example of highly stringent conditions is 0.1 5 M NaCl at 72 EC for about 15 minutes. An example of stringent wash conditions is a 0.2×SSC wash at 65 EC for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45 EC for 15 minutes. An example low stringency wash for a duplex of, e.g., more than 100 nucleotides, is 4-6×SSC at 40 EC for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30 EC.

Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to detect and isolate homologous nucleic acids that are substantially identical to reference nucleic acids of the present invention: a reference nucleotide sequence preferably hybridizes to the reference nucleotide sequence in 7% sodium dodecyl sulfate (SDS), 0.5 M $NaPO_4$, 1 mM EDTA at 50 EC with washing in 2×SSC, 0.1% SDS at 50 EC, more desirably in 7% sodium dodecyl sulfate (SDS), 0.5 M $NaPO_4$, 1 mM EDTA at 50 EC with washing in 1×SSC, 0.1% SDS at 50 EC, more desirably still in 7% sodium dodecyl sulfate (SDS), 0.5 M $NaPO_4$, 1 mM EDTA at 50 EC with washing in 0.5×SSC, 0.1% SDS at 50 EC, preferably in 7% sodium dodecyl sulfate (SDS), 0.5 M $NaPO_4$, 1 mM EDTA at 50 EC with washing in 0.1×SSC, 0.1% SDS at 50 EC, more preferably in 7% sodium dodecyl sulfate (SDS), 0.5 M $NaPO_4$, 1 mM EDTA at 50 EC with washing in 0.1×SSC, 0.1% SDS at 65 EC.

In general, $T_m$ is reduced by about 1° C. for each 1% of mismatching. Thus, $T_m$, hybridization, and/or wash conditions can be adjusted to hybridize to sequences of the desired sequence identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, New York); and Ausubel et al., eds. (1995) Current Protocols in Molecular Biology, Chapter 2 (Greene Publishing and Wiley—Interscience, New York). See Sambrook et al. (1989) Molecular Cloning: A Laboratory Manual (2d ed., Cold Spring Harbor Laboratory Press, Plainview, N.Y.). Using these references and the teachings herein on the relationship between $T_m$, mismatch, and hybridization and wash conditions, those of ordinary skill can generate variants of the present nucleic acid polymerase nucleic acids.

Computer analyses can also be utilized for comparison of sequences to determine sequence identity. Such analyses include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. Gene 73:237 244 (1988); Higgins et al. CABIOS 5:151-153 (1989); Corpet et al. Nucleic Acids Res. 16:10881-90 (1988); Huang et al. CABIOS 8:155-65 (1992); and Pearson et al. Meth. Mol. Biol. 24:307-331 (1994). The ALIGN program is based on the algorithm of Myers and Miller, supra. The BLAST programs of Altschul et al., J. Mol. Biol. 215:403 (1990), are based on the algorithm of Karlin and Altschul supra. To obtain gapped alignments for comparison purposes, Gapped BLAST (in BLAST 2.0) can be utilized as described in Altschul et al. Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA, 89, 10915 (1989)). See http://www.ncbi.nlm.nih.gov. Alignment may also be performed manually by inspection.

For purposes of the present invention, comparison of nucleotide sequences for determination of percent sequence identity to the nucleic acid polymerase sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Expression of Nucleic Acids Encoding Polymerases

Nucleic acids of the invention may be used for the recombinant expression of the nucleic acid polymerase polypeptides of the invention. Generally, recombinant expression of a nucleic acid polymerase polypeptide of the invention is effected by introducing a nucleic acid encoding that polypeptide into an expression vector adapted for use in particular type of host cell. The nucleic acids of the invention can be introduced and expressed in any host organism, for example, in both prokaryotic or eukaryotic host cells. Examples of host cells include bacterial cells, yeast cells, cultured insect cell lines, and cultured mammalian cells lines. Preferably, the recombinant host cell system is selected that processes and post-translationally modifies nascent polypeptides in a manner similar to that of the organism from which the nucleic acid polymerase was derived. For purposes of expressing and isolating nucleic acid Polymerase polypeptides of the invention, prokaryotic organisms are preferred, for example, *Escherichia coli*. Accordingly, the invention provides host cells comprising the expression vectors of the invention.

The nucleic acids to be introduced can be conveniently placed in expression cassettes for expression in an organism of interest. Such expression cassettes will comprise a transcriptional initiation region linked to a nucleic acid of the invention. Expression cassettes preferably also have a plurality of restriction sites for insertion of the nucleic acid to be under the transcriptional regulation of various control elements. The expression cassette additionally may contain selectable marker genes. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Preferably the nucleic acid in the vector is under the control of, and operably linked to, an appropriate promoter or other regulatory elements for transcription in a host cell. The vector may be a bi-functional expression vector that functions in multiple hosts. The transcriptional cassette generally includes in the 5'-3' direction of transcription, a promoter, a transcriptional and translational initiation region, a DNA sequence of interest, and a transcriptional and translational termination region functional in the organism. The termination region may be native with the transcriptional initiation region, may be native with the DNA sequence of interest, or may be derived from another source.

Efficient expression of recombinant nucleic acids in prokaryotic and eukaryotic cells generally requires regulatory control elements directing the efficient termination and polyadenylation of the resulting transcript. Transcription termination signals are generally found downstream of the polyadenylation signal and are a few hundred nucleotides in length. The term "poly A site" or "poly A sequence" as used herein denotes a nucleic acid sequence that directs both the termination and polyadenylation of the nascent RNA transcript. Efficient polyadenylation of the recombinant transcript is desirable as transcripts lacking a poly A tail are unstable and are rapidly degraded.

Nucleic acids encoding nucleic acid polymerase may be introduced into bacterial host cells by a method known to one of skill in the art. For example, nucleic acids encoding a thermophilic nucleic acid polymerase can be introduced into bacterial cells by commonly used transformation procedures such as by treatment with calcium chloride or by electroporation. If the thermophilic nucleic acid polymerase is to be expressed in eukaryotic host cells, nucleic acids encoding the thermophilic nucleic acid polymerase may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation.

Thus, one aspect of the invention is to provide expression vectors and host cells comprising a nucleic acid encoding a nucleic acid polymerase polypeptide of the invention. A wide range of expression vectors are well known in the art. Description of various expression vectors and how to use them can be found among other places in U.S. Pat. Nos. 5,604,118; 5,583,023; 5,432,082; 5,266,490; 5,063,158; 4,966,841; 4,806,472; 4,801,537; and Goedel et al., Gene Expression Technology, Methods of Enzymology, Vol. 185, Academic Press, San Diego (1989). The expression of nucleic acid polymerases in recombinant cell systems is a well-established technique. Examples of the recombinant expression of nucleic acid polymerase can be found in U.S. Pat. Nos. 5,602,756; 5,545,552; 5,541,311; 5,500,363; 5,489,523; 5,455,170; 5,352,778; 5,322,785; and 4,935,361.

Recombinant DNA and molecular cloning techniques that can be used to help make and use aspects of the invention are described by Sambrook et al., Molecular Cloning: A Laboratory Manual Vol. 1-3, Cold Spring Harbor laboratory, Cold Spring Harbor, N.Y. (2001); Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

Nucleic Acid Polymerase Enzymes

The invention provides *Thermus scotoductus* nucleic acid polymerase polypeptides, as well as fragments thereof and variant nucleic acid Polymerase polypeptides that are active and thermally stable. Any polypeptide containing amino acid sequence having any one of SEQ ID NO:13-28, which are the amino acid sequences for wild type and derivative *Thermus scotoductus* nucleic acid polymerases, are contemplated by the present invention. The polypeptides of the invention are isolated or substantially purified polypeptides. In particular, the isolated polypeptides of the invention are substantially free of proteins normally present in *Thermus scotoductus* bacteria.

In one embodiment, the invention provides a polypeptide of SEQ ID NO:13, a wild type *Thermus scotoductus* nucleic acid polymerase polypeptide from strain X-1 with three additional amino acids at the N-terminus:

```
MRAMLPLFEP KGRVLLVDGH HLAYRTFFAL KGLTTSRGEP     40
VQAVYGFAKS LLKALREDGD VVIVVFDAKA PSFRHQTYEA     80
YKAGRAPTPE DFPRQLALIK EMVDLLGLER LEVPGFEADD    120
VLATLAKKAE KEGYEVRILT ADRDLYQLLS ERISILHPEG    160
YLITPEWLWE KYGLKPSQWV DYRALAGDPS DNIPGVKGIG    200
EKTAAKLIRE WGSLENLLKH LEQVKPASVR EKILSHMEDL    240
KLSLELSRVR TDLPLQVDFA RRREPDREGL KAFLERLEFG    280
SLLHEFGLLE SPVAAEEAPW PPPEGAFVGY VLSRPEPMWA    320
ELNALAAAWE GRVYRAEDPL EALRGLGEVR GLLAKDLAVL    360
ALREGIALAP GDDPMLLAYL LDPSNTAPEG VARRYGGEWT    400
EEAGERALLS ERLYAALLER LKGEERLLWL YEEVEKPLSR    440
VLAHMEATGV RLDVAYLKAL SLEVEAELRR LEEEVHRLAG    480
HPFNLNSRDQ LERVLFDELG LPAIGKTEKT GKRSTSAAVL    520
EALREAHPIV DRILQYRELS KLKGTYIDPL PALVHPKTNR    560
LHTRFNQTAT ATGRLSSSDP NLQNIPVRTP LGQRIRRAFV    600
AEEGWRLVVL DYSQIELRVL AHLSGDENLI RVFQEGQDIH    640
TQTASWMFGV PPEAVDSLMR RAAKTINFGV LYGMSAHRLS    680
GELAIPYEEA VAFIERYFQS YPKVRAWIEK TLAEGRERGY    720
VETLFGRRRY VPDLASRVKS IREAAERMAF NMPVQGTAAD    760
LMKLAMVKLF PRLQELGARM LLQVHDELVL EAPKEQAEEV    800
AQEAKRTMEE VWPLKVPLEV EVGIGEDWLS AKA           833
```

In another embodiment, the invention provides SEQ ID NO:14, a wild type *Thermus scotoductus* nucleic acid polymerase enzyme, from strain X-1 that does not have the three additional amino acids at the N-terminus that are present in SEQ ID NO:13. SEQ ID NO:14 is provided below.

```
MLPLFEP KGRVLLVDGH HLAYRTFFAL KGLTTSRGEP        40
VQAVYGFAKS LLKALREDGD VVIVVFDAKA PSFRHQTYEA     80
YKAGRAPTPE DFPRQLALIK EMVDLLGLER LEVPGFEADD    120
VLATLAKKAE KEGYEVRILT ADRDLYQLLS ERISILHPEG    160
YLITPEWLWE KYGLKPSQWV DYRALAGDPS DNIPGVKGIG    200
EKTAAKLIRE WGSLENLLKH LEQVKPASVR EKILSHMEDL    240
KLSLELSRVR TDLPLQVDFA RRREPDREGL KAFLERLEFG    280
SLLHEFGLLE SPVAAEEAPW PPPEGAFVGY VLSRPEPMWA    320
ELNALAAAWE GRVYRAEDPL EALRGLGEVR GLLAKDLAVL    360
ALREGIALAP GDDPMLLAYL LDPSNTAPEG VARRYGGEWT    400
EEAGERALLS ERLYAALLER LKGEERLLWL YEEVEKPLSR    440
VLAHMEATGV RLDVAYLKAL SLEVEAELRR LEEEVHRLAG    480
HPFNLNSRDQ LERVLFDELG LPAIGKTEKT GKRSTSAAVL    520
EALREAHPIV DRILQYRELS KLKGTYIDPL PALVHPKTNR    560
LHTRFNQTAT ATGRLSSSDP NLQNIPVRTP LGQRIRRAFV    600
```

-continued

```
AEEGWRLVVL DYSQIELRVL AHLSGDENLI RVFQEGQDIH     640
TQTASWMFGV PPEAVDSLMR RAAKTINFGV LYGMSAHRLS     680
GELAIPYEEA VAFIERYFQS YPKVRAWIEK TLAEGRERGY     720
VETLFGRRRY VPDLASRVKS IREAAERMAF NMPVQGTAAD     760
LMKLAMVKLF PRLQELGARM LLQVHDELVL EAPKEQAEEV     800
AQEAKRTMEE VWPLKVPLEV EVGIGEDWLS AKA            833
```

In another embodiment, the invention provides SEQ ID NO:15, a wild type *Thermus scotoductus* nucleic acid polymerase enzyme from strain SM3. SEQ ID NO:15 is provided below.

```
MRAMLPLFEP KGRVLLVDGH HLAYRTFFAL KGLTTSRGEP      40
VQAVYGFAKS LLKALREDGD VVIVVFDAKA PSFRHQTYEA      80
YKAGRAPTPE DFPRQLALIK EMVDLLGLER LEVPGFEADD     120
VLATLAKKAE KEGYEVRILT ADRDLYQLLS DRISILHPEG     160
YLITPEWLWE KYGLKPSQWV DYRALAGDPS DNIPGVKGIG     200
EKTAAKLIRE WGSLENLLKH LEQVKPASVR EKILSHMEDL     240
KLSLELSRVH TELPLQVDFA RRREPDREGL KAFLERLEFG     280
SLLHEFGLLE SPVAAEEAPW PPPEGAFVGY VLSRPEPMWA     320
ELNALAAAWE GRVYRAEDPL EALRGLGEVR GLLAKDLAVL     360
ALREGIALAQ GDDPMLLAYL LDPSNTAPEG VARRYGGEWT     400
EEAGERALLS ERLYAALLER LKGEERLLWL YEEVEKPLSR     440
VLAHMEATGV WLDVAYLKAL SLEVEAELRR LEEEVHRLAG     480
HPFNLNSRDQ LERVLFDELG LPAIGKTEKT GKRSTSAAVL     520
EALREAHPIV DRILQYRELS KLKGTYIDPL PALVHPKTNR     560
LHTRFNQTAT ATGRLSSSDP NLQNIPVRTP LGQRIRRAFV     600
AEEGWRLVVL DYSQIELRVL AHLSGDENLI RVFQEGQDIH     640
TQTASWMFGV PPEAVDSLMR RAAKTINFGV LYGMSAHRLS     680
GELAIPYEEA VAFIERYFQS YPKVRAWIEK TLAEGRERGY     720
VETLFGRRRY VPDLASRVKS IREAAERMAF NMPVQGTAAD     760
LMKLAMVKLF PRLQELGARM LLQVHDELVL EAPKEQAEEV     800
AQEAKRTMEE VWPLKVPLEV EVGIGEDWLS AKA            833
```

In another embodiment, the invention provides SEQ ID NO:16, a wild type *Thermus scotoductus* nucleic acid polymerase enzyme from strain Vi7a. SEQ ID NO:16 is provided below.

```
MRAMLPLFEP KGRVLLVDGH HLAYRTFFAL KGLTTSRGEP      40
VQAVYGFAKS LLKALREDGD VVIVVFDAKA PSFRHQTYEA      80
YKAGRAPTPE DFPRQLALIK EMVDLLGLER LEVPGFEADD     120
VLATLAKKAE KEGYEVRILT ADRDLYQLLS DRISILHPEG     160
YLITPEWLWE KYGLKPSQWV DYRALAGDPS DNIPGVKGIG     200
EKTAAKLIRE WGSLENLLKH LEQVKPASVR EKILSHMEDL     240
```

-continued

```
KLSLELSRVH TELPLQVDFA RRREPDREGL KAFLERLEFG     280
SLLHEFGLLE SPVAAEEAPW PPPEGAFVGY VLSRPEPMWA     320
ELNALAAAWE GRVYRAEDPL EALRGLGEVR GLLAKDLAVL     360
ALREGIALAP GDDPMLLAYL LDPSNTAPEG VARRYGGEWT     400
EEAGERALLS ERLYAALLER LKGEERLLWL YEEVEKPLSR     440
VLAHMEATGV WLDVAYLKAL SLEVEAELRR LEEEVHRLAG     480
HPFNLNSRDQ LERVLFDELG LPAIGKTEKT GKRSTSAAVL     520
EALREAHPIV DRILQYRELS KLKGTYIDPL PALVHPKTNR     560
LHTRFNQTAT ATGRLSSSDP NLQNIPVRTP LGQRIRRAFV     600
AEEGWRLVVL DYSQIELRVL AHLSGDENLI RVFQEGQDIH     640
TQTASWMFGV PPEAVDSLMR RAAKTINFGV LYGMSAHRLS     680
GELAIPYEEA VAFIERYFQS YPKVRAWIEK TLAEGRERGY     720
VETLFGRRRY VPDLASRVKS IREAAERMAF NMPVQGTAAD     760
LMKLAMVKLF PRLQELGARM LLQVHDELVL EAPKEQAEEV     800
AQEAKRTMEE VWPLKVPLEV EVGIGEDWLS AKA            833
```

The sequences of wild type *Thermus scotoductus* nucleic acid polymerases are distinct from the amino acid sequence of *Thermus aquaticus* DNA Polymerase. There are about 51 conservative amino acid differences and about 62 nonconservative amino acid differences. For example, one region of dissimilarity is between approximate amino acid positions 51 and 65, where the sequence of the *Thermus scotoductus* polymerase has about four amino acid differences (in bold): LLKALREDG DVVIVVFDAK APSFRHQTYE (SEQ ID NO:39). Another region of dissimilarity is between approximate amino acid positions 201 and 236, where the sequence of the *Thermus scotoductus* polymerase has about seven amino acid differences (in bold):

```
                                    (SEQ ID NO: 40)
GEKTAAKLIREWGSLENLLKHLEQV KPASV REKILS.
```

Another region of dissimilarity is between about positions 311 and 350, where the sequence of the *Thermus scotoductus* polymerase has about seven amino acid changes (in bold): VGYVLSRPEPMWAELN ALAAAWEGRVYRAED-PLEALRGLG (SEQ ID NO:41). Another region of dissimilarity is between about positions 415 and 435, where the sequence of the *Thermus scotoductus* polymerase has about five amino acid changes (in bold): RLYAALLERLKGEER-LLWLYE (SEQ ID NO:42). Another region of dissimilarity is between about positions 531 and 562, where the sequence of the *Thermus scotoductus* polymerase has about six amino acid changes (in bold): PIVDRILQYRELSKLK GTYID PLPALVHPKTN (SEQ ID NO:43). Another region of dissimilarity is between about positions 801 and 836, where the sequence of the *Thermus scotoductus* polymerase has about eight amino acid changes (in bold): EEVAQEAKRT MEEVWPLKVPLEVEVGIGEDWLSAKA (SEQ ID NO:44). Hence, many regions of the *Thermus scotoductus* polymerase differ from the *Thermus aquaticus* and *Thermus thermophilus* DNA polymerases.

Many DNA polymerases possess activities in addition to a DNA polymerase activity. Such activities include, for example, a 5'-3' exonuclease activity and/or a 3'-5' exonuclease activity. The 3'-5' exonuclease activity improves the accuracy of the newly synthesized strand by removing incorrect bases that may have been incorporated. DNA polymerases in which such activity is low or absent are prone to errors in the incorporation of nucleotide residues into the primer extension strand. Taq DNA polymerase has been reported to have low 3'-5' exonuclease activity. See Lawyer et al., J. Biol Chem. 264:6427-6437. In applications such as nucleic acid amplification procedures in which the replication of DNA is often geometric in relation to the number of primer extension cycles, such errors can lead to serious artifactual problems such as sequence heterogeneity of the nucleic acid amplification product (amplicon). Thus, a 3'-5' exonuclease activity is a desired characteristic of a thermostable DNA polymerase used for such purposes.

By contrast, the 5'-3' exonuclease activity of DNA polymerase enzymes is often undesirable because this activity may digest nucleic acids, including primers, that have an unprotected 5' end. Thus, a thermostable nucleic acid polymerase with an attenuated 5'-3' exonuclease activity, or in which such activity is absent, is a desired characteristic of an enzyme for biochemical applications. Various DNA polymerase enzymes have been described where a modification has been introduced in a DNA polymerase that accomplishes this object. For example, the Klenow fragment of *E. coli* DNA polymerase I can be produced as a proteolytic fragment of the holoenzyme in which the domain of the protein controlling the 5'-3' exonuclease activity has been removed. The Klenow fragment still retains the polymerase activity and the 3'-5' exonuclease activity. Barnes, PCT Publication No. WO92/06188 (1992) and Gelfand et al., U.S. Pat. No. 5,079,352 have produced 5'-3' exonuclease-deficient recombinant *Thermus aquaticus* DNA polymerases. Ishino et al., EPO Publication No. 0517418A2, have produced a 5'-3' exonuclease-deficient DNA polymerase derived from *Bacillus caldotenax.*

In another embodiment, the invention provides a polypeptide that is a derivative *Thermus scotoductus* polypeptide with reduced or eliminated 5'-3' exonuclease activity. Several methods exist for reducing this activity, and the invention contemplates any polypeptide derived from the *Thermus scotoductus* polypeptides of the invention that has reduced or eliminated such 5'-3' exonuclease activity. Xu et al., *Biochemical and mutational studies of the* 5'-3' *exonuclease of DNA polymerase I of Escherichia coli*. J. Mol. Biol. 1997 May 2; 268(2):284-302.

In one embodiment, the invention provides a *Thermus scotoductus* nucleic acid polymerase polypeptide from strain X-1 in which Asp is used in place of Gly at position 46. This polypeptide has SEQ ID NO:17 and reduced 5'-3' exonuclease activity. SEQ ID NO:17 is provided below.

```
MRAMLPLFEP KGRVLLVDGH HLAYRTFFAL KGLTTSRGEP      40

VQAVYDFAKS LLKALREDGD VVIVVFDAKA PSFRHQTYEA      80

YKAGRAPTPE DFPRQLALIK EMVDLLGLER LEVPGFEADD     120

VLATLAKKAE KEGYEVRILT ADRDLYQLLS ERISILHPEG     160

YLITPEWLWE KYGLKPSQWV DYRALAGDPS DNIPGVKGIG     200

EKTAAKLIRE WGSLENLLKH LEQVKPASVR EKILSHMEDL     240

KLSLELSRVR TDLPLQVDFA RRREPDREGL KAFLERLEFG     280

SLLHEFGLLE SPVAAEEAPW PPPEGAFVGY VLSRPEPMWA     320

ELNALAAAWE GRVYRAEDPL EALRGLGEVR GLLAKDLAVL     360
```

-continued

```
ALREGIALAP GDDPMLLAYL LDPSNTAPEG VARRYGGEWT     400

EEAGERALLS ERLYAALLER LKGEERLLWL YEEVEKPLSR     440

VLAHMEATGV RLDVAYLKAL SLEVEAELRR LEEEVHRLAG     480

HPFNLNSRDQ LERVLFDELG LPAIGKTEKT GKRSTSAAVL     520

EALREAHPIV DRILQYRELS KLKGTYIDPL PALVHPKTNR     560

LHTRFNQTAT ATGRLSSSDP NLQNIPVRTP LGQRIRRAFV     600

AEEGWRLVVL DYSQIELRVL AHLSGDENLI RVFQEGQDIH     640

TQTASWMFGV PPEAVDSLMR RAAKTINFGV LYGMSAHRLS     680

GELAIPYEEA VAFIERYFQS YPKVRAWIEK TLAEGRERGY     720

VETLFGRRRY VPDLASRVKS IREAAERMAF NMPVQGTAAD     760

LMKLAMVKLF PRLQELGARM LLQVHDELVL EAPKEQAEEV     800

AQEAKRTMEE VWPLKVPLEV EVGIGEDWLS AKA            833
```

In another embodiment, the invention provides a *Thermus scotoductus* nucleic acid polymerase polypeptide from strain X-1 in which Asp is used in place of Gly at position 46. This polypeptide has SEQ ID NO:18 and reduced 5'-3' exonuclease activity. SEQ ID NO:18 is provided below.

```
   MLPLFEP KGRVLLVDGH HLAYRTFFAL KGLTTSRGEP      40

VQAVYDFAKS LLKALREDGD VVIVVFDAKA PSFRHQTYEA      80

YKAGRAPTPE DFPRQLALIK EMVDLLGLER LEVPGFEADD     120

VLATLAKKAE KEGYEVRILT ADRDLYQLLS ERISILHPEG     160

YLITPEWLWE KYGLKPSQWV DYRALAGDPS DNIPGVKGIG     200

EKTAAKLIRE WGSLENLLKH LEQVKPASVR EKILSHMEDL     240

KLSLELSRVR TDLPLQVDFA RRREPDREGL KAFLERLEFG     280

SLLHEFGLLE SPVAAEEAPW PPPEGAFVGY VLSRPEPMWA     320

ELNALAAAWE GRVYRAEDPL EALRGLGEVR GLLAKDLAVL     360

ALREGIALAP GDDPMLLAYL LDPSNTAPEG VARRYGGEWT     400

EEAGERALLS ERLYAALLER LKGEERLLWL YEEVEKPLSR     440

VLAHMEATGV RLDVAYLKAL SLEVEAELRR LEEEVHRLAG     480

HPFNLNSRDQ LERVLFDELG LPAIGKTEKT GKRSTSAAVL     520

EALREAHPIV DRILQYRELS KLKGTYIDPL PALVHPKTNR     560

LHTRFNQTAT ATGRLSSSDP NLQNIPVRTP LGQRIRRAFV     600

AEEGWRLVVL DYSQIELRVL AHLSGDENLI RVFQEGQDIH     640

TQTASWMFGV PPEAVDSLMR RAAKTINFGV LYGMSAHRLS     680

GELAIPYEEA VAFIERYFQS YPKVRAWIEK TLAEGRERGY     720

VETLFGRRRY VPDLASRVKS IREAAERMAF NMPVQGTAAD     760

LMKLAMVKLF PRLQELGARM LLQVHDELVL EAPKEQAEEV     800

AQEAKRTMEE VWPLKVPLEV EVGIGEDWLS AKA            833
```

In another embodiment, the invention provides a *Thermus scotoductus* nucleic acid polymerase polypeptide from strain SM3 in which Asp is used in place of Gly at position 46. This polypeptide has SEQ ID NO:19 and reduced 5'-3' exonuclease activity. SEQ ID NO:19 is provided below.

MRAMLPLFEP KGRVLLVDGH HLAYRTFFAL KGLTTSRGEP 40

VQAVYDFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS DRISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVH TELPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAQ GDDPMLLAYL LDPSNTAPEG VARRYGGEWT 400

EEAGERALLS ERLYAALLER LKGEERLLWL YEEVEKPLSR 440

VLAHMEATGVnWLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINFGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a *Thermus scotoductus* nucleic acid polymerase polypeptide from strain Vi7a in which Asp is used in place of Gly at position 46. This polypeptide has SEQ ID NO:20 and reduced 5'-3' exonuclease activity. SEQ ID NO:20 is provided below.

MRAMLPLFEP KGRVLLVDGH HLAYRTFFAL KGLTTSRGEP 40

VQAVYDFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS DRISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVH TELPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAP GDDPMLLAYL LDPSNTAPEG VARRYGGEWT 400

EEAGERALLS ERLYAALLER LKGEERLLWL YEEVEKPLSR 440

VLAHMEATGV WLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

-continued

AEEGWRLVVL DYSQIELRVL AHLSGDENLI RVFQEGQDIH 640

TQTASWMFGV PPEAVDSLMR RAAKTINFGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:21, a derivative *Thermus scotoductus* polypeptide from strain X-1 with reduced bias against ddNTP incorporation. SEQ ID NO:21 has Tyr in place of Phe at position 668. The sequence of SEQ ID NO:21 is below.

MRAMLPLFEP KGRVLLVDGH HLAYRTFFAL KGLTTSRGEP 40

VQAVYGFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS ERISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVR TDLPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAP GDDPMLLAYL LDPSNTAPEG VARRYGGEWT 400

EEAGERALLS ERLYAALLER LKGEERLLWL YEEVEKPLSR 440

VLAHMEATGV RLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINYGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:22, a derivative *Thermus scotoductus* polypeptide from strain X-1 with reduced bias against ddNTP incorporation. SEQ ID NO:22 has Tyr in place of Phe at position 668. The sequence of SEQ ID NO:22 is below.

MLPLFEP KGRVLLVDGH HLAYRTFFAL KGLTTSRGEP 40

VQAVYGFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS ERISILHPEG 160

YLITPEWLWE KYGLKPSQWV DYRALAGDPS DNIPGVKGIG 200

-continued

EKTAAKLIRE WGSLENLLKH LEQVKPASVR EKILSHMEDL 240

KLSLELSRVR TDLPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAP GDDPMLLAYL LDPSNTAPEG VARRYGGEWT 400

EEAGERALLS ERLYAALLER LKGEERLLWL YEEVEKPLSR 440

VLAHMEATGV RLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINYGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:23, a derivative *Thermus scotoductus* polypeptide from strain SM3 with reduced bias against ddNTP incorporation. SEQ ID NO:23 has Tyr in place of Phe at position 668. The sequence of SEQ ID NO:23 is below.

MRAMLPLFEP KGRVLLVDGH HLAYRTFFAL KGLTTSRGEP 40

VQAVYGFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS DRISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVH TELPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAQ GDDPMLLAYL LDPSNTAPEG VARRYGGEWT 400

EEAGERALLS ERLYAALLER LKGEERLLWL YEEVEKPLSR 440

VLAHMEATGV WLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINYGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

-continued

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:24, a derivative *Thermus scotoductus* polypeptide from strain Vi7a with reduced bias against ddNTP incorporation. SEQ ID NO:24 has Tyr in place of Phe at position 668.

MRAMLPLFEP KGRVLLVDGH HLAYRTFFAL KGLTTSRGEP 40

VQAVYGFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS DRISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVH TELPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAP GDDPMLLAYL LDPSNTAPEG VARRYGGEWT 400

EEAGERALLS ERLYAALLER LKGEERLLWL YEEVEKPLSR 440

VLAHMEATGV WLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINYGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:25, a derivative *Thermus scotoductus* polypeptide from strain X-1 with reduced 5'-3' exonuclease activity and reduced bias against ddNTP incorporation. SEQ ID NO:25 has Asp in place of Gly at position 46 and Tyr in place of Phe at position 668. The sequence of SEQ ID NO:25 is below.

MRAMLPLFEP KGRVLLVDGH HLAYRTFFAL KGLTTSRGEP 40

VQAVYDFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS ERISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVR TDLPLQVDFA RRREPDREGL KAFLERLEFG 280

-continued

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAP GDDPMLLAYL LDPSNTAPEG VARRYGGEWT 400

EEAGERALLS ERLYAALLER LKGEERLLWL YEEVEKPLSR 440

VLAHMEATGV RLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINYGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:26 a derivative *Thermus scotoductus* polypeptide from strain X-1 with reduced 5'-3' exonuclease activity and reduced bias against ddNTP incorporation. SEQ ID NO:26 has Asp in place of Gly at position 46 and Tyr in place of Phe at position 668. The sequence of SEQ ID NO:26 is below.

MLPLFEP KGRVLLVDGH HLAYRTFFAL KGLTTSRGEP 40

VQAVYDFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS ERISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVR TDLPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAP GDDPMLLAYL LDPSNTAPEG VARRYGGEWT 400

EEAGERALLS ERLYAALLER LKGEERLLWL YEEVEKPLSR 440

VLAHMEATGV RLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINYGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:27 a derivative *Thermus scotoductus* polypeptide from strain SM3 with reduced 5'-3' exonuclease activity and reduced bias against ddNTP incorporation. SEQ ID NO:27 has Asp in place of Gly at position 46 and Tyr in place of Phe at position 668. The sequence of SEQ ID NO:27 is below.

MRAMLPLFEP KGRVLLVDGH HLAYRTFFAL KGLTTSRGEP 40

VQAVYDFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS DRISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVH TELPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

ALREGIALAQ GDDPMLLAYL LDPSNTAPEG VARRYGGEWT 400

EEAGERALLS ERLYAALLER LKGEERLLWL YEEVEKPLSR 440

VLAHMEATGV WLDVAYLKAL SLEVEAELRR LEEEVHRLAG 480

HPFNLNSRDQ LERVLFDELG LPAIGKTEKT GKRSTSAAVL 520

EALREAHPIV DRILQYRELS KLKGTYIDPL PALVHPKTNR 560

LHTRFNQTAT ATGRLSSSDP NLQNIPVRTP LGQRIRRAFV 600

AEEGWRLVVL DYSQIELRVL AHLSGDENLI RVFQEGQDIH 640

TQTASWMFGV PPEAVDSLMR RAAKTINYGV LYGMSAHRLS 680

GELAIPYEEA VAFIERYFQS YPKVRAWIEK TLAEGRERGY 720

VETLFGRRRY VPDLASRVKS IREAAERMAF NMPVQGTAAD 760

LMKLAMVKLF PRLQELGARM LLQVHDELVL EAPKEQAEEV 800

AQEAKRTMEE VWPLKVPLEV EVGIGEDWLS AKA 833

In another embodiment, the invention provides a polypeptide of SEQ ID NO:28 a derivative *Thermus scotoductus* polypeptide from strain Vi7a with reduced 5'-3' exonuclease activity and reduced bias against ddNTP incorporation. SEQ ID NO:28 has Asp in place of Gly at position 46 and Tyr in place of Phe at position 46 and 668. The sequence of SEQ ID NO:28 is below.

MRAMLPLFEP KGRVLLVDGH HLAYRTFFAL KGLTTSRGEP 40

VQAVYDFAKS LLKALREDGD VVIVVFDAKA PSFRHQTYEA 80

YKAGRAPTPE DFPRQLALIK EMVDLLGLER LEVPGFEADD 120

VLATLAKKAE KEGYEVRILT ADRDLYQLLS DRISILHPEG 160

YLITPEWLWE KYGLKPSQWV DYRALAGDPS DNIPGVKGIG 200

EKTAAKLIRE WGSLENLLKH LEQVKPASVR EKILSHMEDL 240

KLSLELSRVH TELPLQVDFA RRREPDREGL KAFLERLEFG 280

SLLHEFGLLE SPVAAEEAPW PPPEGAFVGY VLSRPEPMWA 320

ELNALAAAWE GRVYRAEDPL EALRGLGEVR GLLAKDLAVL 360

-continued

```
ALREGIALAP GDDPMLLAYL LDPSNTAPEG VARRYGGEWT     400

EEAGERALLS ERLYAALLER LKGEERLLWL YEEVEKPLSR     440

VLAHMEATGV WLDVAYLKAL SLEVEAELRR LEEEVHRLAG     480

HPFNLNSRDQ LERVLFDELG LPAIGKTEKT GKRSTSAAVL     520

EALREAHPIV DRILQYRELS KLKGTYIDPL PALVHPKTNR     560

LHTRFNQTAT ATGRLSSSDP NLQNIPVRTP LGQRIRRAFV     600

AEEGWRLVVL DYSQIELRVL AHLSGDENLI RVFQEGQDIH     640

TQTASWMFGV PPEAVDSLMR RAAKTINYGV LYGMSAHRLS     680

GELAIPYEEA VAFIERYFQS YPKVRAWIEK TLAEGRERGY     720

VETLFGRRRY VPDLASRVKS IREAAERMAF NMPVQGTAAD     760

LMKLAMVKLF PRLQELGARM LLQVHDELVL EAPKEQAEEV     800

AQEAKRTMEE VWPLKVPLEV EVGIGEDWLS AKA            833
```

The nucleic acid polymerase polypeptides of the invention have homology to portions of the amino acid sequences of the thermostable DNA polymerases of *Thermus aquaticus* and *Thermus thermophilus* (see FIG. 1). However, significant portions of the amino acid sequences of the present invention are distinct, including SEQ ID NO:39-44.

As indicated above, derivative and variant polypeptides of the invention are derived from the wild type nucleic acid polymerase by deletion or addition of one or more amino acids to the N-terminal and/or C-terminal end of the wild type polypeptide; deletion or addition of one or more amino acids at one or more sites within the wild type polypeptide; or substitution of one or more amino acids at one or more sites within the wild type polypeptide. Thus, the polypeptides of the invention may be altered in various ways including amino acid substitutions, deletions, truncations, and insertions.

Such variant and derivative polypeptides may result, for example, from genetic polymorphism or from human manipulation. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82, 488 (1985); Kunkel et al., Methods in Enzymol., 154, 367 (1987); U.S. Pat. No. 4,873,192; Walker and Gaastra, eds., Techniques in Molecular Biology, MacMillan Publishing Company, New York (1983) and the references cited therein. Guidance as to appropriate amino acid substitutions that do not affect biological activity of the protein of interest may be found in the model of Dayhoff et al., Atlas of Protein Sequence and Structure, Natl. Biomed. Res. Found., Washington, C. D. (1978), herein incorporated by reference.

The derivatives and variants of the isolated polypeptides of the invention have identity with at least about 92% of the amino acid positions of any one of SEQ ID NO:13-28 and have nucleic acid polymerase activity and/or are thermally stable. In a preferred embodiment, polypeptide derivatives and variants have identity with at least about 95% of the amino acid positions of any one of SEQ ID NO:13-28 and have nucleic acid polymerase activity and/or are thermally stable. In a more preferred embodiment, polypeptide derivatives and variants have identity with at least about 98% of the amino acid positions of any one of SEQ ID NO:13-28 and have nucleic acid polymerase activity and/or are thermally stable.

Amino acid residues of the isolated polypeptides and polypeptide derivatives and variants can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 2.

TABLE 2

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| ∃-Alanine | | Bala |
| 2,3-Diaminopropionic acid | | Dpr |
| ∀-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| ∃-2-thienylalanine | | Thi |
| Methionine sulfoxide | | MSO |
| Homoarginine | | Harg |
| N-acetyl lysine | | AcLys |
| 2,4-Diamino butyric acid | | Dbu |
| Δ-Aminophenylalanine | | Phe($pNH_2$) |
| N-methylvaline | | MeVal |
| Homocysteine | | Hcys |
| Homoserine | | Hser |
| ,-Amino hexanoic acid | | Aha |
| *-Amino valeric acid | | Ava |
| 2,3-Diaminobutyric acid | | Dab |

Polypeptide variants that are encompassed within the scope of the invention can have one or more amino acids substituted with an amino acid of similar chemical and/or physical properties, so long as these variant polypeptides retain polymerase activity and/or remain thermally stable. Derivative polypeptides can have one or more amino acids substituted with amino acids having different chemical and/or physical properties, so long as these variant polypeptides retain polymerase activity and/or remain thermally stable.

Amino acids that are substitutable for each other in the present variant polypeptides generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated B-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, ∃-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a polypeptide.

Certain commonly encountered amino acids that are not genetically encoded and that can be present, or substituted for an amino acid, in the variant polypeptides of the invention include, but are not limited to, ∃-alanine (b-Ala) and other omega-amino acids such as 3-aminopropionic acid (Dap), 2,3-diaminopropionic acid (Dpr), 4-aminobutyric acid and so forth; ∀-aminoisobutyric acid (Aib); ,-aminohexanoic acid (Aha); *-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-NaI); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe ($pNH_2$)); N-methyl valine (MeVal); homocysteine (hCys) and homoserine (hSer). These amino acids also fall into the categories defined above.

The classifications of the above-described genetically encoded and non-encoded amino acids are summarized in Table 3, below. It is to be understood that Table 3 is for illustrative purposes only and does not purport to be an exhaustive list of amino acid residues that may comprise the variant and derivative polypeptides described herein. Other amino acid residues that are useful for making the variant and derivative polypeptides described herein can be found, e.g., in Fasman, 1989, CRC Practical Handbook of Biochemistry and Molecular Biology, CRC Press, Inc., and the references cited therein Amino acids not specifically mentioned herein can be conveniently classified into the above-described categories on the basis of known behavior and/or their characteristic chemical and/or physical properties as compared with amino acids specifically identified.

TABLE 3

| Classification | Genetically Encoded | Genetically Non-Encoded |
|---|---|---|
| Hydrophobic | F, L, I, V | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | S, K | Cit, hCys |
| Acidic | D, E | |
| Basic | H, K, R | Dpr, Orn, hArg, Phe(p-$NH_2$), DBU, $A_2$ BU |
| Polar | Q, N, S, T, Y | Cit, AcLys, MSO, hSer |
| Cysteine-Like | C | Pen, hCys, ∃-methyl Cys |

Polypeptides of the invention can have any amino acid substituted by any similarly classified amino acid to create a variant peptide, so long as the peptide variant is thermally stable and/or retains DNA Polymerase activity.

"Domain shuffling" or construction of "thermostable chimeric nucleic acid polymerases" may be used to provide thermostable polymerases containing novel properties. For example, placement of codons 289-422 from the *Thermus scotoductus* DNA polymerase coding sequence after codons 1-288 of the *Thermus aquaticus* DNA polymerase would yield a novel thermostable nucleic acid polymerase containing the 5'-3' exonuclease domain of *Thermus aquaticus* DNA polymerase (1-289), the 3'-5' exonuclease domain of *Thermus scotoductus* nucleic acid polymerase (289-422), and the DNA polymerase domain of *Thermus aquaticus* DNA polymerase (423-832). Alternatively, the 5'-3' exonuclease domain and the 3'-5' exonuclease domain of *Thermus scotoductus* nucleic acid polymerase may be fused to the DNA polymerase (dNTP binding and primer/template binding domains) portions of *Thermus aquaticus* DNA polymerase (about codons 423-832). The donors and recipients need not be limited to *Thermus aquaticus* and *Thermus scotoductus* polymerases. *Thermus thermophilus* DNA polymerase 3'-5' exonuclease, 5'-3' exonuclease and DNA polymerase domains can similarly be exchanged for those in the *Thermus scotoductus* polymerases of the invention.

It has been demonstrated that the exonuclease domain of *Thermus aquaticus* Polymerase I can be removed from the amino terminus of the protein with out a significant loss of thermostability or polymerase activity (Erlich et al., (1991) Science 252: 1643-1651, Barnes, W. M., (1992) Gene 112: 29-35., Lawyer et al., (1989) JBC 264:6427-6437). Other N-terminal deletions similarly have been shown to maintain thermostability and activity (Vainshtein et al., (1996) Protein Science 5:1785-1792 and references therein.) Therefore this invention also includes similarly truncated forms of any of the wild type or variant polymerases provided herein. For example, the invention is also directed to an active truncated variant of any of the polymerases provided by the invention in which the first 330 amino acids are removed.

Moreover, the invention provides SEQ ID NO:45, a truncated form of a polymerase in which the N-terminal 289 amino acids have been removed from the wild type *Thermus scotoductus* polymerase from strain X-1.

```
                                         E SPVAAEEAPW    300

PPPEGAFVGY VLSRPEPMWA ELNALAAAWE GRVYRAEDPL    340

EALRGLGEVR GLLAKDLAVL ALREGIALAP GDDPMLLAYL    380
```

-continued

```
LDPSNTAPEG VARRYGGEWT EEAGERALLS ERLYAALLER    420

LKGEERLLWL YEEVEKPLSR VLAHMEATGV RLDVAYLKAL    460

SLEVEAELRR LEEEVHRLAG HPFNLNSRDQ LERVLFDELG    500

LPAIGKTEKT GKRSTSAAVL EALREAHPIV DRILQYRELS    540

KLKGTYIDPL PALVHPKTNR LHTRFNQTAT ATGRLSSSDP    580

NLQNIPVRTP LGQRIRRAFV AEEGWRLVVL DYSQIELRVL    620

AHLSGDENLI RVFQEGQDIH TQTASWMFGV PPEAVDSLMR    660

RAAKTINFGV LYGMSAHRLS GELAIPYEEA VAFIERYFQS    700

YPKVRAWIEK TLAEGRERGY VETLFGRRRY VPDLASRVKS    740

IREAAERMAF NMPVQGTAAD LMKLAMVKLF PRLQELGARM    780

LLQVHDELVL EAPKEQAEEV AQEAKRTMEE VWPLKVPLEV    820

EVGIGEDWLS AKA                                 833
```

Moreover, the invention provides SEQ ID NO:46 a truncated form of a polymerase in which the N-terminal 289 amino acids have been removed from the wild type *Thermus scotoductus* polymerase from strain SM3.

```
                                         E SPVAAEEAPW    300

PPPEGAFVGY VLSRPEPMWA ELNALAAAWE GRVYRAEDPL    340

EALRGLGEVR GLLAKDLAVL ALREGIALAQ GDDPMLLAYL    380

LDPSNTAPEG VARRYGGEWT EEAGERALLS ERLYAALLER    420

LKGEERLLWL YEEVEKPLSR VLAHMEATGV WLDVAYLKAL    460

SLEVEAELRR LEEEVHRLAG HPFNLNSRDQ LERVLFDELG    500

LPAIGKTEKT GKRSTSAAVL EALREAHPIV DRILQYRELS    540

KLKGTYIDPL PALVHPKTNR LHTRFNQTAT ATGRLSSSDP    580

NLQNIPVRTP LGQRIRRAFV AEEGWRLVVL DYSQIELRVL    620

AHLSGDENLI RVFQEGQDIH TQTASWMFGV PPEAVDSLMR    660

RAAKTINFGV LYGMSAHRLS GELAIPYEEA VAFIERYFQS    700

YPKVRAWIEK TLAEGRERGY VETLFGRRRY VPDLASRVKS    740

IREAAERMAF NMPVQGTAAD LMKLAMVKLF PRLQELGARM    780

LLQVHDELVL EAPKEQAEEV AQEAKRTMEE VWPLKVPLEV    820

EVGIGEDWLS AKA                                 833
```

Moreover, the invention provides SEQ ID NO:47 a truncated form of a polymerase in which the N-terminal 289 amino acids have been removed from the wild type *Thermus scotoductus* polymerase from strain Vi7a.

```
                                         E SPVAAEEAPW    300

PPPEGAFVGY VLSRPEPMWA ELNALAAAWE GRVYRAEDPL    340

EALRGLGEVR GLLAKDLAVL ALREGIALAP GDDPMLLAYL    380

LDPSNTAPEG VARRYGGEWT EEAGERALLS ERLYAALLER    420

LKGEERLLWL YEEVEKPLSR VLAHMEATGV WLDVAYLKAL    460

SLEVEAELRR LEEEVHRLAG HPFNLNSRDQ LERVLFDELG    500
```

-continued

```
LPAIGKTEKT GKRSTSAAVL EALREAHPIV DRILQYRELS     540

KLKGTYIDPL PALVHPKTNR LHTRFNQTAT ATGRLSSSDP     580

NLQNIPVRTP LGQRIRRAFV AEEGWRLVVL DYSQIELRVL     620

AHLSGDENLI RVFQEGQDIH TQTASWMFGV PPEAVDSLMR     660

RAAKTINFGV LYGMSAHRLS GELAIPYEEA VAFIERYFQS     700

YPKVRAWIEK TLAEGRERGY VETLFGRRRY VPDLASRVKS     740

IREAAERMAF NMPVQGTAAD LMKLAMVKLF PRLQELGARM     780

LLQVHDELVL EAPKEQAEEV AQEAKRTMEE VWPLKVPLEV     820

EVGIGEDWLS AKA                                  833
```

Thus, the polypeptides of the invention encompass both naturally occurring proteins as well as variations, truncations and modified forms thereof. Such variants will continue to possess the desired activity. The deletions, insertions, and substitutions of the polypeptide sequence encompassed herein are not expected to produce radical changes in the characteristics of the polypeptide. One skilled in the art can readily evaluate the thermal stability and polymerase activity of the polypeptides and variant polypeptides of the invention by routine screening assays.

Kits and compositions containing the present polypeptides are substantially free of cellular material. Such preparations and compositions have less than about 30%, 20%, 10%, 5%, (by dry weight) of contaminating bacterial cellular protein.

The activity of nucleic acid polymerase polypeptides and variant polypeptides can be assessed by any procedure known to one of skill in the art. For example, the DNA synthetic activity of the variant and non-variant polymerase polypeptides of the invention can be tested in standard DNA sequencing or DNA primer extension reaction. One such assay can be performed in a 100 μl (final volume) reaction mixture, containing, for example, 0.1 mM dCTP, dTTP, dGTP, ∀-$^{32}$P-dATP, 0.3 mg/ml activated calf thymus DNA and 0.5 mg/ml BSA in a buffer containing: 50 mM KCl, 1 mM DTT, 10 mM $MgCl_2$ and 50 mM of a buffering compound such as PIPES, Tris or Triethylamine. A dilution to 0.1 units/μl of each polymerase enzyme is prepared, and 5 μl of such a dilution is added to the reaction mixture, followed by incubation at 60 EC for 10 minutes. Reaction products can be detected by determining the amount of $^{32}$P incorporated into DNA or by observing the products after separation on a polyacrylamide gel.

Uses for Nucleic Acid Polymerase Polypeptides

The thermostable enzyme of this invention may be used for any purpose in which DNA Polymerase or reverse transcriptase activity is necessary or desired. For example, the present nucleic acid polymerase polypeptides can be used in one or more of the following procedures: DNA sequencing, DNA amplification, RNA amplification, reverse transcription, DNA synthesis and/or primer extension. The nucleic acid polymerase polypeptides of the invention can be used to amplify DNA by polymerase chain reaction (PCR). The nucleic acid polymerase polypeptides of the invention can be used to sequence DNA by Sanger sequencing procedures. The nucleic acid polymerase polypeptides of the invention can also be used in primer extension reactions. The nucleic acid polymerase polypeptides of the invention can also be used for reverse transcription. The nucleic acid polymerase polypeptides of the invention can be used test for single nucleotide polymorphisms (SNPs) by single nucleotide primer extension using terminator nucleotides. Any such procedures and related procedures, for example, polynucleotide or primer labeling, minisequencing and the like are contemplated for use with the present nucleic acid polymerase polypeptides.

Methods of the invention comprise the step of extending a primed polynucleotide template with at least one labeled nucleotide, wherein the extension is catalyzed by a nucleic acid polymerase of the invention. Nucleic acid polymerases used for Sanger sequencing can produce fluorescently labeled products that are analyzed on an automated fluorescence-based sequencing apparatus such as an Applied Biosystems 310 or 377 (Applied Biosystems, Foster City, Calif.). Detailed protocols for Sanger sequencing are known to those skilled in the art and may be found, for example in Sambrook et al, Molecular Cloning, A Laboratory Manual, Second Edition, Cold Spring Harbor Press, Cold Spring Harbor, N.Y. (1989).

In one embodiment, the nucleic acid polymerase polypeptides of the invention are used for DNA amplification. Any procedure that employs a DNA polymerase can be used, for example, in polymerase chain reaction (PCR) assays, strand displacement amplification and other amplification procedures. Strand displacement amplification can be used as described in Walker et al (1992) Nucl. Acids Res. 20, 1691-1696. The term "polymerase chain reaction" ("PCR") refers to the method of K. B. Mullis U.S. Pat. Nos. 4,683,195; 4,683,202; and 4,965,188, hereby incorporated by reference, which describe a method for increasing the concentration of a segment of a target sequence in a mixture of genomic DNA or other DNA or RNA without cloning or purification.

The PCR process for amplifying a target sequence consists of introducing a large excess of two oligonucleotide primers to the DNA mixture containing the desired target sequence, followed by a precise sequence of thermal cycling in the presence of a nucleic acid polymerase. The two primers are complementary to their respective strands of the double stranded target sequence. To effect amplification, the mixture is denatured and the primers annealed to their complementary sequences within the target molecule. Following annealing, the primers are extended with a polymerase so as to form a new pair of complementary strands. The steps of denaturation, primer annealing and polymerase extension can be repeated many times. Each round of denaturation, annealing and extension constitutes one "cycle." There can be numerous cycles, and the amount of amplified DNA produced increases with the number of cycles. Hence, to obtain a high concentration of an amplified target nucleic acid, many cycles are performed.

The steps involve in PCR nucleic acid amplification method are described in more detail below. For ease of discussion, the nucleic acid to be amplified is described as being double-stranded. However, the process is equally useful for amplifying a single-stranded nucleic acid, such as an mRNA, although the ultimate product is generally double-stranded DNA. In the amplification of a single-stranded nucleic acid, the first step involves the synthesis of a complementary strand (one of the two amplification primers can be used for this purpose), and the succeeding steps proceed as follows:

(a) contacting each nucleic acid strand with four different nucleoside triphosphates and one oligonucleotide primer for each strand of the specific sequence being amplified, wherein each primer is selected to be substantially complementary to the different strands of the specific sequence, such that the extension product synthesized from one primer, when it is separated from its complement, can serve as a template for synthesis of the extension product of the other primer, such contacting being at a temperature that allows hybridization of each primer to a complementary nucleic acid strand;

(b) contacting each nucleic acid strand; at the same time as or after step (a), with a nucleic acid polymerase of the invention that enables combination of the nucleoside triphosphates to form primer extension products complementary to each strand of the specific nucleic acid sequence;

(c) maintaining the mixture from step (b) at an effective temperature for an effective time to promote the activity of the enzyme and to synthesize, for each different sequence being amplified, an extension product of each primer that is complementary to each nucleic acid strand template, but not so high as to separate each extension product from the complementary strand template;

(d) heating the mixture from step (c) for an effective time and at an effective temperature to separate the primer extension products from the templates on which they were synthesized to produce single-stranded molecules but not so high as to denature irreversibly the enzyme;

(e) cooling the mixture from step (d) for an effective time and to an effective temperature to promote hybridization of a primer to each of the single-stranded molecules produced in step (d); and (f) maintaining the mixture from step (e) at an effective temperature for an effective time to promote the activity of the enzyme and to synthesize, for each different sequence being amplified, an extension product of each primer that is complementary to each nucleic acid template produced in step (d) but not so high as to separate each extension product from the complementary strand template. The effective times and temperatures in steps (e) and (f) may coincide, so that steps (e) and (f) can be carried out simultaneously. Steps (d)-(f) are repeated until the desired level of amplification is obtained.

The amplification method is useful not only for producing large amounts of a specific nucleic acid sequence of known sequence but also for producing nucleic acid sequences that are known to exist but are not completely specified. One need know only a sufficient number of bases at both ends of the sequence in sufficient detail so that two oligonucleotide primers can be prepared that will hybridize to different strands of the desired sequence at relative positions along the sequence such that an extension product synthesized from one primer, when separated from the template (complement), can serve as a template for extension of the other primer. The greater the knowledge about the bases at both ends of the sequence, the greater can be the specificity of the primers for the target nucleic acid sequence.

Thermally stable nucleic acid polymerases are therefore generally used for PCR because they can function at the high temperatures used for melting double stranded target DNA and annealing the primers during each cycle of the PCR reaction. High temperature results in thermodynamic conditions that favor primer hybridization with the target sequences and not hybridization with non-target sequences (H. A. Erlich (ed.), PCR Technology, Stockton Press [1989]).

The thermostable nucleic acid polymerases of the present invention satisfy the requirements for effective use in amplification reactions such as PCR. The present polymerases do not become irreversibly denatured (inactivated) when subjected to the required elevated temperatures for the time necessary to melt double-stranded nucleic acids during the amplification process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically denaturation can be done at temperatures ranging from about 90 EC to about 105 EC. The time required for denaturation depends mainly on the temperature and the length of the duplex nucleic acid. Typically the time needed for denaturation ranges from a few seconds up to four minutes. Higher temperatures may be required as the salt concentration of the buffer, or the length and/or GC composition of the nucleic acid is increased. The nucleic acid polymerases of the invention do not become irreversibly denatured for relatively short exposures to temperatures of about 90 EC to 100 EC.

The thermostable polymerases of the invention have an optimum temperature at which they function that is higher than about 45 EC. Temperatures below 45 EC facilitate hybridization of primer to template, but depending on salt composition and concentration and primer composition and length, hybridization of primer to template can occur at higher temperatures (e.g., 45 EC to 70 EC), which may promote specificity of the primer hybridization reaction. The polymerases of the invention exhibit activity over a broad temperature range from about 37 EC to about 90 EC.

The present polymerases have particular utility for PCR not only because of their thermal stability but also because of their ability to synthesize DNA using an RNA template and because of their fidelity in replicating the template nucleic acid. In most PCR reactions that start with an RNA template, reverse transcriptase must be added. However, use of reverse transcriptase has certain drawbacks. First, it is not stable at higher temperatures. Hence, once the initial complementary DNA (cDNA) has been made by reverse transcriptase and the thermal cycles of PCR are started, the original RNA template is not used as a template in the amplification reaction. Second, reverse transcriptase does not produce a cDNA copy with particularly good sequence fidelity. With PCR, it is possible to amplify a single copy of a specific target or template nucleic acid to a level detectable by several different methodologies. However, if the sequence of the target nucleic acid is not replicated with fidelity, then the amplified product can include a pool of nucleic acids with diverse sequences. Hence, the nucleic acid polymerases of the invention that can accurately reverse transcribe RNA and replicate the sequence of the template RNA or DNA with high fidelity is highly desirable.

Any nucleic acid can act as a "target nucleic acid" for the PCR methods of the invention. The term "target," when used in reference to the polymerase chain reaction, refers to the region of nucleic acid bounded by the primers used for polymerase chain reaction. In addition to genomic DNA and mRNA, any cDNA, RNA, oligonucleotide or polynucleotide can be amplified with the appropriate set of primer molecules. In particular, the amplified segments created by the PCR process itself are, themselves, efficient templates for subsequent PCR amplifications. The length of the amplified segment of the desired target sequence is determined by the relative positions of the primers with respect to each other, and therefore, this length is readily controlled.

The amplified target nucleic acid can be detected by any method known to one of skill in the art. For example, target nucleic acids are often amplified to such an extent that they form a band visible on a size separation gel. Target nucleic acids can also be detected by hybridization with a labeled probe; by incorporation of biotinylated primers during PCR followed by avidin-enzyme conjugate detection; by incorporation of $^{32}$P-labeled deoxynucleotide triphosphates during PCR, and the like.

The amount of amplification can also be monitored, for example, by use of a reporter-quencher oligonucleotide as described in U.S. Pat. No. 5,723,591, and a nucleic acid polymerase of the invention that has 5'-3' nuclease activity. The reporter-quencher oligonucleotide has an attached reporter molecule and an attached quencher molecule that is capable of quenching the fluorescence of the reporter molecule when the two are in proximity Quenching occurs when the reporter-quencher oligonucleotide is not hybridized to a complementary nucleic acid because the reporter molecule and the quencher molecule tend to be in proximity or at an optimal distance for quenching. When hybridized, the reporter-quencher oligonucleotide emits more fluorescence than when unhybridized because the reporter molecule and the quencher molecule tend to be further apart. To monitor amplification, the reporter-quencher oligonucleotide is designed to hybridize 3' to an amplification primer. During amplification, the 5'-3' nuclease activity of the polymerase digests the reporter oligonucleotide probe, thereby separating the reporter molecule from the quencher molecule. As the amplification is conducted, the fluorescence of the reporter molecule increases. Accordingly, the amount of amplification performed can be quantified based on the increase of fluorescence observed.

Oligonucleotides used for PCR primers are usually about 9 to about 75 nucleotides, preferably about 17 to about 50 nucleotides in length. Preferably, an oligonucleotide for use in PCR reactions is about 40 or fewer nucleotides in length (e.g., 9, 12, 15, 18, 20, 21, 24, 27, 30, 35, 40, or any number between 9 and 40). Generally specific primers are at least about 14 nucleotides in length. For optimum specificity and cost effectiveness, primers of 16-24 nucleotides in length are generally preferred.

Those skilled in the art can readily design primers for use processes such as PCR. For example, potential primers for nucleic acid amplification can be used as probes to determine whether the primer is selective for a single target and what conditions permit hybridization of a primer to a target within a sample or complex mixture of nucleic acids.

The present invention also contemplates use of the present nucleic acid polymerases in combination with other procedures or enzymes. For example, the polymerases can be used in combination with additional reverse transcriptase or another DNA polymerase. See U.S. Pat. No. 5,322,770, incorporated by reference herein.

In another embodiment, nucleic acid polymerases of the invention with 5'-3' exonuclease activity are used to detect target nucleic acids in an invader-directed cleavage assay. This type of assay is described, for example, in U.S. Pat. No. 5,994,069. It is important to note that the 5'-3' exonuclease of DNA polymerases is not really an exonuclease that progressively cleaves nucleotides from the 5' end of a nucleic acid, but rather a nuclease that can cleave certain types of nucleic acid structures to produce oligonucleotide cleavage products. Such cleavage is sometimes called structure-specific cleavage.

In general, the invader-directed cleavage assay employs at least one pair of oligonucleotides that interact with a target nucleic acid to form a cleavage structure for the 5'-3' nuclease activity of the nucleic acid polymerase. Distinctive cleavage products are released when the cleavage structure is cleaved by the 5'-3' nuclease activity of the polymerase. Formation of such a target-dependent cleavage structure and the resulting cleavage products is indicative of the presence of specific target nucleic acid sequences in the test sample.

Therefore, in the invader-directed cleavage procedure, the 5'-3' nuclease activity of the present polymerases is needed as well at least one pair of oligonucleotides that interact with a target nucleic acid to form a cleavage structure for the 5'-3' nuclease. The first oligonucleotide, sometimes termed the "probe," can hybridize within the target site but downstream of a second oligonucleotide, sometimes termed an "invader" oligonucleotide. The invader oligonucleotide can hybridize adjacent and upstream of the probe oligonucleotide. However, the target sites to which the probe and invader oligonucleotides hybridize overlap such that the 3' segment of the invader oligonucleotide overlaps with the 5' segment of the probe oligonucleotide. The 5'-3' nuclease of the present polymerases can cleave the probe oligonucleotide at an internal site to produce distinctive fragments that are diagnostic of the presence of the target nucleic acid in a sample. Further details and methods for adapting the invader-directed cleavage assay to particular situations can be found in U.S. Pat. No. 5,994,069.

One or more nucleotide analogs can also be used with the present methods, kits and with the nucleic acid polymerases. Such nucleotide analogs can be modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to targets present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

The invention also provides kits that contain at least one of the nucleic acid polymerases of the invention. Individual kits may be adapted for performing one or more of the following procedures: DNA sequencing, DNA amplification, RNA Amplification and/or primer extension. Kits of the invention comprise a DNA polymerase polypeptide of the invention and at least one nucleotide. A nucleotide provided in the kits of the invention can be labeled or unlabeled. Kits preferably can also contain instructions on how to perform the procedures for which the kits are adapted.

Optionally, the subject kit may further comprise at least one other reagent required for performing the method the kit is adapted to perform. Examples of such additional reagents include: another unlabeled nucleotide, another labeled nucleotide, a balance mixture of nucleotides, one or more chain terminating nucleotides, one or more nucleotide analogs, buffer solution(s), magnesium solution(s), cloning vectors, restriction endonucleases, sequencing primers, reverse transcriptase, and DNA or RNA amplification primers. The reagents included in the kits of the invention may be supplied in premeasured units so as to provide for greater precision and accuracy. Typically, kits reagents and other components are placed and contained in separate vessels. A reaction vessel, test tube, microwell tray, microtiter dish or other container can also be included in the kit. Different labels can be used on different reagents so that each reagent can be distinguished from another.

The following Examples further illustrate the invention and are not intended to limit the scope of the invention.

EXAMPLE 1

Cloning of *Thermus scotoductus*, Strain X-1 Polymerase

Growth of Bacteria and Genomic DNA Isolation

*Thermus scotoductus* (Tsc) strain X-1 was obtained from ATCC (ATCC Deposit No. 27978). The lyophilized bacteria were revived in ATCC Culture Medium 461 (Castenholz TYE medium) and grown overnight to stationary phase. *Thermus scotoductus* genomic DNA was prepared using a Quiagen genomic DNA preparation protocol and kit (Quiagen).

Cloning Methods

The first forward and reverse primers were designed by analysis of 5' and 3' terminal homologous conserved regions of the DNA sequences of *Thermus aquaticus* (Taq), *Thermus thermophilus* (Tth), *Thermus filiformis* (Tfi), *Thermus caldophilus* (that was determined to actually be Tth strain GK24), and *Thermus flavus* (believed to be *Thermus igniterrae*). A fragment of a *Thermus scotoductus* polymerase gene was amplified using N-terminal primer 5'-ggc cac cac ctg gcc tac-3' (SEQ ID NO:29) and C-terminal primer 5'-ccc acc tcc acc tcc ag-3' (SEQ ID NO:30). The following PCR reaction mixture contained 2.5 μl of 10×Amplitaq buffer (ABi), 2 mM MgCl, 60 ng DNA template, 2.5 mM (each) dNTP, 20 pmol of each primer, and 1.25 units of Amplitaq DNA polymerase in a 25 μl total reaction volume.

The reaction mixture was heated to 80° C. and then the primers were added. This was followed by a predenaturation step (96° C. for 30 s); PCR cycling for 30 cycles (97° C. for 3 s, 56° C. for 30 s, 72° C. for 3 min) with a finishing step (72° C. for 7 min). This produced an approximate 1.5 kb DNA fragment that was cloned and sequenced. This cloned fragment showed some homology to the Tth Polymerase I gene (Genebank accession number 466573) between nucleotide numbers 644 and 1973.

Direct sequencing of the genomic DNA was used to obtain the sequence of the 5' terminus of the *Thermus scotoductus* polymerase gene. The primer used was 5'-ctg gcc atg ctg aag ctc ttt-3' (SEQ ID NO:31) and a 2-step thermocycling protocol. A predenaturation step (95° C. for 5 min) was followed by 80 cycles (97° C. for 5 sec, 60° C. for 4 min) Reaction mixture consisted of 16 μl Big Dye V1 Ready Reaction mix, 2.8 ug DNA, 15 pmol primer in a 40 μl total reaction volume. The sequencing of the *Thermus scotoductus* gene from genomic DNA revealed that the 5' terminal sequence of the wild-type *Thermus scotoductus* gene is 5'-ata agg gcg atg ctg ccc ctc ttt gag-5' (SEQ ID NO:32) that would indicate that the ATG is the start codon of the wild-type gene. However, the N-terminus of Taq, Tth and Tfi enzymes have two methionine amino acid residues at their N terminal end separated by two amino acids. In order to make the *Thermus scotoductus* N-terminus more similar to the other known *Thermus* DNA polymerases, and possibly to improve protein translation efficiency, the ATA codon was changed to ATG. This introduced an additional start for protein translation making the recombinant protein N terminus MRAM. The amplification of the full-length *Thermus scotoductus* nucleic acid polymerase coding region was carried out using the 5' forward primer 5'-cat atg agg gcg atg ctg ccc ctc-3' (SEQ ID NO:33). Another consideration when designing this primer was to introduce a recognition site for the restriction enzyme Nde I (catatg, SEQ ID NO:34). This sequence was introduced to facilitate subcloning of the coding region into other plasmid vectors.

As described above, the first cloned portion of the *Thermus scotoductus*, strain X-1 polymerase gene was only 1.2 kb. This represented approximately half of the full-length gene. In order to obtain a larger fragment of the *Thermus scotoductus* gene, a PCR reaction was carried out using the 5' forward primer (SEQ ID NO:33) described in the previous paragraph and a new primer designed near the same homologous 3' region of the known *Thermus* polymerase genes. The sequence of this primer was 5'-ctc cac ctc cag ggg cac-3' (SEQ ID NO:35). The PCR reaction was the same mixture as above. The cycling conditions were altered slightly in order to promote greater specificity. The reaction mixture was heated to 80° C. and then the primers were added. This was followed by a predenaturation step (96° C. for 2 min); PCR cycling for 10 cycles (97° C. for 10 s, 70° C. for 3 min), 25 cycles (97° C. for 10 s, 60° C. for 3 min), with a finishing step (72° C. for 7 min). This produced a 2.4 kb fragment that was cloned and sequenced. This left to be sequenced a short 3' terminal region of the *Thermus scotoductus*, strain X-1 polymerase gene.

Based on the additional sequence of the larger fragment of the *Thermus scotoductus* polymerase gene, a new primer was designed to obtain the remaining unknown 3' sequence: 5'-ctg gcc atg gtg aag ctc ttt-3' (SEQ ID NO:36). The genomic sequencing protocol was the same as described for the previous genomic DNA sequencing reaction for the 5' terminus. Once the sequence was obtained, a primer was designed to be used with the 5' terminal primer described above to amplify the full length *Thermus scotoductus* polymerase gene. This primer is complementary to the 3' terminal sequence. It also has a Sal I recognition site (gtcgac, SEQ ID NO:37) overlapping with the stop codon. This restriction site will facilitate subcloning into other plasmid DNA vectors. The sequence of the primer is 5'-gtc gac tag gcc ttg gcg aaa gcc a-3' (SEQ ID NO:38).

Three different cloned *Thermus scotoductus* polymerase genes were sequenced independently in order to rule out PCR errors. The resulting consensus sequence is the natural *Thermus scotoductus* polymerase gene sequence of this invention (SEQ ID NO:14). The amino acid numbering used in this description of the invention is based on a recombinant form of the *Thermus scotoductus* polymerase protein that has an additional three amino acids at its N-terminus (SEQ ID NO:13). However, SEQ ID NO:14 is the sequence for the wild type *Thermus scotoductus* polymerase from strain X-1.

The amino acid sequence of the strain X-1 *Thermus scotoductus* polymerase has several differences when compared with the amino acid sequence of *Thermus aquaticus* DNA Polymerase, including about 51 conservative amino acid changes and about 62 nonconservative amino acid changes. For example, one region of dissimilarity is between amino acid positions at approximately 51 and about 65, where the sequence of the *Thermus scotoductus* polymerase has about four amino acid changes (in bold): LLKALREDG DVVIVVFDAK APSFRHQTYE (SEQ ID NO:39). Another region of dissimilarity is between amino acid positions at approximately 201 and about 236, where the sequence of the *Thermus scotoductus* polymerase has about seven amino acid changes (in bold): GEKTAAKLIREWGSLENLLKHLEQV KPASV REKILS (SEQ ID NO:40). Another region of dissimilarity is between amino acid positions at approximately 311 and about 350, where the sequence of the *Thermus scotoductus* polymerase has about seven amino acid changes (in bold): VGYVLSRPEPMWAELN ALAAAWEGRVYRAEDPLEALRGLG (SEQ ID NO:41). Another region of dissimilarity is between amino acid positions at approximately 415 and about 435, where the sequence of the *Thermus scotoductus* polymerase has about five amino acid changes (in bold): RLYAALLERLKGEERLLWLYE (SEQ ID NO:42). Another region of dissimilarity is between amino acid positions at approximately 531 and about 562, where the sequence of the *Thermus scotoductus* polymerase has about six amino acid changes (in bold): PIVDRILQYRELSKLK GTYID PLPALVHPKTN (SEQ ID NO:43). Another region of dissimilarity is between amino acid positions at approximately 801 and about 836, where the sequence of the *Thermus scotoductus* polymerase has about eight amino acid changes (in bold): EEVAQEAKRT MEEVWPLKVPLEVEVGIGEDWLSAKA (SEQ ID NO:44). Hence, many regions of the *Thermus scotoductus* polymerase differ from the *Thermus aquaticus* and *Thermus thermophilus* DNA Polymerases.

Modification of Strain X-1 Polymerase Wild-Type Gene

In order to produce *Thermus scotoductus* polymerase in a form suitable for dye-terminator DNA sequencing, two amino acid substitutions were made. These are the FS (Tabor and Richardson, 1995 PNAS 92: 6339-6343) and exo-minus (G46D mutation) mutations. To reduce the exonuclease activity to very low levels, the mutation G46D was introduced. To reduce the discrimination between ddNTP's and dNTP's, the mutation F666Y was introduced.

Mutagenesis was carried out using the modified QuickChange™ (Stratagene) PCR mutagenesis protocol described in Sawano & Miyawaki (2000), Nucleic Acids Research Vol. 28. The mutated gene was resequenced completely to confirm the introduction of the mutations and to ensure that no PCR errors were introduced.

The *Thermus scotoductus*, strain X-1, polymerase gene (FS, exoΓ) was removed from the cloning vector by restriction digest with NdeI and SalI. The 2.4 kb gene was ligated into the pT7 expression vector (Brookhaven National Laboratories, Long Island, N.Y.). This resulting vector containing the *Thermus scotoductus* polymerase (fs, exoΓ) gene was used to transform BL21 *E. coli* cells (Invitrogen).

EXAMPLE 2

*Thermus scotoductus*, Strain X-1 Polymerase Expression and Purification

BL21 *E. coli* cells (Invitrogen) containing the pT7 expression vector with the *Thermus scotoductus*, strain X-1 polymerase coding region were grown in one liter of Terrific Broth (Maniatis) to an optical density of 1.2 OD and the polymerase protein was overproduced by four-hour induction with 1.0 mM IPTG. The cells were harvested by centrifugation, washed in 50 mM Tris (pH 7.5), 5 mM EDTA, 5% glycerol, 10 mM EDTA to remove growth media, and the cell pellet frozen at −80° C.

To isolate the *Thermus scotoductus*, strain X-1 polymerase, the cells were thawed and resuspended in 2.5 volumes (wet weight) of 50 mM Tris (pH 7.2), 400 mM NaCl, 1 mM EDTA. The cell walls were disrupted by sonication and the resulting *E. coli* cell debris were removed by centrifugation. The resulting lysate was pasteurized in a water bath (75° C. for 45 min), denaturing and precipitating the majority of the non-thermostable *E. coli* proteins and leaving the thermostable *Thermus scotoductus*, strain X-1 polymerase in solution. *E. coli* genomic DNA was removed by coprecipitation with 0.3% Polyethyleneimine (PEI). The cleared lysate is then applied to two columns in series: (1) a Biorex 70 cation exchange resin that chelates excess PEI and (2) a heparin-agarose column (dimensions to be provided) that retains the polymerase. This column is washed with 5 column volumes of 20 mM Tris (pH 8.5), 5% glycerol, 100 mM NaCl, 0.1 mM EDTA, 0.05% Triton X-100 and 0.05% Tween-20 (KTA). The protein was then eluted with a 0.1 to 1.0M NaCl linear gradient. The polymerase eluted at 0.8M NaCl. The eluted Tsc Polymerase was concentrated and the buffer exchanged using a Millipore concentration filter (30 kD M.W. cutoff). The concentrated protein was stored at in KTA (no salt) plus 50% glycerol at −20° C.

The activity of the polymerase was measured using the standard salmon sperm DNA radiometric activity assay and sequencing was tested using the Big Dye Version 3. The enzyme is active in 40-80 mM Tris, 1.0-2.0 mM MgCl at a dNTP mix consisting of 0.2 mM dATP, 0.2 mM dCTP, 0.2 mM dUTP, and 0.3 mM dITP, at pH 8.0-10.0, with optimal activity between pH 9.0 and 9.58. The enzyme is also active in KCl concentrations from 0 to 100 mM, indicating that the *T. scotoductus*, strain X-1 polymerase is more salt-tolerant than either Tfil or Taq, but not quite as salt-tolerant as Tth.

EXAMPLE 3

*Thermus scotoductus* Strains SM3 and Vi7a

The same primers used to amplify the full-length gene encoding the polymerase from *Thermus scotoductus* (Tsc) strain X-1 were used to amplify the polymerase genes from two additional strains of *Thermus scotoductus*: strain SM3 and strain Vi7a. The PCR reaction mixture used to amplify nucleic acids encoding the *Thermus scotoductus* polymerase from strains SM3 and Vi7a contained 2.5 μl of 10×Amplitaq reaction buffer (Applied Biosystems), 2 mM $MgCl_2$, 70 to 100 ng genomic DNA template, 0.2 mM (each) dNTPs, 20 pmol of each primer, and 1.25 units of Amplitaq in a 25 μl total reaction volume. The reaction was started by adding a premix containing enzyme, $MgCl_2$, dNTPs, buffer and water to another premix containing primer and template preheated at 80° C. The entire reaction mixture was then denatured (30 sec at 96° C.) followed by 30 PCR cycles (97° C. for 3 sec, 62° C. for 30 sec, 72° C. for 3 min) with a finishing step (72° C. for 7 min).

These PCR reactions each produced approximate 2.5 kb DNA fragments. The amplified fragments were purified from the PCR reaction mixes using a Quiagen PCR cleanup kit (Quiagen). The *Thermus scotoductus* fragments were ligated into the inducible expression vector pCR®4-TOPO® (Invitrogen, Carlsbad, Calif.). Three different cloned *Thermus scotoductus* polymerase genes from each strain were sequenced independently in order to rule out PCR errors. The resulting consensus sequences for the wild-type genes are reported in FIGS. 1 and 3 below.

There are several silent changes at the DNA level among the three genes. Only the changes resulting in a different amino acid are noted in the alignment of amino acid sequences provided in FIG. 2. The *Thermus scotoductus*, strain SM3 polymerase has five positions that have different amino acids compared to strain X-1. The *Thermus scotoductus* strain Vi7a polymerase has four differences when compared to the amino acid sequence of the polymerase from strain X-1. These are indicated with boldface in FIG. 2.

Modification of Polymerases from Strains SM3 and Vi7a

In order to produce the polymerases from *Thermus scotoductus* strains SM3 and Vi7a in a form suitable for dye-terminator DNA sequencing, two amino acid substitutions were made in each gene. These are the FS mutation (U.S. Pat. No. 5,614,365; Tabor and Richardson, 1995 PNAS 92: 6339-6343) and exo-minus mutation (G46D Patent, Joyce papers) that were described in the patent application. As described previously, mutagenesis was carried out using the modified QuickChange™ (Stratagene) PCR mutagenesis protocol described in Sawano & Miyawaki (2000), Nucleic Acids Research Vol. 28. The mutated genes was resequenced completely to confirm the introduction of the mutations and to ensure that no PCR errors were introduced.

Protein Expression and Purification

The "FS, exo-minus form of both *Thermus scotoductus* polymerase genes were subcloned into the pet expression vector using the NdeI and Sal I restriction sites. BL21 cells (Invitrogen) were transformed with this expression construct. The cells were grown in one liter of Terrific Broth (Maniatis)

to an optical density of 1.2 OD and the proteins were overproduced by four-hour induction with 1.0 mM IPTG. The cells were harvested by centrifugation, washed in 50 mM Tris (pH 7.5), 5 mM EDTA, 5% glycerol, 10 mM EDTA to remove growth media, and the cell pellet frozen at −80° C.

To isolate the *Thermus scotoductus*, strain SM3 and Vi7a polymerases, the cells were thawed and resuspended in 2.5 volumes (wet weight) of 50 mM Tris (pH 7.2), 400 mM NaCl, 1 mM EDTA. The cell walls were disrupted by sonication and the resulting *E. coli* cell debris was removed by centrifugation. The resulting lysate was pasteurized in a water bath (75° C. for 45 min), denaturing and precipitating the majority of the non-thermostable *E. coli* proteins and leaving the thermostable *Thermus scotoductus* polymerase in solution. *E. coli* genomic DNA was removed by coprecipitation with 0.3% Polyethyleneimine (PEI). The cleared lysate was then applied to two columns in series: (1) a Biorex 70 cation exchange resin that chelates excess PEI and (2) a heparin-agarose column that retains the polymerase. This column was washed with 5 column volumes of 20 mM Tris (pH 8.5), 5% glycerol, 100 mM NaCl, 0.1 mM EDTA, 0.05% Triton X-100 and 0.05% Tween-20 (KTA). The proteins were then eluted with a 0.1 to 1.0M NaCl linear gradient. The polymerases eluted at 0.8M NaCl. The eluted *Thermus scotoductus* polymerases were concentrated and the buffer exchanged using a Millipore concentration filter (30 kD M.W. cutoff). The concentrated proteins were stored at in KTA (no salt) plus 50% glycerol at −20° C.

The activity of the polymerases were measured using a nicked salmon sperm DNA radiometric activity assay. Both enzymes are being tested for use in sequencing using the Big Dye™ V 3.0. The enzymes are active in 40-80 mM Tris, 1.0-2.0 mM MgCl at a dNTP mix consisting of 0.2 mM dATP, 0.2 mM dCTP, 0.2 mM dUTP, and 0.3 mM dITP, at pH 8.0-10.0, with optimal activity between pH 9.0 and 9.58.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant arts are intended to be within the scope of the following claims.

SEQUENCE LISTING

<160> NUMBER OF SEQ ID NOS: 50

<210> SEQ ID NO 1
<211> LENGTH: 2502
<212> TYPE: DNA
<213> ORGANISM: Thermus scotoductus

<400> SEQUENCE: 1

```
atgagggcga tgctgcccct ctttgagccc aagggccggg tgcttctggt ggacggccac     60
cacctggcct accgtacctt ttttgccctg aagggcctca ccaccagccg cggggagccg    120
gtccaggcgg tgtacgggtt tgccaagagc cttttgaagg cgctaaggga agacggggat    180
gtggtgatcg tggtgtttga cgccaaggcc ccctccttcc gccaccagac ctacgaggcc    240
tacaaggcgg ggcgggctcc cacccccgag gactttcccc ggcagcttgc ccttatcaag    300
gagatggtgg accttttggg cctggagcgc ctcgaggtgc cgggctttga ggcggatgac    360
gtcctggcta ccctggccaa gaaggcggaa aaggaaggct acgaggtgcg catcctcacc    420
gcggaccggg acctttacca gcttctttcg gagcgaatct ccatccttca cccggagggt    480
tacctgatca ccccggagtg gctttgggag aagtatgggc ttaagccttc ccagtgggtg    540
gactaccggg ccttggccgg ggacccttcc gacaacatcc ccggcgtgaa gggcatcggg    600
gagaagacgg cggccaagct gatccgggag tggggaagcc tggaaaacct tcttaagcac    660
ctggaacagg tgaaacctgc ctccgtgcgg gagaagatcc ttagccacat ggaggacctc    720
aagctatccc tggagctatc ccgggtgcgc acggacttgc cccttcaggt ggacttcgcc    780
cggcgccggg agccggaccg ggaggggctt aaggcctttt tggagaggct ggagttcgga    840
agcctcctcc acgagttcgg cctgttggaa agcccggtgg cggcggagga agctccctgg    900
ccgccccccg agggagcctt cgtggggtac gttctttccc gccccgagcc catgtgggcg    960
gagcttaacg ccttggccgc cgcctgggag ggaagggttt accgggcgga ggatcccttg   1020
gaggccttgc gggggcttgg ggaggtgagg gggcttttgg ccaaggacct ggcggtgctg   1080
gccctgaggg aagggattgc cctggcaccg ggcgacgacc ccatgctcct cgcctacctc   1140
```

-continued

```
ctggatcctt ccaacaccgc ccccgaaggg gtagcccggc gctacggggg ggagtggacc   1200
gaggaggcgg gggaaagggc gttgctttcc gaaaggcttt acgccgccct cctggagcgg   1260
cttaaggggg aggagaggct tctttggctt tacgaggagg tggaaaagcc cctttcgcgg   1320
gtcctggccc acatggaggc cacgggggta cggttggatg tggcctactt aaaggccctt   1380
tccctggagg tggaggcgga gctcaggcgc ctcgaggagg aggtccaccg cctggccggg   1440
catcctttca acctgaactc ccgggaccag ctggaaaggg tcctctttga cgagcttggg   1500
cttcccgcca tcggcaagac ggagaagacg ggcaagcgct ccaccagcgc cgccgttttg   1560
gaggccttgc gggaggctca tcccatcgtg gaccgcatcc ttcagtaccg ggagctttcc   1620
aagctcaagg gaacctacat cgatcccttg cctgccctgg tccaccccaa gacgaaccgc   1680
ctccacaccc gtttcaacca gacggccacc gccacgggga ggcttagcag ctcggatccc   1740
aacctgcaaa atatccccgt gcgcacccct ttgggccagc ggatccgccg ggccttcgtg   1800
gccgaggagg ggtggaggct ggtggttttg gactacagcc agattgagct cagggtcctg   1860
gcgcaccttt ccggggacga gaacctaatc cgggtcttcc aggagggcca ggacatccac   1920
acccagacgg ccagctggat gttcggcgtg cccccagagg ccgtggattc cctgatgcgt   1980
cgggcggcca agaccatcaa cttcggcgtc ctctacggca tgtccgccca ccggctttcg   2040
ggagagctgg ccatccccta cgaggaggcg gtggccttca tcgagcggta tttccagagc   2100
taccccaagg tgcgggcctg gattgagaaa accctggcgg aaggacggga acggggctat   2160
gtggaaaccc tctttggccg ccggcgctac gtgcccgact tggcttcccg ggtgaagagc   2220
atccgggagg cagcggagcg catggccttc aacatgccgg tccaggggac cgccgcggat   2280
ttgatgaaac tggccatggt gaagctcttt cccaggcttc aggagctggg ggccaggatg   2340
cttttgcagg tgcacgacga actggtcctc gaggctccca aggagcaagc ggaggaagtc   2400
gcccaggagg ccaagcggac catggaggag gtgtggcccc tgaaggtgcc cttggaggtg   2460
gaagtgggca tcggggagga ctggctttcc gccaaggcct ag                      2502
```

<210> SEQ ID NO 2
<211> LENGTH: 2507
<212> TYPE: DNA
<213> ORGANISM: Thermus scotoductus

<400> SEQUENCE: 2

```
atgagggcga tgctgcccct ctttgagccc aagggccggg tgcttctggt ggacggccac     60
cacctggcct accgtacctt ttttgccctg aagggcctca ccaccagccg cggggagccg    120
gtccaggcgg tgtacgggtt tgccaagagc cttttgaagg cgctaaggga agacggggat    180
gtggtgatcg tggtgtttga cgccaaggcc ccctccttcc gccaccagac ctacgaggcc    240
tacaaggcgg ggcgggctcc cacccccgag gactttcccc ggcagcttgc ccttatcaag    300
gagatggtgg acctttttggg cctggagcgc ctcgaagtgc cgggttttga ggcggatgac    360
gtcctggcca ccctggccaa gaaggcggaa aaggaaggct acgaggtgcg catcctcacc    420
gcggaccggg acctttacca gcttctttcg gaccgaatct ccatccttca cccggagggt    480
tacctgatca ccccggagtg gctttgggag aagtatgggc ttaagccttc ccagtgggtg    540
gactaccggg ccttggccgg ggacccttcc gacaacatcc ccggcgtgaa gggcatcggg    600
gagaagacgg cggccaagct gatccgggag tggggaagcc tggaaaacct tcttaagcac    660
ctggaacagg tgaaacctgc ctccgtgcgg gagaagatcc ttagccacat ggaggacctc    720
aagctatccc tggagctttc ccgggtgcac acggagttgc cccttcaggt ggacttcgcc    780
```

```
cggcgccggg agccggaccg ggaagggctt aaggcctttt tggagaggct ggagttcgga    840

agcctcctcc acgagttcgg cctgttggaa agcccggtgg cggcggagga agctccctgg    900

ccgccccccg agggagcctt cgtggggtac gttctttccc gccccgagcc catgtgggcg    960

gagcttaacg ccttggccgc cgcctgggag ggaagggttt accgggcgga ggatcccttg   1020

gaggccttgc gggggcttgg ggaggtgagg gggcttttgg ccaaggacct ggcggtgctg   1080

gccctgaggg aagggattgc cctggcacag ggcgacgacc ccatgctcct cgcctacctc   1140

ctggatcctt ccaacaccgc ccccgaaggg gtagcccggc gctacggggg ggagtggacc   1200

gaggaggcgg gggaaagggc gctgctttcc gaaaggcttt acgccgccct cctggagcgg   1260

cttaaggggg aggagaggct tctttggctt tacgaggagg tggaaaagcc cctttcgcgg   1320

gtcctggccc acatggaggc cacgggggta tggttggatg tggcctactt gaaggccctt   1380

tccctggagg tggaggcgga gctcaggcgc ctcgaggagg aggtccaccg actggccggg   1440

catcctttca acctgaactc ccgggaccag ctggaaaggg tcctctttga cgagcttggg   1500

cttcccgcca tcggcaagac ggagaagacg ggtaagcgtt ccaccagcgc cgccgttttg   1560

gaggctttga gggaggctca tcccatagtg gaccgcatcc tccagtaccg ggagctttcc   1620

aagctcaagg gaacgtacat cgatcccttg cccgccctgg tccaccccaa gacgaaccgc   1680

ctccacaccc gtttcaacca gacggccacc gccacgggga ggcttagcag ctcggatccc   1740

aacctgcaaa atatccccgt gcgcacccct ttaggccagc ggatccgccg ggccttcgtg   1800

gccgaggagg ggtggaggct ggtggttttg gactacagcc agattgagct cagggtcctg   1860

gcgcaccttt ccggggacga gaacctgatc cgggtcttcc aagagggcca ggacatccac   1920

acccagacgg ccagctggat gttcggcgtg cccccagagg ccgtggattc cctgatgcgc   1980

cgggcggcca agaccatcaa cttcggcgtc ctctacggca tgtccgccca ccggctttcg   2040

ggagagctgg ccatccccta cgaggaagcg gtggccttca tcgagcggta tttccagagc   2100

taccccaagg tacgggcctg gattgagaaa accctggcgg aaggacggga gcggggctat   2160

gtggaaaccc tctttggccg ccggcgctat gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaggtgggta tcggggagga ctggctttcc gccaaggcct agtcgac                 2507
```

<210> SEQ ID NO 3
<211> LENGTH: 2507
<212> TYPE: DNA
<213> ORGANISM: Thermus scotoductus

<400> SEQUENCE: 3

```
atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgggtt tgccaagagc cttttgaagg cgctaaggga agacggggat    180

gtggtgatcg tggtgtttga cgccaaggcc ccctccttcc gccaccagac ctacgaggcc    240

tacaaggcgg ggcgggctcc cacccccgag gactttcccc ggcagcttgc ccttatcaag    300

gagatggtgg accttttggg cctggagcgc ctcgaagtgc cgggttttga ggcggatgac    360
```

-continued

```
gtcctggcca ccctggccaa gaaggcggaa aaggaaggct acgaggtgcg catcctcacc    420

gcggaccggg acctttacca gcttctttcg gaccgaatct ccatccttca cccggagggt    480

tacctgatta ccccggagtg gctttgggag aagtatgggc ttaagccttc ccagtgggtg    540

gactaccggg ccttggccgg ggacccttcc gacaacatcc ccggcgtgaa gggcatcggg    600

gagaagacgg cggccaagct gatccgggag tggggaagcc tggaaaacct tcttaagcac    660

ctggaacagg tgaaacctgc ctccgtgcgg gagaagatcc ttagccacat ggaggacctc    720

aagctatccc tggagctttc ccgggtgcac acggagttgc cccttcaggt ggacttcgcc    780

cggcgccggg agccggaccg ggaagggctt aaggcctttt tggagaggct ggagttcgga    840

agcctcctcc acgagttcgg cctgttggaa agcccggtgg cggcggagga agctccctgg    900

ccgccccccg agggagcctt cgtggggtac gttctttccc gccccgagcc catgtgggcg    960

gagcttaacg ccttggccgc cgcctgggag ggaagggttt accgggcgga ggatcccttg   1020

gaggccttgc gggggcttgg ggaggtgagg gggcttttgg ccaaggacct ggcggtgctg   1080

gccctgaggg aagggattgc cctggcaccg ggcgacgacc ccatgctcct cgcctacctc   1140

ctggatcctt ccaacaccgc ccccgaaggg gtagcccggc gctacggggg ggagtggacc   1200

gaggaggcgg gggaaagggc gctgctttcc gaaaggcttt acgccgccct cctggagcgg   1260

cttaaggggg aggagaggct tctttggctt tacgaggagg tggaaaagcc cctttcgcgg   1320

gtcctggccc acatggaggc cacgggggta tggttggatg tggcctactt gaaggccctt   1380

tccctggagg tggaggcgga gctcaggcgc ctcgaggagg aggtccaccg actggccggg   1440

catcctttca acctgaactc ccgggaccag ctggaaaggg tcctctttga cgagcttggg   1500

cttcccgcca tcggcaagac ggagaagacg ggtaagcgtt ccaccagcgc cgccgttttg   1560

gaggctttga gggaggctca tcccatagtg gaccgcatcc tccagtaccg ggagctttcc   1620

aagctcaagg gaacgtacat cgatcccttg cccgccctgg tccaccccaa gacgaaccgc   1680

ctccacaccc gtttcaacca gacggccacc gccacgggga ggcttagcag ctcggatccc   1740

aacctgcaaa atatccccgt gcgcacccct ttaggccagc ggatccgccg ggccttcgtg   1800

gccgaggagg ggtggaggct ggtggttttg gactacagcc agattgagct cagggtcctg   1860

gcgcaccttt ccggggacga gaacctgatc cgggtcttcc aagagggcca ggacatccac   1920

acccagacgg ccagctggat gttcggcgtg cccccagagg ccgtggattc cctgatgcgc   1980

cgggcggcca agaccatcaa ctacggcgtc ctctacggca tgtccgccca ccggctttcg   2040

ggagagctgg ccatccccta cgaggaagcg gtggccttca tcgagcggta tttccagagc   2100

ttccccaagg tacgggcctg gattgagaaa accctggcgg aaggacggga gcggggctat   2160

gtggaaaccc tctttggccg ccggcgctat gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaggtgggta tcggggagga ctggctttcc gccaaggcct agtcgac                 2507
```

<210> SEQ ID NO 4
<211> LENGTH: 2502
<212> TYPE: DNA
<213> ORGANISM: Artificial Sequence
<220> FEATURE:
<223> OTHER INFORMATION: A derivative nucleic acid related to Thermus -continued scotoductus, strain X-1, having GAC (encoding Asp) in place of GGG (encoding Gly) at positions 136-138.

<400> SEQUENCE: 4

```
atgagggcga tgctgcccct ctttgagccc aagggccggg tgcttctggt ggacggccac     60
cacctggcct accgtacctt ttttgccctg aagggcctca ccaccagccg cggggagccg    120
gtccaggcgg tgtacgactt tgccaagagc cttttgaagg cgctaaggga agacggggat    180
gtggtgatcg tggtgtttga cgccaaggcc ccctccttcc gccaccagac ctacgaggcc    240
tacaaggcgg ggcgggctcc cacccccgag gactttcccc ggcagcttgc ccttatcaag    300
gagatggtgg accttttggg cctggagcgc ctcgaggtgc cgggctttga ggcggatgac    360
gtcctggcta ccctggccaa gaaggcggaa aaggaaggct acgaggtgcg catcctcacc    420
gcggaccggg acctttacca gcttctttcg gagcgaatct ccatccttca cccggagggt    480
tacctgatca ccccggagtg gctttgggag aagtatgggc ttaagccttc ccagtgggtg    540
gactaccggg ccttggccgg ggacccttcc gacaacatcc ccggcgtgaa gggcatcggg    600
gagaagacgg cggccaagct gatccgggag tggggaagcc tggaaaacct tcttaagcac    660
ctggaacagg tgaaacctgc ctccgtgcgg gagaagatcc ttagccacat ggaggacctc    720
aagctatccc tggagctatc ccgggtgcgc acggacttgc cccttcaggt ggacttcgcc    780
cggcgccggg agccggaccg ggaggggctt aaggcctttt tggagaggct ggagttcgga    840
agcctcctcc acgagttcgg cctgttggaa agcccggtgg cggcggagga agctccctgg    900
ccgccccccg agggagcctt cgtggggtac gttctttccc gccccgagcc catgtgggcg    960
gagcttaacg ccttggccgc cgcctgggag ggaagggttt accgggcgga ggatcccttg   1020
gaggccttgc gggggcttgg ggaggtgagg gggcttttgg ccaaggacct ggcggtgctg   1080
gccctgaggg aagggattgc cctggcaccg ggcgacgacc ccatgctcct cgcctacctc   1140
ctggatcctt ccaacaccgc ccccgaaggg gtagcccggc gctacggggg ggagtggacc   1200
gaggaggcgg gggaaagggc gttgctttcc gaaaggcttt acgccgccct cctggagcgg   1260
cttaaggggg aggagaggct tctttggctt tacgaggagg tggaaaagcc cctttcgcgg   1320
gtcctggccc acatggaggc cacgggggta cggttggatg tggcctactt aaaggccctt   1380
tccctggagg tggaggcgga gctcaggcgc ctcgaggagg aggtccaccg cctggccggg   1440
catcctttca acctgaactc ccgggaccag ctggaaaggg tcctctttga cgagcttggg   1500
cttcccgcca tcggcaagac ggagaagacg ggcaagcgct ccaccagcgc cgccgttttg   1560
gaggccttgc gggaggctca tcccatcgtg gaccgcatcc ttcagtaccg ggagctttcc   1620
aagctcaagg gaacctacat cgatcccttg cctgccctgg tccaccccaa gacgaaccgc   1680
ctccacaccc gtttcaacca gacggccacc gccacgggga ggcttagcag ctcggatccc   1740
aacctgcaaa atatccccgt gcgcacccct ttgggccagc ggatccgccg ggccttcgtg   1800
gccgaggagg ggtggaggct ggtggttttg gactacagcc agattgagct cagggtcctg   1860
gcgcaccttt ccggggacga gaacctaatc cgggtcttcc aggagggcca ggacatccac   1920
acccagacgg ccagctggat gttcggcgtg cccccagagg ccgtggattc cctgatgcgt   1980
cgggcggcca agaccatcaa cttcggcgtc ctctacggca tgtccgccca ccggctttcg   2040
ggagagctgg ccatccccta cgaggaggcg gtggccttca tcgagcggta tttccagagc   2100
taccccaagg tgcgggcctg gattgagaaa accctggcgg aaggacggga acggggctat   2160
gtggaaaccc tctttggccg ccggcgctac gtgcccgact tggcttcccg ggtgaagagc   2220
```

atccgggagg cagcggagcg catggccttc aacatgccgg tccaggggac cgccgcggat 2280
ttgatgaaac tggccatggt gaagctcttt cccaggcttc aggagctggg ggccaggatg 2340
cttttgcagg tgcacgacga actggtcctc gaggctccca aggagcaagc ggaggaagtc 2400
gcccaggagg ccaagcggac catggaggag gtgtggcccc tgaaggtgcc cttggaggtg 2460
gaagtgggca tcggggagga ctggctttcc gccaaggcct ag 2502

<210> SEQ ID NO 5
<211> LENGTH: 2507
<212> TYPE: DNA
<213> ORGANISM: Artificial Sequence
<220> FEATURE:
<223> OTHER INFORMATION: A derivative nucleic acid related to Thermus scotoductus, strain SM3, having GAC (encoding Asp) in place of GGG (encoding Gly) at positions 136-138.

<400> SEQUENCE: 5
atgagggcga tgctgcccct ctttgagccc aagggccggg tgcttctggt ggacggccac 60
cacctggcct accgtacctt ttttgccctg aagggcctca ccaccagccg cggggagccg 120
gtccaggcgg tgtacgactt tgccaagagc cttttgaagg cgctaaggga agacggggat 180
gtggtgatcg tggtgtttga cgccaaggcc ccctccttcc gccaccagac ctacgaggcc 240
tacaaggcgg ggcgggctcc cacccccgag gactttcccc ggcagcttgc ccttatcaag 300
gagatggtgg accttttggg cctggagcgc ctcgaagtgc cgggttttga ggcggatgac 360
gtcctggcca ccctggccaa gaaggcggaa aaggaaggct acgaggtgcg catcctcacc 420
gcggaccggg acctttacca gcttctttcg gaccgaatct ccatccttca cccggagggt 480
tacctgatca ccccggagtg gctttgggag aagtatgggc ttaagccttc ccagtgggtg 540
gactaccggg ccttggccgg ggacccttcc gacaacatcc ccggcgtgaa gggcatcggg 600
gagaagacgg cggccaagct gatccgggag tggggaagcc tggaaaacct tcttaagcac 660
ctggaacagg tgaaacctgc ctccgtgcgg gagaagatcc ttagccacat ggaggacctc 720
aagctatccc tggagctttc ccgggtgcac acggagttgc cccttcaggt ggacttcgcc 780
cggcgccggg agccggaccg ggaagggctt aaggcctttt tggagaggct ggagttcgga 840
agcctcctcc acgagttcgg cctgttggaa agcccggtgg cggcggagga agctccctgg 900 ccgcccccg agggagcctt cgtggggtac gttctttccc gccccgagcc catgtgggcg 960
gagcttaacg ccttggccgc cgcctgggag ggaagggttt accgggcgga ggatcccttg 1020
gaggccttgc gggggcttgg ggaggtgagg gggcttttgg ccaaggacct ggcggtgctg 1080
gccctgaggg aagggattgc cctggcacag ggcgacgacc ccatgctcct cgcctacctc 1140
ctggatcctt ccaacaccgc ccccgaaggg gtagcccggc gctacggggg ggagtggacc 1200
gaggaggcgg gggaaagggc gctgctttcc gaaaggcttt acgccgccct cctggagcgg 1260
cttaaggggg aggagaggct tctttggctt tacgaggagg tggaaaagcc cctttcgcgg 1320
gtcctggccc acatggaggc cacgggggta tggttggatg tggcctactt gaaggccctt 1380
tccctggagg tggaggcgga gctcaggcgc ctcgaggagg aggtccaccg actggccggg 1440
catcctttca acctgaactc ccgggaccag ctggaaaggg tcctctttga cgagcttggg 1500
cttcccgcca tcggcaagac ggagaagacg ggtaagcgtt ccaccagcgc cgccgttttg 1560
gaggctttga gggaggctca tcccatagtg gaccgcatcc tccagtaccg ggagctttcc 1620
aagctcaagg gaacgtacat cgatcccttg cccgccctgg tccaccccaa gacgaaccgc 1680
ctccacaccc gtttcaacca gacggccacc gccacgggga ggcttagcag ctcggatccc 1740

```
aacctgcaaa atatccccgt gcgcacccct ttaggccagc ggatccgccg ggccttcgtg   1800

gccgaggagg ggtggaggct ggtggttttg gactacagcc agattgagct cagggtcctg   1860

gcgcaccttt ccggggacga gaacctgatc cgggtcttcc aagagggcca ggacatccac   1920

acccagacgg ccagctggat gttcggcgtg cccccagagg ccgtggattc cctgatgcgc   1980

cgggcggcca agaccatcaa cttcggcgtc ctctacggca tgtccgccca ccggctttcg   2040

ggagagctgg ccatccccta cgaggaagcg gtggccttca tcgagcggta tttccagagc   2100

taccccaagg tacgggcctg gattgagaaa accctggcgg aaggacggga gcggggctat   2160

gtggaaaccc tctttggccg ccggcgctat gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaggtgggta tcggggagga ctggctttcc gccaaggcct agtcgac                 2507
```

```
<210> SEQ ID NO 6
<211> LENGTH: 2507
<212> TYPE: DNA
<213> ORGANISM: Artificial Sequence
<220> FEATURE:
<223> OTHER INFORMATION: A derivative nucleic acid related to Thermus
      scotoductus, strain Vi7a, having GAC (encoding Asp) in place of
      GGG (encoding Gly) at positions 136-138.

<400> SEQUENCE: 6
```

```
atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgactt tgccaagagc cttttgaagg cgctaaggga agacggggat    180

gtggtgatcg tggtgtttga cgccaaggcc ccctccttcc gccaccagac ctacgaggcc    240

tacaaggcgg ggcgggctcc cacccccgag gactttcccc ggcagcttgc ccttatcaag    300

gagatggtgg accttttggg cctggagcgc ctcgaagtgc cgggttttga ggcggatgac    360

gtcctggcca ccctggccaa gaaggcggaa aaggaaggct acgaggtgcg catcctcacc    420

gcggaccggg acctttacca gcttctttcg gaccgaatct ccatccttca cccggagggt    480

tacctgatta ccccggagtg gctttgggag aagtatgggc ttaagccttc ccagtgggtg    540

gactaccggg ccttggccgg ggacccttcc gacaacatcc ccggcgtgaa gggcatcggg    600

gagaagacgg cggccaagct gatccgggag tggggaagcc tggaaaacct tcttaagcac    660

ctggaacagg tgaaacctgc ctccgtgcgg gagaagatcc ttagccacat ggaggacctc    720

aagctatccc tggagctttc ccgggtgcac acggagttgc cccttcaggt ggacttcgcc    780

cggcgccggg agccggaccg ggaagggctt aaggcctttt tggagaggct ggagttcgga    840

agcctcctcc acgagttcgg cctgttggaa agcccggtgg cggcggagga agctccctgg    900

ccgccccccg agggagcctt cgtggggtac gttctttccc gccccgagcc catgtgggcg    960

gagcttaacg ccttggccgc cgcctgggag ggaagggttt accgggcgga ggatcccttg   1020

gaggccttgc gggggcttgg ggaggtgagg gggcttttgg ccaaggacct ggcggtgctg   1080

gccctgaggg aagggattgc cctggcaccg ggcgacgacc ccatgctcct cgcctacctc   1140

ctggatcctt ccaacaccgc ccccgaaggg gtagcccggc gctacggggg ggagtggacc   1200
```

```
gaggaggcgg gggaaagggc gctgctttcc gaaaggcttt acgccgccct cctggagcgg   1260

cttaaggggg aggagaggct tctttggctt tacgaggagg tggaaaagcc cctttcgcgg   1320

gtcctggccc acatggaggc cacgggggta tggttggatg tggcctactt gaaggccctt   1380

tccctggagg tggaggcgga gctcaggcgc ctcgaggagg aggtccaccg actggccggg   1440

catcctttca acctgaactc ccgggaccag ctggaaaggg tcctctttga cgagcttggg   1500

cttcccgcca tcggcaagac ggagaagacg ggtaagcgtt ccaccagcgc cgccgttttg   1560

gaggctttga gggaggctca tcccatagtg gaccgcatcc tccagtaccg ggagctttcc   1620

aagctcaagg gaacgtacat cgatcccttg cccgccctgg tccaccccaa gacgaaccgc   1680

ctccacaccc gtttcaacca gacggccacc gccacgggga ggcttagcag ctcggatccc   1740

aacctgcaaa atatccccgt gcgcacccct ttaggccagc ggatccgccg ggccttcgtg   1800

gccgaggagg ggtggaggct ggtggttttg gactacagcc agattgagct cagggtcctg   1860

gcgcaccttt ccggggacga gaacctgatc cgggtcttcc aagagggcca ggacatccac   1920

acccagacgg ccagctggat gttcggcgtg cccccagagg ccgtggattc cctgatgcgc   1980

cgggcggcca agaccatcaa ctacggcgtc ctctacggca tgtccgccca ccggctttcg   2040

ggagagctgg ccatccccta cgaggaagcg gtggccttca tcgagcggta tttccagagc   2100

ttccccaagg tacgggcctg gattgagaaa accctggcgg aaggacggga gcggggctat   2160

gtggaaaccc tctttggccg ccggcgctat gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaggtgggta tcggggagga ctggctttcc gccaaggcct agtcgac                 2507
```

<210> SEQ ID NO 7
<211> LENGTH: 2502
<212> TYPE: DNA
<213> ORGANISM: Artificial Sequence
<220> FEATURE:
<223> OTHER INFORMATION: A derivative nucleic acid related to Thermus scotoductus, strain X-1, having TAC (encoding Tyr) in place of TTC (encoding Phe) at positions 2002-04.

<400> SEQUENCE: 7

```
atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgggtt tgccaagagc cttttgaagg cgctaaggga agacggggat    180

gtggtgatcg tggtgtttga cgccaaggcc ccctccttcc gccaccagac ctacgaggcc    240

tacaaggcgg ggcgggctcc cacccccgag gactttcccc ggcagcttgc ccttatcaag    300

gagatggtgg accttttggg cctggagcgc ctcgaggtgc cgggctttga ggcggatgac    360

gtcctggcta ccctggccaa gaaggcggaa aaggaaggct acgaggtgcg catcctcacc    420

gcggaccggg acctttacca gcttctttcg gagcgaatct ccatccttca cccggagggt    480

tacctgatca ccccggagtg gctttgggag aagtatgggc ttaagccttc ccagtgggtg    540

gactaccggg ccttggccgg ggacccttcc gacaacatcc ccggcgtgaa gggcatcggg    600

gagaagacgg cggccaagct gatccgggag tggggaagcc tggaaaacct tcttaagcac    660

ctggaacagg tgaaacctgc ctccgtgcgg gagaagatcc ttagccacat ggaggacctc    720
```

-continued

```
aagctatccc tggagctatc ccgggtgcgc acggacttgc cccttcaggt ggacttcgcc    780

cggcgccggg agccggaccg ggaggggctt aaggcctttt tggagaggct ggagttcgga    840

agcctcctcc acgagttcgg cctgttggaa agcccggtgg cggcggagga agctccctgg    900

ccgccccccg agggagcctt cgtggggtac gttctttccc gccccgagcc catgtgggcg    960

gagcttaacg ccttggccgc cgcctgggag ggaagggttt accgggcgga ggatcccttg   1020

gaggccttgc gggggcttgg ggaggtgagg gggcttttgg ccaaggacct ggcggtgctg   1080

gccctgaggg aagggattgc cctggcaccg ggcgacgacc ccatgctcct cgcctacctc   1140

ctggatcctt ccaacaccgc ccccgaaggg gtagcccggc gctacggggg ggagtggacc   1200

gaggaggcgg gggaaagggc gttgctttcc gaaaggcttt acgccgccct cctggagcgg   1260

cttaaggggg aggagaggct tctttggctt tacgaggagg tggaaaagcc cctttcgcgg   1320

gtcctggccc acatggaggc cacgggggta cggttggatg tggcctactt aaaggccctt   1380

tccctggagg tggaggcgga gctcaggcgc ctcgaggagg aggtccaccg cctggccggg   1440

catcctttca acctgaactc ccgggaccag ctggaaaggg tcctctttga cgagcttggg   1500

cttcccgcca tcggcaagac ggagaagacg ggcaagcgct ccaccagcgc cgccgttttg   1560

gaggccttgc gggaggctca tcccatcgtg gaccgcatcc ttcagtaccg ggagctttcc   1620

aagctcaagg gaacctacat cgatcccttg cctgccctgg tccaccccaa gacgaaccgc   1680

ctccacaccc gtttcaacca gacggccacc gccacgggga ggcttagcag ctcggatccc   1740

aacctgcaaa atatccccgt gcgcacccct ttgggccagc ggatccgccg ggccttcgtg   1800

gccgaggagg ggtggaggct ggtggttttg gactacagcc agattgagct cagggtcctg   1860

gcgcaccttt ccggggacga gaacctaatc cgggtcttcc aggagggcca ggacatccac   1920

acccagacgg ccagctggat gttcggcgtg cccccagagg ccgtggattc cctgatgcgt   1980

cgggcggcca agaccatcaa ctacggcgtc ctctacggca tgtccgccca ccggctttcg   2040

ggagagctgg ccatccccta cgaggaggcg gtggccttca tcgagcggta tttccagagc   2100

taccccaagg tgcgggcctg gattgagaaa accctggcgg aaggacggga acggggctat   2160

gtggaaaccc tctttggccg ccggcgctac gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaagtgggca tcggggagga ctggctttcc gccaaggcct ag                      2502
```

```
<210> SEQ ID NO 8
<211> LENGTH: 2507
<212> TYPE: DNA
<213> ORGANISM: Artificial Sequence
<220> FEATURE:
<223> OTHER INFORMATION: A derivative nucleic acid related to Thermus
      scotoductus, strain SM3, having TAC (encoding Tyr) in place of TTC
      (encoding Phe) at positions 2002-04.

<400> SEQUENCE: 8

atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgggtt tgccaagagc cttttgaagg cgctaaggga agacggggat    180
```

-continued

```
gtggtgatcg tggtgtttga cgccaaggcc ccctccttcc gccaccagac ctacgaggcc    240
tacaaggcgg ggcgggctcc cacccccgag gactttcccc ggcagcttgc ccttatcaag    300
gagatggtgg accttttggg cctggagcgc ctcgaagtgc cgggttttga ggcggatgac    360
gtcctggcca ccctggccaa gaaggcggaa aaggaaggct acgaggtgcg catcctcacc    420
gcggaccggg acctttacca gcttctttcg gaccgaatct ccatccttca cccggagggt    480
tacctgatca ccccggagtg gctttgggag aagtatgggc ttaagccttc ccagtgggtg    540
gactaccggg ccttggccgg ggacccttcc gacaacatcc ccggcgtgaa gggcatcggg    600
gagaagacgg cggccaagct gatccgggag tggggaagcc tggaaaacct tcttaagcac    660
ctggaacagg tgaaacctgc ctccgtgcgg gagaagatcc ttagccacat ggaggacctc    720
aagctatccc tggagctttc ccgggtgcac acggagttgc cccttcaggt ggacttcgcc    780
cggcgccggg agccggaccg ggaagggctt aaggcctttt tggagaggct ggagttcgga    840
agcctcctcc acgagttcgg cctgttggaa agcccggtgg cggcggagga agctccctgg    900
ccgccccccg agggagcctt cgtggggtac gttctttccc gccccgagcc catgtgggcg    960
gagcttaacg ccttggccgc cgcctgggag ggaagggttt accgggcgga ggatcccttg   1020
gaggccttgc gggggcttgg ggaggtgagg gggcttttgg ccaaggacct ggcggtgctg   1080
gccctgaggg aagggattgc cctggcacag ggcgacgacc ccatgctcct cgcctacctc   1140
ctggatcctt ccaacaccgc ccccgaaggg gtagcccggc gctacggggg ggagtggacc   1200
gaggaggcgg gggaaagggc gctgctttcc gaaaggcttt acgccgccct cctggagcgg   1260
cttaaggggg aggagaggct tctttggctt tacgaggagg tggaaaagcc cctttcgcgg   1320
gtcctggccc acatggaggc cacgggggta tggttggatg tggcctactt gaaggccctt   1380
tccctggagg tggaggcgga gctcaggcgc ctcgaggagg aggtccaccg actggccggg   1440
catcctttca acctgaactc ccgggaccag ctggaaaggg tcctctttga cgagcttggg   1500
cttcccgcca tcggcaagac ggagaagacg ggtaagcgtt ccaccagcgc cgccgttttg   1560
gaggctttga gggaggctca tcccatagtg gaccgcatcc tccagtaccg ggagctttcc   1620
aagctcaagg gaacgtacat cgatcccttg cccgccctgg tccaccccaa gacgaaccgc   1680
ctccacaccc gtttcaacca gacggccacc gccacgggga ggcttagcag ctcggatccc   1740
aacctgcaaa atatccccgt gcgcacccct ttaggccagc ggatccgccg ggccttcgtg   1800
gccgaggagg ggtggaggct ggtggttttg gactacagcc agattgagct cagggtcctg   1860
gcgcaccttt ccggggacga gaacctgatc cgggtcttcc aagagggcca ggacatccac   1920
acccagacgg ccagctggat gttcggcgtg cccccagagg ccgtggattc cctgatgcgc   1980
cgggcggcca agaccatcaa ctacggcgtc ctctacggca tgtccgccca ccggctttcg   2040
ggagagctgg ccatccccta cgaggaagcg gtggccttca tcgagcggta tttccagagc   2100
taccccaagg tacgggcctg gattgagaaa accctggcgg aaggacggga gcgggggctat   2160
gtggaaaccc tctttggccg ccggcgctat gtgcccgact tggcttcccg ggtgaagagc   2220
atccgggagg cagcggagcg catggccttc aacatgccgg tccaggggac cgccgcggat   2280
ttgatgaaac tggccatggt gaagctcttt cccaggcttc aggagctggg ggccaggatg   2340
cttttgcagg tgcacgacga actggtcctc gaggctccca aggagcaagc ggaggaagtc   2400
gcccaggagg ccaagcggac catggaggag gtgtggcccc tgaaggtgcc cttggaggtg   2460
gaggtgggta tcggggagga ctggctttcc gccaaggcct agtcgac                 2507
```

-continued

<210> SEQ ID NO 9
<211> LENGTH: 2507
<212> TYPE: DNA
<213> ORGANISM: Artificial Sequence
<220> FEATURE:
<223> OTHER INFORMATION: A derivative nucleic acid related to Thermus scotoductus, strain Vi7a, having TAC (encoding Tyr) in place of TTC (encoding Phe) at positions 2101-03.

<400> SEQUENCE: 9

```
atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgggtt tgccaagagc cttttgaagg cgctaaggga agacggggat    180

gtggtgatcg tggtgtttga cgccaaggcc ccctccttcc gccaccagac ctacgaggcc    240

tacaaggcgg ggcgggctcc caccccccgag gactttcccc ggcagcttgc ccttatcaag    300

gagatggtgg accttttggg cctggagcgc ctcgaagtgc cgggttttga ggcggatgac    360

gtcctggcca ccctggccaa gaaggcggaa aaggaaggct acgaggtgcg catcctcacc    420

gcggaccggg acctttacca gcttctttcg gaccgaatct ccatccttca cccggagggt    480

tacctgatta ccccggagtg gctttgggag aagtatgggc ttaagccttc ccagtgggtg    540

gactaccggg ccttggccgg ggacccttcc gacaacatcc ccggcgtgaa gggcatcggg    600

gagaagacgg cggccaagct gatccgggag tggggaagcc tggaaaacct tcttaagcac    660

ctggaacagg tgaaacctgc ctccgtgcgg gagaagatcc ttagccacat ggaggacctc    720

aagctatccc tggagctttc ccgggtgcac acggagttgc cccttcaggt ggacttcgcc    780

cggcgccggg agccggaccg ggaagggctt aaggcctttt tggagaggct ggagttcgga    840

agcctcctcc acgagttcgg cctgttggaa agcccggtgg cggcggagga agctccctgg    900

ccgccccccg agggagcctt cgtggggtac gttctttccc gccccgagcc catgtgggcg    960

gagcttaacg ccttggccgc cgcctgggag ggaagggttt accgggcgga ggatcccttg   1020

gaggccttgc gggggcttgg ggaggtgagg gggcttttgg ccaaggacct ggcggtgctg   1080

gccctgaggg aagggattgc cctggcaccg ggcgacgacc ccatgctcct cgcctacctc   1140

ctggatcctt ccaacaccgc ccccgaaggg gtagcccggc gctacggggg ggagtggacc   1200

gaggaggcgg gggaaagggc gctgctttcc gaaaggcttt acgccgccct cctggagcgg   1260

cttaaggggg aggagaggct tctttggctt tacgaggagg tggaaaagcc cctttcgcgg   1320

gtcctggccc acatggaggc cacgggggta tggttggatg tggcctactt gaaggccctt   1380

tccctggagg tggaggcgga gctcaggcgc ctcgaggagg aggtccaccg actggccggg   1440

catcctttca acctgaactc ccgggaccag ctggaaaggg tcctctttga cgagcttggg   1500

cttcccgcca tcggcaagac ggagaagacg ggtaagcgtt ccaccagcgc cgccgttttg   1560

gaggctttga gggaggctca tcccatagtg gaccgcatcc tccagtaccg ggagctttcc   1620

aagctcaagg gaacgtacat cgatcccttg cccgccctgg tccaccccaa gacgaaccgc   1680

ctccacaccc gtttcaacca gacggccacc gccacgggga ggcttagcag ctcggatccc   1740

aacctgcaaa atatccccgt gcgcacccct ttaggccagc ggatccgccg ggccttcgtg   1800

gccgaggagg ggtggaggct ggtggttttg gactacagcc agattgagct cagggtcctg   1860

gcgcaccttt ccggggacga gaacctgatc cgggtcttcc aagagggcca ggacatccac   1920

acccagacgg ccagctggat gttcggcgtg cccccagagg ccgtggattc cctgatgcgc   1980

cgggcggcca agaccatcaa ctacggcgtc ctctacggca tgtccgccca ccggctttcg   2040
```

-continued

```
ggagagctgg ccatccccta cgaggaagcg gtggccttca tcgagcggta tttccagagc   2100

taccccaagg tacgggcctg gattgagaaa accctggcgg aaggacggga gcggggctat   2160

gtggaaaccc tctttggccg ccggcgctat gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaggtgggta tcggggagga ctggctttcc gccaaggcct agtcgac                 2507


<210> SEQ ID NO 10
<211> LENGTH: 2502
<212> TYPE: DNA
<213> ORGANISM: Artificial Sequence
<220> FEATURE:
<223> OTHER INFORMATION: A derivative nucleic acid related to Thermus
      scotoductus, strain X-1, having GAC (encoding Asp) in place of GGG
      (encoding Gly) at positions 136-138 and having TAC (encoding Tyr)
      in place of TTC (encoding Phe) at positions 2002-04.

<400> SEQUENCE: 10

atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgactt tgccaagagc cttttgaagg cgctaaggga agacggggat    180

gtggtgatcg tggtgtttga cgccaaggcc ccctccttcc gccaccagac ctacgaggcc    240

tacaaggcgg ggcgggctcc cacccccgag gactttcccc ggcagcttgc ccttatcaag    300

gagatggtgg accttttggg cctggagcgc ctcgaggtgc cgggctttga ggcggatgac    360

gtcctggcta ccctggccaa gaaggcggaa aaggaaggct acgaggtgcg catcctcacc    420

gcggaccggg acctttacca gcttctttcg gagcgaatct ccatccttca cccggagggt    480

tacctgatca ccccggagtg gctttgggag aagtatgggc ttaagccttc ccagtgggtg    540

gactaccggg ccttggccgg ggacccttcc gacaacatcc ccggcgtgaa gggcatcggg    600

gagaagacgg cggccaagct gatccgggag tggggaagcc tggaaaacct tcttaagcac    660

ctggaacagg tgaaacctgc ctccgtgcgg gagaagatcc ttagccacat ggaggacctc    720

aagctatccc tggagctatc ccgggtgcgc acggacttgc cccttcaggt ggacttcgcc    780

cggcgccggg agccggaccg ggaggggctt aaggcctttt tggagaggct ggagttcgga    840

agcctcctcc acgagttcgg cctgttggaa agcccggtgg cggcggagga agctccctgg    900

ccgccccccg agggagcctt cgtggggtac gttctttccc gccccgagcc catgtgggcg    960

gagcttaacg ccttggccgc cgcctgggag ggaagggttt accgggcgga ggatcccttg   1020

gaggccttgc gggggcttgg ggaggtgagg gggcttttgg ccaaggacct ggcggtgctg   1080

gccctgaggg aagggattgc cctggcaccg ggcgacgacc ccatgctcct cgcctacctc   1140

ctggatcctt ccaacaccgc ccccgaaggg gtagcccggc gctacggggg ggagtggacc   1200

gaggaggcgg gggaaagggc gttgctttcc gaaaggcttt acgccgccct cctggagcgg   1260

cttaaggggg aggagaggct tctttggctt tacgaggagg tggaaaagcc cctttcgcgg   1320

gtcctggccc acatggaggc cacgggggta cggttggatg tggcctactt aaaggccctt   1380

tccctggagg tggaggcgga gctcaggcgc ctcgaggagg aggtccaccg cctggccggg   1440

catcctttca acctgaactc ccgggaccag ctggaaaggg tcctctttga cgagcttggg   1500
```

```
cttcccgcca tcggcaagac ggagaagacg ggcaagcgct ccaccagcgc cgccgttttg   1560

gaggccttgc gggaggctca tcccatcgtg gaccgcatcc ttcagtaccg ggagctttcc   1620

aagctcaagg gaacctacat cgatcccttg cctgccctgg tccaccccaa gacgaaccgc   1680

ctccacaccc gtttcaacca gacggccacc gccacgggga ggcttagcag ctcggatccc   1740

aacctgcaaa atatccccgt gcgcacccct ttgggccagc ggatccgccg ggccttcgtg   1800

gccgaggagg ggtggaggct ggtggttttg gactacagcc agattgagct caggtcctg    1860

gcgcaccttt ccggggacga gaacctaatc cgggtcttcc aggagggcca ggacatccac   1920

acccagacgg ccagctggat gttcggcgtg cccccagagg ccgtggattc cctgatgcgt   1980

cgggcggcca agaccatcaa ctacggcgtc ctctacggca tgtccgccca ccggctttcg   2040

ggagagctgg ccatccccta cgaggaggcg gtggccttca tcgagcggta tttccagagc   2100

taccccaagg tgcgggcctg gattgagaaa accctggcgg aaggacggga acggggctat   2160

gtggaaaccc tctttggccg ccggcgctac gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaagtgggca tcggggagga ctggctttcc gccaaggcct ag                      2502
```

<210> SEQ ID NO 11
<211> LENGTH: 2507
<212> TYPE: DNA
<213> ORGANISM: Artificial Sequence
<220> FEATURE:
<223> OTHER INFORMATION: A derivative nucleic acid related to Thermus scotoductus, strain SM3, having GAC (encoding Asp) place of GGG (encoding Gly) at positions 136-138 and having TAC (encoding Tyr) in place of TTC (encoding Phe) at positions 2002-04.

<400> SEQUENCE: 11

```
atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgactt tgccaagagc cttttgaagg cgctaaggga agacggggat    180

gtggtgatcg tggtgtttga cgccaaggcc ccctccttcc gccaccagac ctacgaggcc    240

tacaaggcgg ggcgggctcc cacccccgag gactttcccc ggcagcttgc ccttatcaag    300

gagatggtgg accttttggg cctggagcgc ctcgaagtgc cgggttttga ggcggatgac    360

gtcctggcca ccctggccaa gaaggcggaa aaggaaggct acgaggtgcg catcctcacc    420

gcggaccggg acctttacca gcttctttcg gaccgaatct ccatccttca cccggagggt    480

tacctgatca ccccggagtg gctttgggag aagtatgggc ttaagccttc ccagtgggtg    540

gactaccggg ccttggccgg ggacccttcc gacaacatcc ccggcgtgaa gggcatcggg    600

gagaagacgg cggccaagct gatccgggag tggggaagcc tggaaaacct tcttaagcac    660

ctggaacagg tgaaacctgc ctccgtgcgg gagaagatcc ttagccacat ggaggacctc    720

aagctatccc tggagctttc ccgggtgcac acggagttgc cccttcaggt ggacttcgcc    780

cggcgccggg agccggaccg ggaagggctt aaggcctttt tggagaggct ggagttcgga    840

agcctcctcc acgagttcgg cctgttggaa agcccggtgg cggcggagga agctccctgg    900

ccgccccccg agggagcctt cgtggggtac gttctttccc gccccgagcc catgtgggcg    960
```

-continued

```
gagcttaacg ccttggccgc cgcctgggag ggaagggttt accgggcgga ggatcccttg   1020

gaggccttgc gggggcttgg ggaggtgagg gggcttttgg ccaaggacct ggcggtgctg   1080

gccctgaggg aagggattgc cctggcacag ggcgacgacc ccatgctcct cgcctacctc   1140

ctggatcctt ccaacaccgc ccccgaaggg gtagcccggc gctacggggg ggagtggacc   1200

gaggaggcgg gggaaagggc gctgctttcc gaaaggcttt acgccgccct cctggagcgg   1260

cttaaggggg aggagaggct tctttggctt tacgaggagg tggaaaagcc cctttcgcgg   1320

gtcctggccc acatggaggc cacgggggta tggttggatg tggcctactt gaaggccctt   1380

tccctggagg tggaggcgga gctcaggcgc ctcgaggagg aggtccaccg actggccggg   1440

catcctttca acctgaactc ccgggaccag ctggaaaggg tcctctttga cgagcttggg   1500

cttcccgcca tcggcaagac ggagaagacg ggtaagcgtt ccaccagcgc cgccgttttg   1560

gaggctttga gggaggctca tcccatagtg gaccgcatcc tccagtaccg ggagctttcc   1620

aagctcaagg gaacgtacat cgatcccttg cccgccctgg tccaccccaa gacgaaccgc   1680

ctccacaccc gtttcaacca gacggccacc gccacgggga ggcttagcag ctcggatccc   1740

aacctgcaaa atatccccgt gcgcacccct ttaggccagc ggatccgccg ggccttcgtg   1800

gccgaggagg ggtggaggct ggtggttttg gactacagcc agattgagct caggggtcctg   1860

gcgcaccttt ccggggacga gaacctgatc cgggtcttcc aagagggcca ggacatccac   1920

acccagacgg ccagctggat gttcggcgtg cccccagagg ccgtggattc cctgatgcgc   1980

cgggcggcca agaccatcaa ctacggcgtc ctctacggca tgtccgccca ccggctttcg   2040

ggagagctgg ccatccccta cgaggaagcg gtggccttca tcgagcggta tttccagagc   2100

taccccaagg tacgggcctg gattgagaaa accctggcgg aaggacggga gcggggctat   2160

gtggaaaccc tctttggccg ccggcgctat gtgcccgact tggcttcccg ggtgaagagc   2220

atccgggagg cagcggagcg catggccttc aacatgccgg tccaggggac cgccgcggat   2280

ttgatgaaac tggccatggt gaagctcttt cccaggcttc aggagctggg ggccaggatg   2340

cttttgcagg tgcacgacga actggtcctc gaggctccca aggagcaagc ggaggaagtc   2400

gcccaggagg ccaagcggac catggaggag gtgtggcccc tgaaggtgcc cttggaggtg   2460

gaggtgggta tcggggagga ctggctttcc gccaaggcct agtcgac                2507
```

<210> SEQ ID NO 12
<211> LENGTH: 2507
<212> TYPE: DNA
<213> ORGANISM: Artificial Sequence
<220> FEATURE:
<223> OTHER INFORMATION: A derivative nucleic acid related to Thermus scotoductus, strain Vi7a, having GAC (encoding Asp) in place of GGG (encoding Gly) at positions 136-138 and having TAC (encoding Tyr) in place of TTC (encoding Phe) at positions 2101-03.

<400> SEQUENCE: 12

```
atgagggcga tgctgcccct ctttgagccc aagggccggg tgcttctggt ggacggccac     60

cacctggcct accgtacctt ttttgccctg aagggcctca ccaccagccg cggggagccg    120

gtccaggcgg tgtacgactt tgccaagagc cttttgaagg cgctaaggga agacggggat    180

gtggtgatcg tggtgtttga cgccaaggcc ccctccttcc gccaccagac ctacgaggcc    240

tacaaggcgg ggcgggctcc cacccccgag gactttcccc ggcagcttgc ccttatcaag    300

gagatggtgg accttttggg cctggagcgc ctcgaagtgc cgggttttga ggcggatgac    360

gtcctggcca ccctggccaa gaaggcggaa aaggaaggct acgaggtgcg catcctcacc    420
```

```
gcggaccggg acctttacca gcttctttcg gaccgaatct ccatccttca cccggagggt    480
tacctgatta ccccggagtg gctttgggag aagtatgggc ttaagccttc ccagtgggtg    540
gactaccggg ccttggccgg ggacccttcc gacaacatcc ccggcgtgaa gggcatcggg    600
gagaagacgg cggccaagct gatccgggag tggggaagcc tggaaaacct tcttaagcac    660
ctggaacagg tgaaacctgc ctccgtgcgg gagaagatcc ttagccacat ggaggacctc    720
aagctatccc tggagctttc ccgggtgcac acggagttgc cccttcaggt ggacttcgcc    780
cggcgccggg agccggaccg ggaagggctt aaggcctttt tggagaggct ggagttcgga    840
agcctcctcc acgagttcgg cctgttggaa agcccggtgg cggcggagga agctccctgg    900
ccgccccccg agggagcctt cgtggggtac gttctttccc gccccgagcc catgtgggcg    960
gagcttaacg ccttggccgc cgcctgggag ggaagggttt accgggcgga ggatcccttg   1020
gaggccttgc gggggcttgg ggaggtgagg gggcttttgg ccaaggacct ggcggtgctg   1080
gccctgaggg aagggattgc cctggcaccg ggcgacgacc ccatgctcct cgcctacctc   1140
ctggatcctt ccaacaccgc ccccgaaggg gtagcccggc gctacggggg ggagtggacc   1200
gaggaggcgg gggaaagggc gctgctttcc gaaaggcttt acgccgccct cctggagcgg   1260
cttaaggggg aggagaggct tctttggctt tacgaggagg tggaaaagcc cctttcgcgg   1320
gtcctggccc acatggaggc cacgggggta tggttggatg tggcctactt gaaggccctt   1380
tccctggagg tggaggcgga gctcaggcgc ctcgaggagg aggtccaccg actggccggg   1440
catcctttca acctgaactc ccgggaccag ctggaaaggg tcctctttga cgagcttggg   1500
cttcccgcca tcggcaagac ggagaagacg ggtaagcgtt ccaccagcgc cgccgttttg   1560
gaggctttga gggaggctca tcccatagtg gaccgcatcc tccagtaccg ggagctttcc   1620
aagctcaagg gaacgtacat cgatcccttg cccgccctgg tccaccccaa gacgaaccgc   1680
ctccacaccc gtttcaacca gacggccacc gccacgggga ggcttagcag ctcggatccc   1740
aacctgcaaa atatccccgt gcgcacccct ttaggccagc ggatccgccg ggccttcgtg   1800
gccgaggagg ggtggaggct ggtggttttg gactacagcc agattgagct caggtcctg    1860
gcgcaccttt ccggggacga gaacctgatc cgggtcttcc aagagggcca ggacatccac   1920
acccagacgg ccagctggat gttcggcgtg cccccagagg ccgtggattc cctgatgcgc   1980
cgggcggcca agaccatcaa ctacggcgtc ctctacggca tgtccgccca ccggctttcg   2040
ggagagctgg ccatccccta cgaggaagcg gtggccttca tcgagcggta tttccagagc   2100
taccccaagg tacgggcctg gattgagaaa accctggcgg aaggacggga gcggggctat   2160
gtggaaaccc tctttggccg ccggcgctat gtgcccgact tggcttcccg ggtgaagagc   2220
atccgggagg cagcggagcg catggccttc aacatgccgg tccaggggac cgccgcggat   2280
ttgatgaaac tggccatggt gaagctcttt cccaggcttc aggagctggg ggccaggatg   2340
cttttgcagg tgcacgacga actggtcctc gaggctccca aggagcaagc ggaggaagtc   2400
gcccaggagg ccaagcggac catggaggag gtgtggcccc tgaaggtgcc cttggaggtg   2460
gaggtgggta tcggggagga ctggctttcc gccaaggcct agtcgac                 2507
```

<210> SEQ ID NO 13
<211> LENGTH: 833
<212> TYPE: PRT
<213> ORGANISM: Artificial Sequence
<220> FEATURE:
<223> OTHER INFORMATION: A wild type Thermus scotoductus nucleic acid polymerase polypeptide from strain X-1 with three additional amino acids at the N-terminus.

<400> SEQUENCE: 13

Met Arg Ala Met Leu Pro Leu Phe Glu Pro Lys Gly Arg Val Leu Leu
1 5 10 15

Val Asp Gly His His Leu Ala Tyr Arg Thr Phe Phe Ala Leu Lys Gly
20 25 30

Leu Thr Thr Ser Arg Gly Glu Pro Val Gln Ala Val Tyr Gly Phe Ala
35 40 45

Lys Ser Leu Leu Lys Ala Leu Arg Glu Asp Gly Asp Val Val Ile Val
50 55 60

Val Phe Asp Ala Lys Ala Pro Ser Phe Arg His Gln Thr Tyr Glu Ala
65 70 75 80

Tyr Lys Ala Gly Arg Ala Pro Thr Pro Glu Asp Phe Pro Arg Gln Leu
85 90 95

Ala Leu Ile Lys Glu Met Val Asp Leu Leu Gly Leu Glu Arg Leu Glu
100 105 110

Val Pro Gly Phe Glu Ala Asp Asp Val Leu Ala Thr Leu Ala Lys Lys
115 120 125

Ala Glu Lys Glu Gly Tyr Glu Val Arg Ile Leu Thr Ala Asp Arg Asp
130 135 140

Leu Tyr Gln Leu Leu Ser Glu Arg Ile Ser Ile Leu His Pro Glu Gly
145 150 155 160

Tyr Leu Ile Thr Pro Glu Trp Leu Trp Glu Lys Tyr Gly Leu Lys Pro
165 170 175

Ser Gln Trp Val Asp Tyr Arg Ala Leu Ala Gly Asp Pro Ser Asp Asn
180 185 190

Ile Pro Gly Val Lys Gly Ile Gly Glu Lys Thr Ala Ala Lys Leu Ile
195 200 205

Arg Glu Trp Gly Ser Leu Glu Asn Leu Leu Lys His Leu Glu Gln Val
210 215 220

Lys Pro Ala Ser Val Arg Glu Lys Ile Leu Ser His Met Glu Asp Leu
225 230 235 240

Lys Leu Ser Leu Glu Leu Ser Arg Val Arg Thr Asp Leu Pro Leu Gln
245 250 255

Val Asp Phe Ala Arg Arg Arg Glu Pro Asp Arg Glu Gly Leu Lys Ala
260 265 270

Phe Leu Glu Arg Leu Glu Phe Gly Ser Leu Leu His Glu Phe Gly Leu
275 280 285

Leu Glu Ser Pro Val Ala Ala Glu Glu Ala Pro Trp Pro Pro Pro Glu
290 295 300

Gly Ala Phe Val Gly Tyr Val Leu Ser Arg Pro Glu Pro Met Trp Ala
305 310 315 320

Glu Leu Asn Ala Leu Ala Ala Ala Trp Glu Gly Arg Val Tyr Arg Ala
325 330 335

Glu Asp Pro Leu Glu Ala Leu Arg Gly Leu Gly Glu Val Arg Gly Leu
340 345 350

Leu Ala Lys Asp Leu Ala Val Leu Ala Leu Arg Glu Gly Ile Ala Leu
355 360 365

Ala Pro Gly Asp Asp Pro Met Leu Leu Ala Tyr Leu Leu Asp Pro Ser
370 375 380

Asn Thr Ala Pro Glu Gly Val Ala Arg Arg Tyr Gly Gly Glu Trp Thr
385 390 395 400

Glu Glu Ala Gly Glu Arg Ala Leu Leu Ser Glu Arg Leu Tyr Ala Ala

-continued

```
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Arg Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830
```

-continued

Ala

<210> SEQ ID NO 14
<211> LENGTH: 830
<212> TYPE: PRT
<213> ORGANISM: Thermus scotoductus

<400> SEQUENCE: 14

Met Leu Pro Leu Phe Glu Pro Lys Gly Arg Val Leu Leu Val Asp Gly
1 5 10 15

His His Leu Ala Tyr Arg Thr Phe Phe Ala Leu Lys Gly Leu Thr Thr
20 25 30

Ser Arg Gly Glu Pro Val Gln Ala Val Tyr Gly Phe Ala Lys Ser Leu
35 40 45

Leu Lys Ala Leu Arg Glu Asp Gly Asp Val Val Ile Val Val Phe Asp
50 55 60

Ala Lys Ala Pro Ser Phe Arg His Gln Thr Tyr Glu Ala Tyr Lys Ala
65 70 75 80

Gly Arg Ala Pro Thr Pro Glu Asp Phe Pro Arg Gln Leu Ala Leu Ile
85 90 95

Lys Glu Met Val Asp Leu Leu Gly Leu Glu Arg Leu Glu Val Pro Gly
100 105 110

Phe Glu Ala Asp Asp Val Leu Ala Thr Leu Ala Lys Lys Ala Glu Lys
115 120 125

Glu Gly Tyr Glu Val Arg Ile Leu Thr Ala Asp Arg Asp Leu Tyr Gln
130 135 140

Leu Leu Ser Glu Arg Ile Ser Ile Leu His Pro Glu Gly Tyr Leu Ile
145 150 155 160

Thr Pro Glu Trp Leu Trp Glu Lys Tyr Gly Leu Lys Pro Ser Gln Trp
165 170 175

Val Asp Tyr Arg Ala Leu Ala Gly Asp Pro Ser Asp Asn Ile Pro Gly
180 185 190

Val Lys Gly Ile Gly Glu Lys Thr Ala Ala Lys Leu Ile Arg Glu Trp
195 200 205

Gly Ser Leu Glu Asn Leu Leu Lys His Leu Glu Gln Val Lys Pro Ala
210 215 220

Ser Val Arg Glu Lys Ile Leu Ser His Met Glu Asp Leu Lys Leu Ser
225 230 235 240

Leu Glu Leu Ser Arg Val Arg Thr Asp Leu Pro Leu Gln Val Asp Phe
245 250 255

Ala Arg Arg Arg Glu Pro Asp Arg Glu Gly Leu Lys Ala Phe Leu Glu
260 265 270

Arg Leu Glu Phe Gly Ser Leu Leu His Glu Phe Gly Leu Leu Glu Ser
275 280 285

Pro Val Ala Ala Glu Glu Ala Pro Trp Pro Pro Pro Glu Gly Ala Phe
290 295 300

Val Gly Tyr Val Leu Ser Arg Pro Glu Pro Met Trp Ala Glu Leu Asn
305 310 315 320

Ala Leu Ala Ala Ala Trp Glu Gly Arg Val Tyr Arg Ala Glu Asp Pro
325 330 335

Leu Glu Ala Leu Arg Gly Leu Gly Glu Val Arg Gly Leu Leu Ala Lys
340 345 350

Asp Leu Ala Val Leu Ala Leu Arg Glu Gly Ile Ala Leu Ala Pro Gly
355 360 365

-continued

```
Asp Asp Pro Met Leu Leu Ala Tyr Leu Leu Asp Pro Ser Asn Thr Ala
    370                 375                 380

Pro Glu Gly Val Ala Arg Arg Tyr Gly Gly Glu Trp Thr Glu Glu Ala
385                 390                 395                 400

Gly Glu Arg Ala Leu Leu Ser Glu Arg Leu Tyr Ala Ala Leu Leu Glu
                405                 410                 415

Arg Leu Lys Gly Glu Glu Arg Leu Leu Trp Leu Tyr Glu Glu Val Glu
            420                 425                 430

Lys Pro Leu Ser Arg Val Leu Ala His Met Glu Ala Thr Gly Val Arg
        435                 440                 445

Leu Asp Val Ala Tyr Leu Lys Ala Leu Ser Leu Glu Val Glu Ala Glu
    450                 455                 460

Leu Arg Arg Leu Glu Glu Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Ala Ile Gly Lys Thr Glu Lys Thr Gly Lys Arg Ser Thr
            500                 505                 510

Ser Ala Ala Val Leu Glu Ala Leu Arg Glu Ala His Pro Ile Val Asp
        515                 520                 525

Arg Ile Leu Gln Tyr Arg Glu Leu Ser Lys Leu Lys Gly Thr Tyr Ile
    530                 535                 540

Asp Pro Leu Pro Ala Leu Val His Pro Lys Thr Asn Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Arg Ala Phe Val Ala Glu Glu Gly Trp Arg Leu Val Val Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Gln Glu Gly Gln Asp Ile His Thr Gln Thr
625                 630                 635                 640

Ala Ser Trp Met Phe Gly Val Pro Pro Glu Ala Val Asp Ser Leu Met
                645                 650                 655

Arg Arg Ala Ala Lys Thr Ile Asn Phe Gly Val Leu Tyr Gly Met Ser
            660                 665                 670

Ala His Arg Leu Ser Gly Glu Leu Ala Ile Pro Tyr Glu Glu Ala Val
        675                 680                 685

Ala Phe Ile Glu Arg Tyr Phe Gln Ser Tyr Pro Lys Val Arg Ala Trp
    690                 695                 700

Ile Glu Lys Thr Leu Ala Glu Gly Arg Glu Arg Gly Tyr Val Glu Thr
705                 710                 715                 720

Leu Phe Gly Arg Arg Arg Tyr Val Pro Asp Leu Ala Ser Arg Val Lys
                725                 730                 735

Ser Ile Arg Glu Ala Ala Glu Arg Met Ala Phe Asn Met Pro Val Gln
            740                 745                 750

Gly Thr Ala Ala Asp Leu Met Lys Leu Ala Met Val Lys Leu Phe Pro
        755                 760                 765

Arg Leu Gln Glu Leu Gly Ala Arg Met Leu Leu Gln Val His Asp Glu
    770                 775                 780
```

-continued

```
Leu Val Leu Glu Ala Pro Lys Glu Gln Ala Glu Glu Val Ala Gln Glu
785                 790                 795                 800

Ala Lys Arg Thr Met Glu Glu Val Trp Pro Leu Lys Val Pro Leu Glu
                805                 810                 815

Val Glu Val Gly Ile Gly Glu Asp Trp Leu Ser Ala Lys Ala
            820                 825                 830


<210> SEQ ID NO 15
<211> LENGTH: 833
<212> TYPE: PRT
<213> ORGANISM: Thermus scotoductus

<400> SEQUENCE: 15

Met Arg Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335
```

-continued

```
Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Gln Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750
```

-continued

```
Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830

Ala


<210> SEQ ID NO 16
<211> LENGTH: 833
<212> TYPE: PRT
<213> ORGANISM: Thermus scotoductus

<400> SEQUENCE: 16

Met Arg Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285
```

```
Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
```

-continued 705 710 715 720

Val Glu Thr Leu Phe Gly Arg Arg Arg Tyr Val Pro Asp Leu Ala Ser
725 730 735

Arg Val Lys Ser Ile Arg Glu Ala Ala Glu Arg Met Ala Phe Asn Met
740 745 750

Pro Val Gln Gly Thr Ala Ala Asp Leu Met Lys Leu Ala Met Val Lys
755 760 765

Leu Phe Pro Arg Leu Gln Glu Leu Gly Ala Arg Met Leu Leu Gln Val
770 775 780

His Asp Glu Leu Val Leu Glu Ala Pro Lys Glu Gln Ala Glu Glu Val
785 790 795 800

Ala Gln Glu Ala Lys Arg Thr Met Glu Glu Val Trp Pro Leu Lys Val
805 810 815

Pro Leu Glu Val Glu Val Gly Ile Gly Glu Asp Trp Leu Ser Ala Lys
820 825 830

Ala

<210> SEQ ID NO 17
<211> LENGTH: 833
<212> TYPE: PRT
<213> ORGANISM: Artificial Sequence
<220> FEATURE:
<223> OTHER INFORMATION: A Thermus scotoductus nucleic acid polymerase polypeptide from strain X-1 in which Asp is used in place of Gly at position 46.

<400> SEQUENCE: 17

Met Arg Ala Met Leu Pro Leu Phe Glu Pro Lys Gly Arg Val Leu Leu
1 5 10 15

Val Asp Gly His His Leu Ala Tyr Arg Thr Phe Phe Ala Leu Lys Gly
20 25 30

Leu Thr Thr Ser Arg Gly Glu Pro Val Gln Ala Val Tyr Asp Phe Ala
35 40 45

Lys Ser Leu Leu Lys Ala Leu Arg Glu Asp Gly Asp Val Val Ile Val
50 55 60

Val Phe Asp Ala Lys Ala Pro Ser Phe Arg His Gln Thr Tyr Glu Ala
65 70 75 80

Tyr Lys Ala Gly Arg Ala Pro Thr Pro Glu Asp Phe Pro Arg Gln Leu
85 90 95

Ala Leu Ile Lys Glu Met Val Asp Leu Leu Gly Leu Glu Arg Leu Glu
100 105 110

Val Pro Gly Phe Glu Ala Asp Asp Val Leu Ala Thr Leu Ala Lys Lys
115 120 125

Ala Glu Lys Glu Gly Tyr Glu Val Arg Ile Leu Thr Ala Asp Arg Asp
130 135 140

Leu Tyr Gln Leu Leu Ser Glu Arg Ile Ser Ile Leu His Pro Glu Gly
145 150 155 160

Tyr Leu Ile Thr Pro Glu Trp Leu Trp Glu Lys Tyr Gly Leu Lys Pro
165 170 175

Ser Gln Trp Val Asp Tyr Arg Ala Leu Ala Gly Asp Pro Ser Asp Asn
180 185 190

Ile Pro Gly Val Lys Gly Ile Gly Glu Lys Thr Ala Ala Lys Leu Ile
195 200 205

Arg Glu Trp Gly Ser Leu Glu Asn Leu Leu Lys His Leu Glu Gln Val
210 215 220

-continued

```
Lys Pro Ala Ser Val Arg Glu Lys Ile Leu Ser His Met Glu Asp Leu
225                 230                 235                 240

Lys Leu Ser Leu Glu Leu Ser Arg Val Arg Thr Asp Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Arg Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
```

```
                645                 650                 655

Ser Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830

Ala


<210> SEQ ID NO 18
<211> LENGTH: 830
<212> TYPE: PRT
<213> ORGANISM: Artificial Sequence
<220> FEATURE:
<223> OTHER INFORMATION: A Thermus scotoductus nucleic acid polymerase
      polypeptide from strain X-1 in which Asp is used in place of Gly
      at position 46.

<400> SEQUENCE: 18

Met Leu Pro Leu Phe Glu Pro Lys Gly Arg Val Leu Leu Val Asp Gly
 1               5                  10                  15

His His Leu Ala Tyr Arg Thr Phe Phe Ala Leu Lys Gly Leu Thr Thr
            20                  25                  30

Ser Arg Gly Glu Pro Val Gln Ala Val Tyr Asp Phe Ala Lys Ser Leu
        35                  40                  45

Leu Lys Ala Leu Arg Glu Asp Gly Asp Val Val Ile Val Val Phe Asp
    50                  55                  60

Ala Lys Ala Pro Ser Phe Arg His Gln Thr Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Met Val Asp Leu Leu Gly Leu Glu Arg Leu Glu Val Pro Gly
            100                 105                 110

Phe Glu Ala Asp Asp Val Leu Ala Thr Leu Ala Lys Lys Ala Glu Lys
        115                 120                 125

Glu Gly Tyr Glu Val Arg Ile Leu Thr Ala Asp Arg Asp Leu Tyr Gln
    130                 135                 140

Leu Leu Ser Glu Arg Ile Ser Ile Leu His Pro Glu Gly Tyr Leu Ile
145                 150                 155                 160
```

-continued

```
Thr Pro Glu Trp Leu Trp Glu Lys Tyr Gly Leu Lys Pro Ser Gln Trp
                165                 170                 175

Val Asp Tyr Arg Ala Leu Ala Gly Asp Pro Ser Asp Asn Ile Pro Gly
            180                 185                 190

Val Lys Gly Ile Gly Glu Lys Thr Ala Ala Lys Leu Ile Arg Glu Trp
        195                 200                 205

Gly Ser Leu Glu Asn Leu Leu Lys His Leu Glu Gln Val Lys Pro Ala
    210                 215                 220

Ser Val Arg Glu Lys Ile Leu Ser His Met Glu Asp Leu Lys Leu Ser
225                 230                 235                 240

Leu Glu Leu Ser Arg Val Arg Thr Asp Leu Pro Leu Gln Val Asp Phe
                245                 250                 255

Ala Arg Arg Arg Glu Pro Asp Arg Glu Gly Leu Lys Ala Phe Leu Glu
            260                 265                 270

Arg Leu Glu Phe Gly Ser Leu Leu His Glu Phe Gly Leu Leu Glu Ser
        275                 280                 285

Pro Val Ala Ala Glu Glu Ala Pro Trp Pro Pro Pro Glu Gly Ala Phe
    290                 295                 300

Val Gly Tyr Val Leu Ser Arg Pro Glu Pro Met Trp Ala Glu Leu Asn
305                 310                 315                 320

Ala Leu Ala Ala Ala Trp Glu Gly Arg Val Tyr Arg Ala Glu Asp Pro
                325                 330                 335

Leu Glu Ala Leu Arg Gly Leu Gly Glu Val Arg Gly Leu Leu Ala Lys
            340                 345                 350

Asp Leu Ala Val Leu Ala Leu Arg Glu Gly Ile Ala Leu Ala Pro Gly
        355                 360                 365

Asp Asp Pro Met Leu Leu Ala Tyr Leu Leu Asp Pro Ser Asn Thr Ala
    370                 375                 380

Pro Glu Gly Val Ala Arg Arg Tyr Gly Gly Glu Trp Thr Glu Glu Ala
385                 390                 395                 400

Gly Glu Arg Ala Leu Leu Ser Glu Arg Leu Tyr Ala Ala Leu Leu Glu
                405                 410                 415

Arg Leu Lys Gly Glu Glu Arg Leu Leu Trp Leu Tyr Glu Glu Val Glu
            420                 425                 430

Lys Pro Leu Ser Arg Val Leu Ala His Met Glu Ala Thr Gly Val Arg
        435                 440                 445

Leu Asp Val Ala Tyr Leu Lys Ala Leu Ser Leu Glu Val Glu Ala Glu
    450                 455                 460

Leu Arg Arg Leu Glu Glu Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Ala Ile Gly Lys Thr Glu Lys Thr Gly Lys Arg Ser Thr
            500                 505                 510

Ser Ala Ala Val Leu Glu Ala Leu Arg Glu Ala His Pro Ile Val Asp
        515                 520                 525

Arg Ile Leu Gln Tyr Arg Glu Leu Ser Lys Leu Lys Gly Thr Tyr Ile
    530                 535                 540

Asp Pro Leu Pro Ala Leu Val His Pro Lys Thr Asn Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
```

```
            580                 585                 590

Arg Arg Ala Phe Val Ala Glu Glu Gly Trp Arg Leu Val Val Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Gln Glu Gly Gln Asp Ile His Thr Gln Thr
625                 630                 635                 640

Ala Ser Trp Met Phe Gly Val Pro Pro Glu Ala Val Asp Ser Leu Met
                645                 650                 655

Arg Arg Ala Ala Lys Thr Ile Asn Phe Gly Val Leu Tyr Gly Met Ser
            660                 665                 670

Ala His Arg Leu Ser Gly Glu Leu Ala Ile Pro Tyr Glu Glu Ala Val
        675                 680                 685

Ala Phe Ile Glu Arg Tyr Phe Gln Ser Tyr Pro Lys Val Arg Ala Trp
    690                 695                 700

Ile Glu Lys Thr Leu Ala Glu Gly Arg Glu Arg Gly Tyr Val Glu Thr
705                 710                 715                 720

Leu Phe Gly Arg Arg Arg Tyr Val Pro Asp Leu Ala Ser Arg Val Lys
                725                 730                 735

Ser Ile Arg Glu Ala Ala Glu Arg Met Ala Phe Asn Met Pro Val Gln
            740                 745                 750

Gly Thr Ala Ala Asp Leu Met Lys Leu Ala Met Val Lys Leu Phe Pro
        755                 760                 765

Arg Leu Gln Glu Leu Gly Ala Arg Met Leu Leu Gln Val His Asp Glu
    770                 775                 780

Leu Val Leu Glu Ala Pro Lys Glu Gln Ala Glu Glu Val Ala Gln Glu
785                 790                 795                 800

Ala Lys Arg Thr Met Glu Glu Val Trp Pro Leu Lys Val Pro Leu Glu
                805                 810                 815

Val Glu Val Gly Ile Gly Glu Asp Trp Leu Ser Ala Lys Ala
            820                 825                 830


<210> SEQ ID NO 19
<211> LENGTH: 833
<212> TYPE: PRT
<213> ORGANISM: Artificial Sequence
<220> FEATURE:
<223> OTHER INFORMATION: A Thermus scotoductus nucleic acid polymerase
      polypeptide from strain SM3 in which Asp is used in place of Gly
      at position 46.

<400> SEQUENCE: 19

Met Arg Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110
```

```
Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Gln Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525
```

```
Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830

Ala


<210> SEQ ID NO 20
<211> LENGTH: 833
<212> TYPE: PRT
<213> ORGANISM: Artificial Sequence
<220> FEATURE:
<223> OTHER INFORMATION: A Thermus scotoductus nucleic acid polymerase
      polypeptide from strain Vi7a in which Asp is used in place of Gly
      at position 46.

<400> SEQUENCE: 20

Met Arg Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45
```

-continued

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460

```
Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830

Ala


<210> SEQ ID NO 21
<211> LENGTH: 833
<212> TYPE: PRT
<213> ORGANISM: Artificial Sequence
<220> FEATURE:
<223> OTHER INFORMATION: A derivative Thermus scotoductus polypeptide
      from strain X-1 in which Tyr is used in place of Phe at position
```

668.

<400> SEQUENCE: 21

```
Met Arg Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Glu Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val Arg Thr Asp Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400
```

-continued

```
Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Arg Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Tyr Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
```

820 825 830

Ala

<210> SEQ ID NO 22
<211> LENGTH: 830
<212> TYPE: PRT
<213> ORGANISM: Artificial Sequence
<220> FEATURE:
<223> OTHER INFORMATION: A derivative Thermus scotoductus polypeptide from strain X-1 in which Tyr is used in place of Phe at position 668.

<400> SEQUENCE: 22

Met Leu Pro Leu Phe Glu Pro Lys Gly Arg Val Leu Leu Val Asp Gly
1 5 10 15

His His Leu Ala Tyr Arg Thr Phe Phe Ala Leu Lys Gly Leu Thr Thr
20 25 30

Ser Arg Gly Glu Pro Val Gln Ala Val Tyr Gly Phe Ala Lys Ser Leu
35 40 45

Leu Lys Ala Leu Arg Glu Asp Gly Asp Val Val Ile Val Val Phe Asp
50 55 60

Ala Lys Ala Pro Ser Phe Arg His Gln Thr Tyr Glu Ala Tyr Lys Ala
65 70 75 80

Gly Arg Ala Pro Thr Pro Glu Asp Phe Pro Arg Gln Leu Ala Leu Ile
85 90 95

Lys Glu Met Val Asp Leu Leu Gly Leu Glu Arg Leu Glu Val Pro Gly
100 105 110

Phe Glu Ala Asp Asp Val Leu Ala Thr Leu Ala Lys Lys Ala Glu Lys
115 120 125

Glu Gly Tyr Glu Val Arg Ile Leu Thr Ala Asp Arg Asp Leu Tyr Gln
130 135 140

Leu Leu Ser Glu Arg Ile Ser Ile Leu His Pro Glu Gly Tyr Leu Ile
145 150 155 160

Thr Pro Glu Trp Leu Trp Glu Lys Tyr Gly Leu Lys Pro Ser Gln Trp
165 170 175

Val Asp Tyr Arg Ala Leu Ala Gly Asp Pro Ser Asp Asn Ile Pro Gly
180 185 190

Val Lys Gly Ile Gly Glu Lys Thr Ala Ala Lys Leu Ile Arg Glu Trp
195 200 205

Gly Ser Leu Glu Asn Leu Leu Lys His Leu Glu Gln Val Lys Pro Ala
210 215 220

Ser Val Arg Glu Lys Ile Leu Ser His Met Glu Asp Leu Lys Leu Ser
225 230 235 240

Leu Glu Leu Ser Arg Val Arg Thr Asp Leu Pro Leu Gln Val Asp Phe
245 250 255

Ala Arg Arg Arg Glu Pro Asp Arg Glu Gly Leu Lys Ala Phe Leu Glu
260 265 270

Arg Leu Glu Phe Gly Ser Leu Leu His Glu Phe Gly Leu Leu Glu Ser
275 280 285

Pro Val Ala Ala Glu Glu Ala Pro Trp Pro Pro Pro Glu Gly Ala Phe
290 295 300

Val Gly Tyr Val Leu Ser Arg Pro Glu Pro Met Trp Ala Glu Leu Asn
305 310 315 320

Ala Leu Ala Ala Ala Trp Glu Gly Arg Val Tyr Arg Ala Glu Asp Pro
325 330 335

-continued

```
Leu Glu Ala Leu Arg Gly Leu Gly Glu Val Arg Gly Leu Leu Ala Lys
            340                 345                 350

Asp Leu Ala Val Leu Ala Leu Arg Glu Gly Ile Ala Leu Ala Pro Gly
        355                 360                 365

Asp Asp Pro Met Leu Leu Ala Tyr Leu Leu Asp Pro Ser Asn Thr Ala
    370                 375                 380

Pro Glu Gly Val Ala Arg Arg Tyr Gly Gly Glu Trp Thr Glu Glu Ala
385                 390                 395                 400

Gly Glu Arg Ala Leu Leu Ser Glu Arg Leu Tyr Ala Ala Leu Leu Glu
                405                 410                 415

Arg Leu Lys Gly Glu Glu Arg Leu Leu Trp Leu Tyr Glu Glu Val Glu
            420                 425                 430

Lys Pro Leu Ser Arg Val Leu Ala His Met Glu Ala Thr Gly Val Arg
        435                 440                 445

Leu Asp Val Ala Tyr Leu Lys Ala Leu Ser Leu Glu Val Glu Ala Glu
    450                 455                 460

Leu Arg Arg Leu Glu Glu Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Ala Ile Gly Lys Thr Glu Lys Thr Gly Lys Arg Ser Thr
            500                 505                 510

Ser Ala Ala Val Leu Glu Ala Leu Arg Glu Ala His Pro Ile Val Asp
        515                 520                 525

Arg Ile Leu Gln Tyr Arg Glu Leu Ser Lys Leu Lys Gly Thr Tyr Ile
    530                 535                 540

Asp Pro Leu Pro Ala Leu Val His Pro Lys Thr Asn Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Arg Ala Phe Val Ala Glu Glu Gly Trp Arg Leu Val Val Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Gln Glu Gly Gln Asp Ile His Thr Gln Thr
625                 630                 635                 640

Ala Ser Trp Met Phe Gly Val Pro Pro Glu Ala Val Asp Ser Leu Met
                645                 650                 655

Arg Arg Ala Ala Lys Thr Ile Asn Tyr Gly Val Leu Tyr Gly Met Ser
            660                 665                 670

Ala His Arg Leu Ser Gly Glu Leu Ala Ile Pro Tyr Glu Glu Ala Val
        675                 680                 685

Ala Phe Ile Glu Arg Tyr Phe Gln Ser Tyr Pro Lys Val Arg Ala Trp
    690                 695                 700

Ile Glu Lys Thr Leu Ala Glu Gly Arg Glu Arg Gly Tyr Val Glu Thr
705                 710                 715                 720

Leu Phe Gly Arg Arg Arg Tyr Val Pro Asp Leu Ala Ser Arg Val Lys
                725                 730                 735

Ser Ile Arg Glu Ala Ala Glu Arg Met Ala Phe Asn Met Pro Val Gln
            740                 745                 750

Gly Thr Ala Ala Asp Leu Met Lys Leu Ala Met Val Lys Leu Phe Pro
```

```
        755                 760                 765

Arg Leu Gln Glu Leu Gly Ala Arg Met Leu Leu Gln Val His Asp Glu
    770                 775                 780

Leu Val Leu Glu Ala Pro Lys Glu Gln Ala Glu Glu Val Ala Gln Glu
785                 790                 795                 800

Ala Lys Arg Thr Met Glu Glu Val Trp Pro Leu Lys Val Pro Leu Glu
                805                 810                 815

Val Glu Val Gly Ile Gly Glu Asp Trp Leu Ser Ala Lys Ala
            820                 825                 830


<210> SEQ ID NO 23
<211> LENGTH: 833
<212> TYPE: PRT
<213> ORGANISM: Artificial Sequence
<220> FEATURE:
<223> OTHER INFORMATION: A derivative Thermus scotoductus polypeptide
      from strain SM3 in which Tyr is used in place of Phe at position
      668.

<400> SEQUENCE: 23

Met Arg Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285
```

-continued

```
Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Gln Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Tyr Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700
```

-continued

Arg Ala Trp Ile Glu Lys Thr Leu Ala Glu Gly Arg Glu Arg Gly Tyr
705 710 715 720

Val Glu Thr Leu Phe Gly Arg Arg Arg Tyr Val Pro Asp Leu Ala Ser
725 730 735

Arg Val Lys Ser Ile Arg Glu Ala Ala Glu Arg Met Ala Phe Asn Met
740 745 750

Pro Val Gln Gly Thr Ala Ala Asp Leu Met Lys Leu Ala Met Val Lys
755 760 765

Leu Phe Pro Arg Leu Gln Glu Leu Gly Ala Arg Met Leu Leu Gln Val
770 775 780

His Asp Glu Leu Val Leu Glu Ala Pro Lys Glu Gln Ala Glu Glu Val
785 790 795 800

Ala Gln Glu Ala Lys Arg Thr Met Glu Glu Val Trp Pro Leu Lys Val
805 810 815

Pro Leu Glu Val Glu Val Gly Ile Gly Glu Asp Trp Leu Ser Ala Lys
820 825 830

Ala

<210> SEQ ID NO 24
<211> LENGTH: 833
<212> TYPE: PRT
<213> ORGANISM: Artificial Sequence
<220> FEATURE:
<223> OTHER INFORMATION: A derivative Thermus scotoductus polypeptide from strain Vi7a in which Tyr is used in place of Phe at position 668.

<400> SEQUENCE: 24

Met Arg Ala Met Leu Pro Leu Phe Glu Pro Lys Gly Arg Val Leu Leu
1 5 10 15

Val Asp Gly His His Leu Ala Tyr Arg Thr Phe Phe Ala Leu Lys Gly
20 25 30

Leu Thr Thr Ser Arg Gly Glu Pro Val Gln Ala Val Tyr Gly Phe Ala
35 40 45

Lys Ser Leu Leu Lys Ala Leu Arg Glu Asp Gly Asp Val Val Ile Val
50 55 60

Val Phe Asp Ala Lys Ala Pro Ser Phe Arg His Gln Thr Tyr Glu Ala
65 70 75 80

Tyr Lys Ala Gly Arg Ala Pro Thr Pro Glu Asp Phe Pro Arg Gln Leu
85 90 95

Ala Leu Ile Lys Glu Met Val Asp Leu Leu Gly Leu Glu Arg Leu Glu
100 105 110

Val Pro Gly Phe Glu Ala Asp Asp Val Leu Ala Thr Leu Ala Lys Lys
115 120 125

Ala Glu Lys Glu Gly Tyr Glu Val Arg Ile Leu Thr Ala Asp Arg Asp
130 135 140

Leu Tyr Gln Leu Leu Ser Asp Arg Ile Ser Ile Leu His Pro Glu Gly
145 150 155 160

Tyr Leu Ile Thr Pro Glu Trp Leu Trp Glu Lys Tyr Gly Leu Lys Pro
165 170 175

Ser Gln Trp Val Asp Tyr Arg Ala Leu Ala Gly Asp Pro Ser Asp Asn
180 185 190

Ile Pro Gly Val Lys Gly Ile Gly Glu Lys Thr Ala Ala Lys Leu Ile
195 200 205

Arg Glu Trp Gly Ser Leu Glu Asn Leu Leu Lys His Leu Glu Gln Val
210 215 220

-continued

```
Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640
```

```
Thr Gln Thr Ala Ser Trp Met Phe Gly Val Pro Pro Glu Ala Val Asp
                645                 650                 655

Ser Leu Met Arg Arg Ala Ala Lys Thr Ile Asn Tyr Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830

Ala


<210> SEQ ID NO 25
<211> LENGTH: 833
<212> TYPE: PRT
<213> ORGANISM: Artificial Sequence
<220> FEATURE:
<223> OTHER INFORMATION: A derivative Thermus scotoductus polypeptide
      from strain X-1 in which Asp is used in place of Gly at position
      46 and Tyr in place of Phe at position 668.

<400> SEQUENCE: 25

Met Arg Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Glu Arg Ile Ser Ile Leu His Pro Glu Gly
145                 150                 155                 160
```

```
Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val Arg Thr Asp Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Arg Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575
```

-continued

Ser Ser Asp Pro Asn Leu Gln Asn Ile Pro Val Arg Thr Pro Leu Gly
580 585 590

Gln Arg Ile Arg Arg Ala Phe Val Ala Glu Glu Gly Trp Arg Leu Val
595 600 605

Val Leu Asp Tyr Ser Gln Ile Glu Leu Arg Val Leu Ala His Leu Ser
610 615 620

Gly Asp Glu Asn Leu Ile Arg Val Phe Gln Glu Gly Gln Asp Ile His
625 630 635 640

Thr Gln Thr Ala Ser Trp Met Phe Gly Val Pro Pro Glu Ala Val Asp
645 650 655

Ser Leu Met Arg Arg Ala Ala Lys Thr Ile Asn Tyr Gly Val Leu Tyr
660 665 670

Gly Met Ser Ala His Arg Leu Ser Gly Glu Leu Ala Ile Pro Tyr Glu
675 680 685

Glu Ala Val Ala Phe Ile Glu Arg Tyr Phe Gln Ser Tyr Pro Lys Val
690 695 700

Arg Ala Trp Ile Glu Lys Thr Leu Ala Glu Gly Arg Glu Arg Gly Tyr
705 710 715 720

Val Glu Thr Leu Phe Gly Arg Arg Arg Tyr Val Pro Asp Leu Ala Ser
725 730 735

Arg Val Lys Ser Ile Arg Glu Ala Ala Glu Arg Met Ala Phe Asn Met
740 745 750

Pro Val Gln Gly Thr Ala Ala Asp Leu Met Lys Leu Ala Met Val Lys
755 760 765

Leu Phe Pro Arg Leu Gln Glu Leu Gly Ala Arg Met Leu Leu Gln Val
770 775 780

His Asp Glu Leu Val Leu Glu Ala Pro Lys Glu Gln Ala Glu Glu Val
785 790 795 800

Ala Gln Glu Ala Lys Arg Thr Met Glu Glu Val Trp Pro Leu Lys Val
805 810 815

Pro Leu Glu Val Glu Val Gly Ile Gly Glu Asp Trp Leu Ser Ala Lys
820 825 830

Ala

<210> SEQ ID NO 26
<211> LENGTH: 830
<212> TYPE: PRT
<213> ORGANISM: Artificial Sequence
<220> FEATURE:
<223> OTHER INFORMATION: A derivative Thermus scotoductus polypeptide from strain X-1 in which Asp is used in place of Gly at position 46 and Tyr in place of Phe at position 668.

<400> SEQUENCE: 26

Met Leu Pro Leu Phe Glu Pro Lys Gly Arg Val Leu Leu Val Asp Gly
1 5 10 15

His His Leu Ala Tyr Arg Thr Phe Phe Ala Leu Lys Gly Leu Thr Thr
20 25 30

Ser Arg Gly Glu Pro Val Gln Ala Val Tyr Asp Phe Ala Lys Ser Leu
35 40 45

Leu Lys Ala Leu Arg Glu Asp Gly Asp Val Val Ile Val Val Phe Asp
50 55 60

Ala Lys Ala Pro Ser Phe Arg His Gln Thr Tyr Glu Ala Tyr Lys Ala
65 70 75 80

Gly Arg Ala Pro Thr Pro Glu Asp Phe Pro Arg Gln Leu Ala Leu Ile
85 90 95

-continued

```
Lys Glu Met Val Asp Leu Leu Gly Leu Glu Arg Leu Glu Val Pro Gly
            100                 105                 110

Phe Glu Ala Asp Asp Val Leu Ala Thr Leu Ala Lys Lys Ala Glu Lys
        115                 120                 125

Glu Gly Tyr Glu Val Arg Ile Leu Thr Ala Asp Arg Asp Leu Tyr Gln
    130                 135                 140

Leu Leu Ser Glu Arg Ile Ser Ile Leu His Pro Glu Gly Tyr Leu Ile
145                 150                 155                 160

Thr Pro Glu Trp Leu Trp Glu Lys Tyr Gly Leu Lys Pro Ser Gln Trp
                165                 170                 175

Val Asp Tyr Arg Ala Leu Ala Gly Asp Pro Ser Asp Asn Ile Pro Gly
            180                 185                 190

Val Lys Gly Ile Gly Glu Lys Thr Ala Ala Lys Leu Ile Arg Glu Trp
        195                 200                 205

Gly Ser Leu Glu Asn Leu Leu Lys His Leu Glu Gln Val Lys Pro Ala
    210                 215                 220

Ser Val Arg Glu Lys Ile Leu Ser His Met Glu Asp Leu Lys Leu Ser
225                 230                 235                 240

Leu Glu Leu Ser Arg Val Arg Thr Asp Leu Pro Leu Gln Val Asp Phe
                245                 250                 255

Ala Arg Arg Arg Glu Pro Asp Arg Glu Gly Leu Lys Ala Phe Leu Glu
            260                 265                 270

Arg Leu Glu Phe Gly Ser Leu Leu His Glu Phe Gly Leu Leu Glu Ser
        275                 280                 285

Pro Val Ala Ala Glu Glu Ala Pro Trp Pro Pro Pro Glu Gly Ala Phe
    290                 295                 300

Val Gly Tyr Val Leu Ser Arg Pro Glu Pro Met Trp Ala Glu Leu Asn
305                 310                 315                 320

Ala Leu Ala Ala Ala Trp Glu Gly Arg Val Tyr Arg Ala Glu Asp Pro
                325                 330                 335

Leu Glu Ala Leu Arg Gly Leu Gly Glu Val Arg Gly Leu Leu Ala Lys
            340                 345                 350

Asp Leu Ala Val Leu Ala Leu Arg Glu Gly Ile Ala Leu Ala Pro Gly
        355                 360                 365

Asp Asp Pro Met Leu Leu Ala Tyr Leu Leu Asp Pro Ser Asn Thr Ala
    370                 375                 380

Pro Glu Gly Val Ala Arg Arg Tyr Gly Gly Glu Trp Thr Glu Glu Ala
385                 390                 395                 400

Gly Glu Arg Ala Leu Leu Ser Glu Arg Leu Tyr Ala Ala Leu Leu Glu
                405                 410                 415

Arg Leu Lys Gly Glu Glu Arg Leu Leu Trp Leu Tyr Glu Glu Val Glu
            420                 425                 430

Lys Pro Leu Ser Arg Val Leu Ala His Met Glu Ala Thr Gly Val Arg
        435                 440                 445

Leu Asp Val Ala Tyr Leu Lys Ala Leu Ser Leu Glu Val Glu Ala Glu
    450                 455                 460

Leu Arg Arg Leu Glu Glu Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Ala Ile Gly Lys Thr Glu Lys Thr Gly Lys Arg Ser Thr
            500                 505                 510
```

-continued

Ser Ala Ala Val Leu Glu Ala Leu Arg Glu Ala His Pro Ile Val Asp
515 520 525

Arg Ile Leu Gln Tyr Arg Glu Leu Ser Lys Leu Lys Gly Thr Tyr Ile
530 535 540

Asp Pro Leu Pro Ala Leu Val His Pro Lys Thr Asn Arg Leu His Thr
545 550 555 560

Arg Phe Asn Gln Thr Ala Thr Ala Thr Gly Arg Leu Ser Ser Ser Asp
565 570 575

Pro Asn Leu Gln Asn Ile Pro Val Arg Thr Pro Leu Gly Gln Arg Ile
580 585 590

Arg Arg Ala Phe Val Ala Glu Glu Gly Trp Arg Leu Val Val Leu Asp
595 600 605

Tyr Ser Gln Ile Glu Leu Arg Val Leu Ala His Leu Ser Gly Asp Glu
610 615 620

Asn Leu Ile Arg Val Phe Gln Glu Gly Gln Asp Ile His Thr Gln Thr
625 630 635 640

Ala Ser Trp Met Phe Gly Val Pro Pro Glu Ala Val Asp Ser Leu Met
645 650 655

Arg Arg Ala Ala Lys Thr Ile Asn Tyr Gly Val Leu Tyr Gly Met Ser
660 665 670

Ala His Arg Leu Ser Gly Glu Leu Ala Ile Pro Tyr Glu Glu Ala Val
675 680 685

Ala Phe Ile Glu Arg Tyr Phe Gln Ser Tyr Pro Lys Val Arg Ala Trp
690 695 700

Ile Glu Lys Thr Leu Ala Glu Gly Arg Glu Arg Gly Tyr Val Glu Thr
705 710 715 720

Leu Phe Gly Arg Arg Arg Tyr Val Pro Asp Leu Ala Ser Arg Val Lys
725 730 735

Ser Ile Arg Glu Ala Ala Glu Arg Met Ala Phe Asn Met Pro Val Gln
740 745 750

Gly Thr Ala Ala Asp Leu Met Lys Leu Ala Met Val Lys Leu Phe Pro
755 760 765

Arg Leu Gln Glu Leu Gly Ala Arg Met Leu Leu Gln Val His Asp Glu
770 775 780

Leu Val Leu Glu Ala Pro Lys Glu Gln Ala Glu Glu Val Ala Gln Glu
785 790 795 800

Ala Lys Arg Thr Met Glu Glu Val Trp Pro Leu Lys Val Pro Leu Glu
805 810 815

Val Glu Val Gly Ile Gly Glu Asp Trp Leu Ser Ala Lys Ala
820 825 830

<210> SEQ ID NO 27
<211> LENGTH: 833
<212> TYPE: PRT
<213> ORGANISM: Artificial Sequence
<220> FEATURE:
<223> OTHER INFORMATION: A derivative Thermus scotoductus polypeptide from strain SM3 in which Asp is used in place of Gly at position 46 and Tyr in place of Phe at position 668.

<400> SEQUENCE: 27

Met Arg Ala Met Leu Pro Leu Phe Glu Pro Lys Gly Arg Val Leu Leu
1 5 10 15

Val Asp Gly His His Leu Ala Tyr Arg Thr Phe Phe Ala Leu Lys Gly
20 25 30

Leu Thr Thr Ser Arg Gly Glu Pro Val Gln Ala Val Tyr Asp Phe Ala

-continued

```
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Gln Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460
```

```
Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Tyr Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830

Ala
```

<210> SEQ ID NO 28
<211> LENGTH: 833
<212> TYPE: PRT
<213> ORGANISM: Artificial Sequence
<220> FEATURE:
<223> OTHER INFORMATION: A derivative Thermus scotoductus polypeptide from strain Vi7a in which Asp is used in place of Gly at position 46 and Tyr in place of Phe at position 668.

<400> SEQUENCE: 28

```
Met Arg Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Asp Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val His Thr Glu Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400
```

```
Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Trp Leu Asp Val Ala Tyr Leu Lys Ala Leu Ser Leu Glu Val
    450                 455                 460

Glu Ala Glu Leu Arg Arg Leu Glu Glu Glu Val His Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Asp Arg Ile Leu Gln Tyr Arg Glu Leu Ser Lys Leu Lys Gly
    530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Tyr Gly Val Leu Tyr
            660                 665                 670

Gly Met Ser Ala His Arg Leu Ser Gly Glu Leu Ala Ile Pro Tyr Glu
        675                 680                 685

Glu Ala Val Ala Phe Ile Glu Arg Tyr Phe Gln Ser Tyr Pro Lys Val
    690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Gln Glu Leu Gly Ala Arg Met Leu Leu Gln Val
    770                 775                 780

His Asp Glu Leu Val Leu Glu Ala Pro Lys Glu Gln Ala Glu Glu Val
785                 790                 795                 800

Ala Gln Glu Ala Lys Arg Thr Met Glu Glu Val Trp Pro Leu Lys Val
                805                 810                 815
```

-continued

Pro Leu Glu Val Glu Val Gly Ile Gly Glu Asp Trp Leu Ser Ala Lys
820 825 830

Ala

<210> SEQ ID NO 29
<211> LENGTH: 18
<212> TYPE: DNA
<213> ORGANISM: Thermus scotoductus

<400> SEQUENCE: 29
ggccaccacc tggcctac 18

<210> SEQ ID NO 30
<211> LENGTH: 17
<212> TYPE: DNA
<213> ORGANISM: Thermus scotoductus

<400> SEQUENCE: 30
cccacctcca cctccag 17

<210> SEQ ID NO 31
<211> LENGTH: 21
<212> TYPE: DNA
<213> ORGANISM: Thermus scotoductus

<400> SEQUENCE: 31
ctggccatgc tgaagctctt t 21

<210> SEQ ID NO 32
<211> LENGTH: 27
<212> TYPE: DNA
<213> ORGANISM: Thermus scotoductus

<400> SEQUENCE: 32
ataagggcga tgctgcccct ctttgag 27

<210> SEQ ID NO 33
<211> LENGTH: 24
<212> TYPE: DNA
<213> ORGANISM: Artificial Sequence
<220> FEATURE:
<223> OTHER INFORMATION: 5' forward primer for the amplification of the full-length Thermus scotoductus nucleic acid polymerase coding region.

<400> SEQUENCE: 33
catatgaggg cgatgctgcc cctc 24

<210> SEQ ID NO 34
<211> LENGTH: 6
<212> TYPE: DNA
<213> ORGANISM: Artificial Sequence
<220> FEATURE:
<223> OTHER INFORMATION: Recognition site for the restriction enzyme Nde I.

<400> SEQUENCE: 34 catatg 6

<210> SEQ ID NO 35
<211> LENGTH: 18
<212> TYPE: DNA
<213> ORGANISM: Thermus scotoductus

<400> SEQUENCE: 35
ctccacctcc aggggcac 18

<210> SEQ ID NO 36
<211> LENGTH: 21
<212> TYPE: DNA
<213> ORGANISM: Thermus scotoductus

<400> SEQUENCE: 36
ctggccatgg tgaagctctt t 21

<210> SEQ ID NO 37
<211> LENGTH: 6
<212> TYPE: DNA
<213> ORGANISM: Artificial Sequence
<220> FEATURE:
<223> OTHER INFORMATION: Recognition site for the restriction enzyme Sal I.

<400> SEQUENCE: 37 gtcgac 6

<210> SEQ ID NO 38
<211> LENGTH: 25
<212> TYPE: DNA
<213> ORGANISM: Artificial Sequence
<220> FEATURE:
<223> OTHER INFORMATION: A primer.

<400> SEQUENCE: 38
gtcgactagg ccttggcgaa agcca 25

<210> SEQ ID NO 39
<211> LENGTH: 29
<212> TYPE: PRT
<213> ORGANISM: Thermus scotoductus

<400> SEQUENCE: 39

Leu Leu Lys Ala Leu Arg Glu Asp Gly Asp Val Val Ile Val Val Phe
1 5 10 15

Asp Ala Lys Ala Pro Ser Phe Arg His Gln Thr Tyr Glu
20 25

<210> SEQ ID NO 40
<211> LENGTH: 36
<212> TYPE: PRT
<213> ORGANISM: Thermus scotoductus

<400> SEQUENCE: 40

Gly Glu Lys Thr Ala Ala Lys Leu Ile Arg Glu Trp Gly Ser Leu Glu
1 5 10 15

Asn Leu Leu Lys His Leu Glu Gln Val Lys Pro Ala Ser Val Arg Glu
20 25 30

Lys Ile Leu Ser
35

<210> SEQ ID NO 41
<211> LENGTH: 40
<212> TYPE: PRT
<213> ORGANISM: Thermus scotoductus

<400> SEQUENCE: 41

Val Gly Tyr Val Leu Ser Arg Pro Glu Pro Met Trp Ala Glu Leu Asn
1 5 10 15

```
Ala Leu Ala Ala Ala Trp Glu Gly Arg Val Tyr Arg Ala Glu Asp Pro
            20                  25                  30

Leu Glu Ala Leu Arg Gly Leu Gly
        35                  40


<210> SEQ ID NO 42
<211> LENGTH: 21
<212> TYPE: PRT
<213> ORGANISM: Thermus scotoductus

<400> SEQUENCE: 42

Arg Leu Tyr Ala Ala Leu Leu Glu Arg Leu Lys Gly Glu Glu Arg Leu
 1               5                  10                  15

Leu Trp Leu Tyr Glu
            20


<210> SEQ ID NO 43
<211> LENGTH: 32
<212> TYPE: PRT
<213> ORGANISM: Thermus scotoductus

<400> SEQUENCE: 43

Pro Ile Val Asp Arg Ile Leu Gln Tyr Arg Glu Leu Ser Lys Leu Lys
 1               5                  10                  15

Gly Thr Tyr Ile Asp Pro Leu Pro Ala Leu Val His Pro Lys Thr Asn
            20                  25                  30


<210> SEQ ID NO 44
<211> LENGTH: 36
<212> TYPE: PRT
<213> ORGANISM: Thermus scotoductus

<400> SEQUENCE: 44

Glu Glu Val Ala Gln Glu Ala Lys Arg Thr Met Glu Glu Val Trp Pro
 1               5                  10                  15

Leu Lys Val Pro Leu Glu Val Glu Val Gly Ile Gly Glu Asp Trp Leu
            20                  25                  30

Ser Ala Lys Ala
        35


<210> SEQ ID NO 45
<211> LENGTH: 544
<212> TYPE: PRT
<213> ORGANISM: Thermus scotoductus

<400> SEQUENCE: 45

Glu Ser Pro Val Ala Ala Glu Glu Ala Pro Trp Pro Pro Pro Glu Gly
 1               5                  10                  15

Ala Phe Val Gly Tyr Val Leu Ser Arg Pro Glu Pro Met Trp Ala Glu
            20                  25                  30

Leu Asn Ala Leu Ala Ala Ala Trp Glu Gly Arg Val Tyr Arg Ala Glu
        35                  40                  45

Asp Pro Leu Glu Ala Leu Arg Gly Leu Gly Glu Val Arg Gly Leu Leu
    50                  55                  60

Ala Lys Asp Leu Ala Val Leu Ala Leu Arg Glu Gly Ile Ala Leu Ala
65                  70                  75                  80

Pro Gly Asp Asp Pro Met Leu Leu Ala Tyr Leu Leu Asp Pro Ser Asn
                85                  90                  95

Thr Ala Pro Glu Gly Val Ala Arg Arg Tyr Gly Gly Glu Trp Thr Glu
```

-continued

```
            100                 105                 110

Glu Ala Gly Glu Arg Ala Leu Leu Ser Glu Arg Leu Tyr Ala Ala Leu
        115                 120                 125

Leu Glu Arg Leu Lys Gly Glu Glu Arg Leu Leu Trp Leu Tyr Glu Glu
    130                 135                 140

Val Glu Lys Pro Leu Ser Arg Val Leu Ala His Met Glu Ala Thr Gly
145                 150                 155                 160

Val Arg Leu Asp Val Ala Tyr Leu Lys Ala Leu Ser Leu Glu Val Glu
                165                 170                 175

Ala Glu Leu Arg Arg Leu Glu Glu Glu Val His Arg Leu Ala Gly His
            180                 185                 190

Pro Phe Asn Leu Asn Ser Arg Asp Gln Leu Glu Arg Val Leu Phe Asp
        195                 200                 205

Glu Leu Gly Leu Pro Ala Ile Gly Lys Thr Glu Lys Thr Gly Lys Arg
    210                 215                 220

Ser Thr Ser Ala Ala Val Leu Glu Ala Leu Arg Glu Ala His Pro Ile
225                 230                 235                 240

Val Asp Arg Ile Leu Gln Tyr Arg Glu Leu Ser Lys Leu Lys Gly Thr
                245                 250                 255

Tyr Ile Asp Pro Leu Pro Ala Leu Val His Pro Lys Thr Asn Arg Leu
            260                 265                 270

His Thr Arg Phe Asn Gln Thr Ala Thr Ala Thr Gly Arg Leu Ser Ser
        275                 280                 285

Ser Asp Pro Asn Leu Gln Asn Ile Pro Val Arg Thr Pro Leu Gly Gln
    290                 295                 300

Arg Ile Arg Arg Ala Phe Val Ala Glu Glu Gly Trp Arg Leu Val Val
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Gln Asp Ile His Thr
            340                 345                 350

Gln Thr Ala Ser Trp Met Phe Gly Val Pro Pro Glu Ala Val Asp Ser
        355                 360                 365

Leu Met Arg Arg Ala Ala Lys Thr Ile Asn Phe Gly Val Leu Tyr Gly
    370                 375                 380

Met Ser Ala His Arg Leu Ser Gly Glu Leu Ala Ile Pro Tyr Glu Glu
385                 390                 395                 400

Ala Val Ala Phe Ile Glu Arg Tyr Phe Gln Ser Tyr Pro Lys Val Arg
                405                 410                 415

Ala Trp Ile Glu Lys Thr Leu Ala Glu Gly Arg Glu Arg Gly Tyr Val
            420                 425                 430

Glu Thr Leu Phe Gly Arg Arg Arg Tyr Val Pro Asp Leu Ala Ser Arg
        435                 440                 445

Val Lys Ser Ile Arg Glu Ala Ala Glu Arg Met Ala Phe Asn Met Pro
    450                 455                 460

Val Gln Gly Thr Ala Ala Asp Leu Met Lys Leu Ala Met Val Lys Leu
465                 470                 475                 480

Phe Pro Arg Leu Gln Glu Leu Gly Ala Arg Met Leu Leu Gln Val His
                485                 490                 495

Asp Glu Leu Val Leu Glu Ala Pro Lys Glu Gln Ala Glu Glu Val Ala
            500                 505                 510

Gln Glu Ala Lys Arg Thr Met Glu Glu Val Trp Pro Leu Lys Val Pro
        515                 520                 525
```

```
Leu Glu Val Glu Val Gly Ile Gly Glu Asp Trp Leu Ser Ala Lys Ala
    530                 535                 540


<210> SEQ ID NO 46
<211> LENGTH: 544
<212> TYPE: PRT
<213> ORGANISM: Thermus scotoductus

<400> SEQUENCE: 46

Glu Ser Pro Val Ala Ala Glu Glu Ala Pro Trp Pro Pro Pro Glu Gly
 1               5                  10                  15

Ala Phe Val Gly Tyr Val Leu Ser Arg Pro Glu Pro Met Trp Ala Glu
            20                  25                  30

Leu Asn Ala Leu Ala Ala Ala Trp Glu Gly Arg Val Tyr Arg Ala Glu
        35                  40                  45

Asp Pro Leu Glu Ala Leu Arg Gly Leu Gly Glu Val Arg Gly Leu Leu
    50                  55                  60

Ala Lys Asp Leu Ala Val Leu Ala Leu Arg Glu Gly Ile Ala Leu Ala
65                  70                  75                  80

Gln Gly Asp Asp Pro Met Leu Leu Ala Tyr Leu Leu Asp Pro Ser Asn
                85                  90                  95

Thr Ala Pro Glu Gly Val Ala Arg Arg Tyr Gly Gly Glu Trp Thr Glu
            100                 105                 110

Glu Ala Gly Glu Arg Ala Leu Leu Ser Glu Arg Leu Tyr Ala Ala Leu
        115                 120                 125

Leu Glu Arg Leu Lys Gly Glu Glu Arg Leu Leu Trp Leu Tyr Glu Glu
    130                 135                 140

Val Glu Lys Pro Leu Ser Arg Val Leu Ala His Met Glu Ala Thr Gly
145                 150                 155                 160

Val Trp Leu Asp Val Ala Tyr Leu Lys Ala Leu Ser Leu Glu Val Glu
                165                 170                 175

Ala Glu Leu Arg Arg Leu Glu Glu Glu Val His Arg Leu Ala Gly His
            180                 185                 190

Pro Phe Asn Leu Asn Ser Arg Asp Gln Leu Glu Arg Val Leu Phe Asp
        195                 200                 205

Glu Leu Gly Leu Pro Ala Ile Gly Lys Thr Glu Lys Thr Gly Lys Arg
    210                 215                 220

Ser Thr Ser Ala Ala Val Leu Glu Ala Leu Arg Glu Ala His Pro Ile
225                 230                 235                 240

Val Asp Arg Ile Leu Gln Tyr Arg Glu Leu Ser Lys Leu Lys Gly Thr
                245                 250                 255

Tyr Ile Asp Pro Leu Pro Ala Leu Val His Pro Lys Thr Asn Arg Leu
            260                 265                 270

His Thr Arg Phe Asn Gln Thr Ala Thr Ala Thr Gly Arg Leu Ser Ser
        275                 280                 285

Ser Asp Pro Asn Leu Gln Asn Ile Pro Val Arg Thr Pro Leu Gly Gln
    290                 295                 300

Arg Ile Arg Arg Ala Phe Val Ala Glu Glu Gly Trp Arg Leu Val Val
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Gln Asp Ile His Thr
            340                 345                 350

Gln Thr Ala Ser Trp Met Phe Gly Val Pro Pro Glu Ala Val Asp Ser
```

-continued

```
        355                 360                 365

Leu Met Arg Arg Ala Ala Lys Thr Ile Asn Phe Gly Val Leu Tyr Gly
    370                 375                 380

Met Ser Ala His Arg Leu Ser Gly Glu Leu Ala Ile Pro Tyr Glu Glu
385                 390                 395                 400

Ala Val Ala Phe Ile Glu Arg Tyr Phe Gln Ser Tyr Pro Lys Val Arg
                405                 410                 415

Ala Trp Ile Glu Lys Thr Leu Ala Glu Gly Arg Glu Arg Gly Tyr Val
            420                 425                 430

Glu Thr Leu Phe Gly Arg Arg Arg Tyr Val Pro Asp Leu Ala Ser Arg
        435                 440                 445

Val Lys Ser Ile Arg Glu Ala Ala Glu Arg Met Ala Phe Asn Met Pro
    450                 455                 460

Val Gln Gly Thr Ala Ala Asp Leu Met Lys Leu Ala Met Val Lys Leu
465                 470                 475                 480

Phe Pro Arg Leu Gln Glu Leu Gly Ala Arg Met Leu Leu Gln Val His
                485                 490                 495

Asp Glu Leu Val Leu Glu Ala Pro Lys Glu Gln Ala Glu Glu Val Ala
            500                 505                 510

Gln Glu Ala Lys Arg Thr Met Glu Glu Val Trp Pro Leu Lys Val Pro
        515                 520                 525

Leu Glu Val Glu Val Gly Ile Gly Glu Asp Trp Leu Ser Ala Lys Ala
    530                 535                 540


<210> SEQ ID NO 47
<211> LENGTH: 544
<212> TYPE: PRT
<213> ORGANISM: Thermus scotoductus

<400> SEQUENCE: 47

Glu Ser Pro Val Ala Ala Glu Glu Ala Pro Trp Pro Pro Pro Glu Gly
 1               5                  10                  15

Ala Phe Val Gly Tyr Val Leu Ser Arg Pro Glu Pro Met Trp Ala Glu
            20                  25                  30

Leu Asn Ala Leu Ala Ala Ala Trp Glu Gly Arg Val Tyr Arg Ala Glu
        35                  40                  45

Asp Pro Leu Glu Ala Leu Arg Gly Leu Gly Glu Val Arg Gly Leu Leu
    50                  55                  60

Ala Lys Asp Leu Ala Val Leu Ala Leu Arg Glu Gly Ile Ala Leu Ala
65                  70                  75                  80

Pro Gly Asp Asp Pro Met Leu Leu Ala Tyr Leu Leu Asp Pro Ser Asn
                85                  90                  95

Thr Ala Pro Glu Gly Val Ala Arg Arg Tyr Gly Gly Glu Trp Thr Glu
            100                 105                 110

Glu Ala Gly Glu Arg Ala Leu Leu Ser Glu Arg Leu Tyr Ala Ala Leu
        115                 120                 125

Leu Glu Arg Leu Lys Gly Glu Glu Arg Leu Leu Trp Leu Tyr Glu Glu
    130                 135                 140

Val Glu Lys Pro Leu Ser Arg Val Leu Ala His Met Glu Ala Thr Gly
145                 150                 155                 160

Val Trp Leu Asp Val Ala Tyr Leu Lys Ala Leu Ser Leu Glu Val Glu
                165                 170                 175

Ala Glu Leu Arg Arg Leu Glu Glu Glu Val His Arg Leu Ala Gly His
            180                 185                 190
```

-continued

Pro Phe Asn Leu Asn Ser Arg Asp Gln Leu Glu Arg Val Leu Phe Asp
        195                 200                 205

Glu Leu Gly Leu Pro Ala Ile Gly Lys Thr Glu Lys Thr Gly Lys Arg
    210                 215                 220

Ser Thr Ser Ala Ala Val Leu Glu Ala Leu Arg Glu Ala His Pro Ile
225                 230                 235                 240

Val Asp Arg Ile Leu Gln Tyr Arg Glu Leu Ser Lys Leu Lys Gly Thr
                245                 250                 255

Tyr Ile Asp Pro Leu Pro Ala Leu Val His Pro Lys Thr Asn Arg Leu
            260                 265                 270

His Thr Arg Phe Asn Gln Thr Ala Thr Ala Thr Gly Arg Leu Ser Ser
        275                 280                 285

Ser Asp Pro Asn Leu Gln Asn Ile Pro Val Arg Thr Pro Leu Gly Gln
    290                 295                 300

Arg Ile Arg Arg Ala Phe Val Ala Glu Glu Gly Trp Arg Leu Val Val
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Gln Asp Ile His Thr
            340                 345                 350

Gln Thr Ala Ser Trp Met Phe Gly Val Pro Pro Glu Ala Val Asp Ser
        355                 360                 365

Leu Met Arg Arg Ala Ala Lys Thr Ile Asn Phe Gly Val Leu Tyr Gly
    370                 375                 380

Met Ser Ala His Arg Leu Ser Gly Glu Leu Ala Ile Pro Tyr Glu Glu
385                 390                 395                 400

Ala Val Ala Phe Ile Glu Arg Tyr Phe Gln Ser Tyr Pro Lys Val Arg
                405                 410                 415

Ala Trp Ile Glu Lys Thr Leu Ala Glu Gly Arg Glu Arg Gly Tyr Val
            420                 425                 430

Glu Thr Leu Phe Gly Arg Arg Arg Tyr Val Pro Asp Leu Ala Ser Arg
        435                 440                 445

Val Lys Ser Ile Arg Glu Ala Ala Glu Arg Met Ala Phe Asn Met Pro
    450                 455                 460

Val Gln Gly Thr Ala Ala Asp Leu Met Lys Leu Ala Met Val Lys Leu
465                 470                 475                 480

Phe Pro Arg Leu Gln Glu Leu Gly Ala Arg Met Leu Leu Gln Val His
                485                 490                 495

Asp Glu Leu Val Leu Glu Ala Pro Lys Glu Gln Ala Glu Glu Val Ala
            500                 505                 510

Gln Glu Ala Lys Arg Thr Met Glu Glu Val Trp Pro Leu Lys Val Pro
        515                 520                 525

Leu Glu Val Glu Val Gly Ile Gly Glu Asp Trp Leu Ser Ala Lys Ala
    530                 535                 540

<210> SEQ ID NO 48
<211> LENGTH: 832
<212> TYPE: PRT
<213> ORGANISM: Thermus aquaticus

<400> SEQUENCE: 48

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

-continued

```
Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445
```

Val Arg Leu Asp Val Ala Tyr Leu Arg Ala Leu Ser Leu Glu Val Ala
450 455 460

Glu Glu Ile Ala Arg Leu Glu Ala Glu Val Phe Arg Leu Ala Gly His
465 470 475 480

Pro Phe Asn Leu Asn Ser Arg Asp Gln Leu Glu Arg Val Leu Phe Asp
485 490 495

Glu Leu Gly Leu Pro Ala Ile Gly Lys Thr Glu Lys Thr Gly Lys Arg
500 505 510

Ser Thr Ser Ala Ala Val Leu Glu Ala Leu Arg Glu Ala His Pro Ile
515 520 525

Val Glu Lys Ile Leu Gln Tyr Arg Glu Leu Thr Lys Leu Lys Ser Thr
530 535 540

Tyr Ile Asp Pro Leu Pro Asp Leu Ile His Pro Arg Thr Gly Arg Leu
545 550 555 560

His Thr Arg Phe Asn Gln Thr Ala Thr Ala Thr Gly Arg Leu Ser Ser
565 570 575

Ser Asp Pro Asn Leu Gln Asn Ile Pro Val Arg Thr Pro Leu Gly Gln
580 585 590

Arg Ile Arg Arg Ala Phe Ile Ala Glu Glu Gly Trp Leu Leu Val Ala
595 600 605

Leu Asp Tyr Ser Gln Ile Glu Leu Arg Val Leu Ala His Leu Ser Gly
610 615 620

Asp Glu Asn Leu Ile Arg Val Phe Gln Glu Gly Arg Asp Ile His Thr
625 630 635 640

Glu Thr Ala Ser Trp Met Phe Gly Val Pro Arg Glu Ala Val Asp Pro
645 650 655

Leu Met Arg Arg Ala Ala Lys Thr Ile Asn Phe Gly Val Leu Tyr Gly
660 665 670

Met Ser Ala His Arg Leu Ser Gln Glu Leu Ala Ile Pro Tyr Glu Glu
675 680 685

Ala Gln Ala Phe Ile Glu Arg Tyr Phe Gln Ser Phe Pro Lys Val Arg
690 695 700

Ala Trp Ile Glu Lys Thr Leu Glu Glu Gly Arg Arg Arg Gly Tyr Val
705 710 715 720

Glu Thr Leu Phe Gly Arg Arg Arg Tyr Val Pro Asp Leu Glu Ala Arg
725 730 735

Val Lys Ser Val Arg Glu Ala Ala Glu Arg Met Ala Phe Asn Met Pro
740 745 750

Val Gln Gly Thr Ala Ala Asp Leu Met Lys Leu Ala Met Val Lys Leu
755 760 765

Phe Pro Arg Leu Glu Glu Met Gly Ala Arg Met Leu Leu Gln Val His
770 775 780

Asp Glu Leu Val Leu Glu Ala Pro Lys Glu Arg Ala Glu Ala Val Ala
785 790 795 800

Arg Leu Ala Lys Glu Val Met Glu Gly Val Tyr Pro Leu Ala Val Pro
805 810 815

Leu Glu Val Glu Val Gly Ile Gly Glu Asp Trp Leu Ser Ala Lys Glu
820 825 830

<210> SEQ ID NO 49
<211> LENGTH: 834
<212> TYPE: PRT
<213> ORGANISM: Thermus thermophilus

<400> SEQUENCE: 49

-continued

```
Met Glu Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415
```

-continued

```
Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly
```

<210> SEQ ID NO 50
<211> LENGTH: 833
<212> TYPE: PRT
<213> ORGANISM: Thermus filiformis

<400> SEQUENCE: 50

```
Met Thr Pro Leu Phe Asp Leu Glu Glu Pro Pro Lys Arg Val Leu Leu
 1               5                  10                  15

Val Asp Gly His His Leu Ala Tyr Arg Thr Phe Tyr Ala Leu Ser Leu
            20                  25                  30

Thr Thr Ser Arg Gly Glu Pro Val Gln Met Val Tyr Gly Phe Ala Arg
        35                  40                  45

Ser Leu Leu Lys Ala Leu Lys Glu Asp Gly Gln Ala Val Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Val Lys Arg Leu Val Asp Leu Leu Gly Leu Val Arg Leu Glu Ala
            100                 105                 110

Pro Gly Tyr Glu Ala Asp Asp Val Leu Gly Thr Leu Ala Lys Lys Ala
        115                 120                 125

Glu Arg Glu Gly Met Glu Val Arg Ile Leu Thr Gly Asp Arg Asp Phe
    130                 135                 140

Phe Gln Leu Leu Ser Glu Lys Val Ser Val Leu Leu Pro Asp Gly Thr
145                 150                 155                 160

Leu Val Thr Pro Lys Asp Val Gln Glu Lys Tyr Gly Val Pro Pro Glu
                165                 170                 175

Arg Trp Val Asp Phe Arg Ala Leu Thr Gly Asp Arg Ser Asp Asn Ile
            180                 185                 190

Pro Gly Val Ala Gly Ile Gly Glu Lys Thr Ala Leu Arg Leu Leu Ala
        195                 200                 205

Glu Trp Gly Ser Val Glu Asn Leu Leu Lys Asn Leu Asp Arg Val Lys
    210                 215                 220

Pro Asp Ser Leu Arg Arg Lys Ile Glu Ala His Leu Glu Asp Leu His
225                 230                 235                 240

Leu Ser Leu Asp Leu Ala Arg Ile Arg Thr Asp Leu Pro Leu Glu Val
                245                 250                 255

Asp Phe Lys Ala Leu Arg Arg Arg Thr Pro Asp Leu Glu Gly Leu Arg
            260                 265                 270

Ala Phe Leu Glu Glu Leu Glu Phe Gly Ser Leu Leu His Glu Phe Gly
        275                 280                 285

Leu Leu Gly Gly Glu Lys Pro Arg Glu Glu Ala Pro Trp Pro Pro Pro
    290                 295                 300

Glu Gly Ala Phe Val Gly Phe Leu Leu Ser Arg Lys Glu Pro Met Trp
305                 310                 315                 320

Ala Glu Leu Leu Ala Leu Ala Ala Ala Ser Glu Gly Arg Val His Arg
                325                 330                 335

Ala Thr Ser Pro Val Glu Ala Leu Ala Asp Leu Lys Glu Ala Arg Gly
            340                 345                 350

Phe Leu Ala Lys Asp Leu Ala Val Leu Ala Leu Arg Glu Gly Val Ala
        355                 360                 365

Leu Asp Pro Thr Asp Asp Pro Leu Leu Val Ala Tyr Leu Leu Asp Pro
```

```
    370                 375                 380

Ala Asn Thr His Pro Glu Gly Val Ala Arg Arg Tyr Gly Gly Glu Phe
385                 390                 395                 400

Thr Glu Asp Ala Ala Glu Arg Ala Leu Leu Ser Glu Arg Leu Phe Gln
                405                 410                 415

Asn Leu Phe Pro Arg Leu Ser Glu Lys Leu Leu Trp Leu Tyr Gln Glu
            420                 425                 430

Val Glu Arg Pro Leu Ser Arg Val Leu Ala His Met Glu Ala Arg Gly
        435                 440                 445

Val Arg Leu Asp Val Pro Leu Leu Glu Ala Leu Ser Phe Glu Leu Glu
    450                 455                 460

Lys Glu Met Glu Arg Leu Glu Gly Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Thr Pro Val Gly Arg Thr Glu Lys Thr Gly Lys Arg
            500                 505                 510

Ser Thr Ala Gln Gly Ala Leu Glu Ala Leu Arg Gly Ala His Pro Ile
        515                 520                 525

Val Glu Leu Ile Leu Gln Tyr Arg Glu Leu Ser Lys Leu Lys Ser Thr
    530                 535                 540

Tyr Leu Asp Pro Leu Pro Arg Leu Val His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Lys Ala Phe Val Ala Glu Glu Gly Trp Leu Leu Leu Ala
        595                 600                 605

Ala Asp Tyr Ser Gln Ile Glu Leu Arg Val Leu Ala His Leu Ser Gly
    610                 615                 620

Asp Glu Asn Leu Lys Arg Val Phe Arg Glu Gly Lys Asp Ile His Thr
625                 630                 635                 640

Glu Thr Ala Ala Trp Met Phe Gly Leu Asp Pro Ala Leu Val Asp Pro
                645                 650                 655

Lys Met Arg Arg Ala Ala Lys Thr Val Asn Phe Gly Val Leu Tyr Gly
            660                 665                 670

Met Ser Ala His Arg Leu Ser Gln Glu Leu Gly Ile Asp Tyr Lys Glu
        675                 680                 685

Ala Glu Ala Phe Ile Glu Arg Tyr Phe Gln Ser Phe Pro Lys Val Arg
    690                 695                 700

Ala Trp Ile Glu Arg Thr Leu Glu Glu Gly Arg Thr Arg Gly Tyr Val
705                 710                 715                 720

Glu Thr Leu Phe Gly Arg Arg Arg Tyr Val Pro Asp Leu Ala Ser Arg
                725                 730                 735

Val Arg Ser Val Arg Glu Ala Ala Glu Arg Met Ala Phe Asn Met Pro
            740                 745                 750

Val Gln Gly Thr Ala Ala Asp Leu Met Lys Ile Ala Met Val Lys Leu
        755                 760                 765

Phe Pro Arg Leu Lys Pro Leu Gly Ala His Leu Leu Leu Gln Val His
    770                 775                 780

Asp Glu Leu Val Leu Glu Val Pro Glu Asp Arg Ala Glu Glu Ala Lys
785                 790                 795                 800
```

-continued

```
Ala Leu Val Lys Glu Val Met Glu Asn Ala Tyr Pro Leu Asp Val Pro
            805                 810                 815

Leu Glu Val Glu Val Gly Val Gly Arg Asp Trp Leu Glu Ala Lys Gln
        820                 825                 830

Asp
```

What is claimed is:

1. An isolated derivative nucleic acid polymerase comprising an amino acid sequence having at least 95% sequence identity to SEQ ID NO:14, wherein said amino acid sequence comprises an Asp in place of Gly at a position corresponding to amino acid position 46 of SEQ ID NO:13, wherein said amino acid sequence further comprises an Arg at a position corresponding to amino acid position 250 of SEQ ID NO:13, and wherein said derivative nucleic acid polymerase has decreased 5'-3' exonuclease activity compared to a wild type nucleic acid polymerase comprising SEQ ID NO:14.

2. The derivative nucleic acid polymerase according to claim 1, wherein said derivative nucleic acid polymerase is thermostable.

3. The derivative nucleic acid polymerase according to claim 1, wherein said amino acid sequence further comprises a Tyr in place of Phe at a position corresponding to amino acid position 668 of SEQ ID NO:13.

4. The derivative nucleic acid polymerase according to claim 1, wherein said amino acid sequence comprises Val and Arg at positions corresponding to amino acid positions 249 and 250, respectively, of SEQ ID NO:13.

5. The derivative nucleic acid polymerase according to claim 1, wherein said amino acid sequence comprises Arg and Thr at positions corresponding to amino acid positions 250 and 251, respectively, of SEQ ID NO:13.

6. The derivative nucleic acid polymerase according to claim 1, wherein said amino acid sequence comprises Val, Arg, and Thr at positions corresponding to amino acid positions 249-251, respectively, of SEQ ID NO:13.

7. An isolated derivative nucleic acid polymerase comprising an amino acid sequence having at least 95% sequence identity to SEQ ID NO:14, wherein said amino acid sequence comprises an Asp in place of Gly at a position corresponding to amino acid position 46 of SEQ ID NO:13, wherein said polymerase further comprises a Pro at a position corresponding to amino acid position 254 of SEQ ID NO:13, and wherein said nucleic acid polymerase has decreased 5'-3' exonuclease activity compared to a wild type nucleic acid polymerase comprising SEQ ID NO:14.

8. The derivative nucleic acid polymerase according to claim 7, wherein said derivative nucleic acid polymerase is thermostable.

9. The derivative nucleic acid polymerase according to claim 7, wherein said amino acid sequence further comprises a Tyr in place of Phe at a position corresponding to amino acid position 668 of SEQ ID NO:13.

10. The derivative nucleic acid polymerase according to claim 7, wherein said amino acid sequence comprises Leu and Pro at positions corresponding to amino acid positions 253 and 254, respectively, of SEQ ID NO:13.

11. The derivative nucleic acid polymerase according to claim 7, wherein said amino acid sequence comprises Pro and Leu at positions corresponding to amino acid position 254 and 255, respectively, of SEQ ID NO:13.

12. The derivative nucleic acid polymerase according to claim 7, wherein said amino acid sequence comprises Leu, Pro, and Leu at positions corresponding to amino acid positions 253-255, respectively, of SEQ ID NO:13.

13. An isolated derivative nucleic acid polymerase comprising an amino acid sequence having at least 95% sequence identity to SEQ ID NO:14, wherein said amino acid sequence comprises an Asp in place of Gly at a position corresponding to amino acid position 46 of SEQ ID NO:13, wherein said polymerase further comprises a Leu at a position corresponding to amino acid position 471 of SEQ ID NO:13, and wherein said nucleic acid polymerase has decreased 5'-3' exonuclease activity compared to a wild type nucleic acid polymerase comprising SEQ ID NO:14.

14. The derivative nucleic acid polymerase according to claim 13, wherein said derivative nucleic acid polymerase is thermostable.

15. The derivative nucleic acid polymerase of claim 13, wherein said amino acid sequence further comprises a Tyr in place of Phe at a position corresponding to position 668 of SEQ ID NO:13.

16. The derivative nucleic acid polymerase according to claim 13, wherein said amino acid sequence comprises Arg and Leu at positions corresponding to amino acid positions 470 and 471, respectively, of SEQ ID NO:13.

17. The derivative nucleic acid polymerase according to claim 13, wherein said amino acid sequence comprises Leu and Glu at positions corresponding to amino acid positions 471 and 472, respectively, of SEQ ID NO:13.

18. The derivative nucleic acid polymerase according to claim 13, wherein said amino acid sequence comprises Arg, Leu, and Glu at positions corresponding to amino acid positions 470-472, respectively, of SEQ ID NO:13.

* * * * *